US006399378B1

(12) United States Patent
Ward et al.

(10) Patent No.: US 6,399,378 B1
(45) Date of Patent: Jun. 4, 2002

(54) ANTISENSE MODULATION OF RECQL2 EXPRESSION

(75) Inventors: Donna T. Ward, Murrieta; Andrew T. Watt, Vista, both of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/798,096

(22) Filed: Mar. 1, 2001

(51) Int. Cl.$^7$ .................... C07H 21/04; C12N 15/09; C12Q 1/68
(52) U.S. Cl. .................... 435/375; 435/455; 435/6; 517/44; 536/23.1; 536/24.1; 536/24.5
(58) Field of Search ................ 536/23.1, 24.1, 536/24.5; 514/44; 435/320.1, 325, 455, 375, 6; 530/350

(56) References Cited

U.S. PATENT DOCUMENTS 5,801,154 A * 9/1998 Baracchini et al. ............ 514/44
5,824,501 A   10/1998 Ellis et al. .................. 435/69.1

OTHER PUBLICATIONS

Kuang–Yu Jen et al., Suppression of Gene Expression by Targeted Disruption of Messenger RNA: Available Options and Current Strategies, Stem Cells; 18, pp. 307–319.*
Alan M. Gewitz et al., Facilitating oligonucleotide delivery: Helping antisense deliver on its promise, Proc. Natl. Acad. Sci USA, vol. 93, pp. 3161–3163.*
Sudhir Agrawal, Antisense oligonucleotides: towards clinical trials, Tibtech, Oct. 1996, vol. 14, pp. 376–387.*
Douglas W. Green et al., Antisense Oligonucleotides: An Evolving Technology for the Modulation of Gene Expression in Human Disease, Joural America College Surgery, vol. 191, No. 1, pp. 93–105.*
Andrea D. Branch, TIBS—23, Feb. 1998, pp. 45–50.*

Chakraverty et al., Defending genome integrity during DNA replication: a proposed role of RecQ family helicases, BioEssays, 1999, 21:286–294.
Chester et al., Stage–specific apoptosis, developmental delay, and embryonic lethality in mice homozygous for a targeted disruption in the murine Bloom's syndrom gene, Genes Dev., 1998, 12:3382–3393.
Cogoni et al., Posttranscriptional gene silencing in Neurospora by a RecQ DNA helicase, Science, 1999, 286:2342–2344.
Ellis et al., Molecular genetics of Bloom's syndrome, Hum. Mol. Genet., 1996, 5:1457–1463.
Ellis et al., The Bloom's syndrome gene product is homologous to ReQ helicases, Cell, 1995, 83:655–666.
Frei et al., RecQ–like helicases: the DNA replication checkpoint connection, J. Cell Sci., 2000, 113:2641–2646.
Karow et al., ReQ family helicases: roles in cancer and aging, Curr. Opin. Genet. Dev., 2000, 10:32–38.
Kawabe et al., Differential regulation of human RecQ family helicases in cell transformation and cell cycle [In Process Citation], Oncogene, 2000, 19:4764–4772.
Luo et al., Cancer predisposition caused by elevated mitotic recombination in bloom mice, Nat. Genet., 2000, 26:424–429.
Wu et al., Genetic recombination: Helicases and topoisomerases link up, Curr. Biol., 1999, 9:R518–520.
Yankiwski et al., Nuclear structure in normal and Bloom syndrome cells, Proc. Natl. Acad. Sci. U. S. A. , 2000, 97:5214–5219.

* cited by examiner

*Primary Examiner*—Sean McGarry
(74) *Attorney, Agent, or Firm*—Licata & Tyrrell P.C.

(57) ABSTRACT

Antisense compounds, compositions and methods are provided for modulating the expression of RECQL2. The compositions comprise antisense compounds, particularly antisense oligonucleotides, targeted to nucleic acids encoding RECQL2. Methods of using these compounds for modulation of RECQL2 expression and for treatment of diseases associated with expression of RECQL2 are provided.

26 Claims, No Drawings

SEQUENCE LISTING

<160> NUMBER OF SEQ ID NOS: 89

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                        20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                        20

<210> SEQ ID NO 3
<211> LENGTH: 4437
<212> TYPE: DNA
<213> ORGANISM: Homo sapiens
<220> FEATURE:
<221> NAME/KEY: CDS
<222> LOCATION: (75)...(4328)

<400> SEQUENCE: 3

```
gcgcggcggc cgtggttgcg gcgcgggaag tttggatcct ggttccgtcc g ctaggagtc      60 tgcgtgcgag gatt atg gct gct gtt cct caa aat aat cta cag gag caa        110
              Met Ala Ala Val Pro Gln Asn Asn Leu Gln Glu G ln
                1               5                   10 cta gaa cgt cac tca gcc aga aca ctt aat a at aaa tta agt ctt tca       158
Leu Glu Arg His Ser Ala Arg Thr Leu Asn A sn Lys Leu Ser Leu Ser
        15                  20                  25 aaa cca aaa ttt tca ggt ttc act ttt aaa a ag aaa aca tct tca gat       206
Lys Pro Lys Phe Ser Gly Phe Thr Phe Lys L ys Lys Thr Ser Ser Asp
 30                  35                      40 aac aat gta tct gta act aat gtg tca gta g ca aaa aca cct gta tta      254
Asn Asn Val Ser Val Thr Asn Val Ser Val A la Lys Thr Pro Val Leu
 45                  50                  55                  60 aga aat aaa gat gtt aat gtt acc gaa gac t tt tcc ttc agt gaa cct      302
Arg Asn Lys Asp Val Asn Val Thr Glu Asp P he Ser Phe Ser Glu Pro
                 65                  70                  75 cta ccc aac acc aca aat cag caa agg gtc a ag gac ttc ttt aaa aat      350
Leu Pro Asn Thr Thr Asn Gln Gln Arg Val L ys Asp Phe Phe Lys Asn
             80                  85                      90 gct cca gca gga cag gaa aca cag aga ggt g ga tca aaa tca tta ttg      398
Ala Pro Ala Gly Gln Glu Thr Gln Arg Gly G ly Ser Lys Ser Leu Leu
         95                  100                 105 cca gat ttc ttg cag act ccg aag gaa gtt g ta tgc act acc caa aac      446
Pro Asp Phe Leu Gln Thr Pro Lys Glu Val V al Cys Thr Thr Gln Asn
     110                 115                 120 aca cca act gta aag aaa tcc cgg gat act g ct ctc aag aaa tta gaa      494
Thr Pro Thr Val Lys Lys Ser Arg Asp Thr A la Leu Lys Lys Leu Glu
125                 130                 135                 140 ttt agt tct tca cca gat tct tta agt acc a tc aat gat tgg gat gat      542
Phe Ser Ser Ser Pro Asp Ser Leu Ser Thr I le Asn Asp Trp Asp Asp
```

```
                145                 150                 155
atg gat gac ttt gat act tct gag act tca a aa tca ttt gtt aca cca      590
Met Asp Asp Phe Asp Thr Ser Glu Thr Ser L ys Ser Phe Val Thr Pro
            160                 165                 170 ccc caa agt cac ttt gta aga gta agc act g ct cag aaa tca aaa aag      638
Pro Gln Ser His Phe Val Arg Val Ser Thr A la Gln Lys Ser Lys Lys
            175                 180                 185 ggt aag aga aac ttt ttt aaa gca cag ctt t at aca aca aac aca gta      686
Gly Lys Arg Asn Phe Phe Lys Ala Gln Leu T yr Thr Thr Asn Thr Val
        190                 195                 200 aag act gat ttg cct cca ccc tcc tct gaa a gc gag caa ata gat ttg      734
Lys Thr Asp Leu Pro Pro Pro Ser Ser Glu S er Glu Gln Ile Asp Leu
205                 210                 215                 220 act gag gaa cag aag gat gac tca gaa tgg t ta agc agc gat gtg att      782
Thr Glu Glu Gln Lys Asp Asp Ser Glu Trp L eu Ser Ser Asp Val Ile
                225                 230                 235 tgc atc gat gat ggc ccc att gct gaa gtg c at ata aat gaa gat gct      830
Cys Ile Asp Asp Gly Pro Ile Ala Glu Val H is Ile Asn Glu Asp Ala
            240                 245                 250 cag gaa agt gac tct ctg aaa act cat ttg g aa gat gaa aga gat aat      878
Gln Glu Ser Asp Ser Leu Lys Thr His Leu G lu Asp Glu Arg Asp Asn
            255                 260                 265 agc gaa aag aag aag aat ttg gaa gaa gct g aa tta cat tca act gag      926
Ser Glu Lys Lys Lys Asn Leu Glu Glu Ala G lu Leu His Ser Thr Glu
        270                 275                 280 aaa gtt cca tgt att gaa ttt gat gat gat g at tat gat acg gat ttt      974
Lys Val Pro Cys Ile Glu Phe Asp Asp Asp A sp Tyr Asp Thr Asp Phe
285                 290                 295                 300 gtt cca cct tct cca gaa gaa att att tct g ct tct tct tcc tct tca     1022
Val Pro Pro Ser Pro Glu Glu Ile Ile Ser A la Ser Ser Ser Ser Ser
                305                 310                 315 aaa tgc ctt agt acg tta aag gac ctt gac a ca tct gac aga aaa gag     1070
Lys Cys Leu Ser Thr Leu Lys Asp Leu Asp T hr Ser Asp Arg Lys Glu
            320                 325                 330 gat gtt ctt agc aca tca aaa gat ctt ttg t ca aaa cct gag aaa atg     1118
Asp Val Leu Ser Thr Ser Lys Asp Leu Leu S er Lys Pro Glu Lys Met
        335                 340                 345 agt atg cag gag ctg aat cca gaa acc agc a ca gac tgt gac gct aga     1166
Ser Met Gln Glu Leu Asn Pro Glu Thr Ser T hr Asp Cys Asp Ala Arg
    350                 355                 360 cag ata agt tta cag cag cag ctt att cat g tg atg gag cac atc tgt     1214
Gln Ile Ser Leu Gln Gln Gln Leu Ile His V al Met Glu His Ile Cys
365                 370                 375                 380 aaa tta att gat act att cct gat gat aaa c tg aaa ctt ttg gat tgt     1262
Lys Leu Ile Asp Thr Ile Pro Asp Asp Lys L eu Lys Leu Leu Asp Cys
                385                 390                 395 ggg aac gaa ctg ctt cag cag cgg aac ata a ga agg aaa ctt cta acg     1310
Gly Asn Glu Leu Leu Gln Gln Arg Asn Ile A rg Arg Lys Leu Leu Thr
            400                 405                 410 gaa gta gat ttt aat aaa agt gat gcc agt c tt ctt ggc tca ttg tgg     1358
Glu Val Asp Phe Asn Lys Ser Asp Ala Ser L eu Leu Gly Ser Leu Trp
            415                 420                 425 aga tac agg cct gat tca ctt gat ggc cct a tg gag ggt gat tcc tgc     1406
Arg Tyr Arg Pro Asp Ser Leu Asp Gly Pro M et Glu Gly Asp Ser Cys
        430                 435                 440 cct aca ggg aat tct atg aag gag tta aat t tt tca cac ctt ccc tca     1454
Pro Thr Gly Asn Ser Met Lys Glu Leu Asn P he Ser His Leu Pro Ser
445                 450                 455                 460 aat tct gtt tct cct ggg gac tgt tta ctg a ct acc acc cta gga aag     1502
```

```
                    -continued

Asn Ser Val Ser Pro Gly Asp Cys Leu Leu Thr Thr Thr Leu Gly Lys
            465                 470                 475 aca gga ttc tct gcc acc agg aag aat ctt ttt gaa agg cct tta ttc   1550
Thr Gly Phe Ser Ala Thr Arg Lys Asn Leu Phe Glu Arg Pro Leu Phe
            480                 485                 490 aat acc cat tta cag aag tcc ttt gta agt agc aac tgg gct gaa aca   1598
Asn Thr His Leu Gln Lys Ser Phe Val Ser Ser Asn Trp Ala Glu Thr
            495                 500                 505 cca aga cta gga aaa aaa aat gaa agc tct tat ttc cca gga aat gtt   1646
Pro Arg Leu Gly Lys Lys Asn Glu Ser Ser Tyr Phe Pro Gly Asn Val
510             515                 520 ctc aca agc act gct gtg aaa gat cag aat aaa cat act gct tca ata   1694
Leu Thr Ser Thr Ala Val Lys Asp Gln Asn Lys His Thr Ala Ser Ile
525             530                 535                 540 aat gac tta gaa aga gaa acc caa cct tcc tat gat att gat aat ttt   1742
Asn Asp Leu Glu Arg Glu Thr Gln Pro Ser Tyr Asp Ile Asp Asn Phe
            545                 550                 555 gac ata gat gac ttt gat gat gat gat gac tgg gaa gac ata atg cat   1790
Asp Ile Asp Asp Phe Asp Asp Asp Asp Asp Trp Glu Asp Ile Met His
            560                 565                 570 aat tta gca gcc agc aaa tct tcc aca gct gcc tat caa ccc atc aag   1838
Asn Leu Ala Ala Ser Lys Ser Ser Thr Ala Ala Tyr Gln Pro Ile Lys
            575                 580                 585 gaa ggt cgg cca att aaa tca gta tca gaa aga ctt tcc tca gcc aag   1886
Glu Gly Arg Pro Ile Lys Ser Val Ser Glu Arg Leu Ser Ser Ala Lys
            590                 595                 600 aca gac tgt ctt cca gtg tca tct act gct caa aat ata aac ttc tca   1934
Thr Asp Cys Leu Pro Val Ser Ser Thr Ala Gln Asn Ile Asn Phe Ser
605             610                 615                 620 gag tca att cag aat tat act gac aag tca gca caa aat tta gca tcc   1982
Glu Ser Ile Gln Asn Tyr Thr Asp Lys Ser Ala Gln Asn Leu Ala Ser
            625                 630                 635 aga aat ctg aaa cat gag cgt ttc caa agt ctt agt ttt cct cat aca   2030
Arg Asn Leu Lys His Glu Arg Phe Gln Ser Leu Ser Phe Pro His Thr
            640                 645                 650 aag gaa atg atg aag att ttt cat aaa aaa ttt ggc ctg cat aat ttt   2078
Lys Glu Met Met Lys Ile Phe His Lys Lys Phe Gly Leu His Asn Phe
            655                 660                 665 aga act aat cag cta gag gcg atc aat gct gca ctg ctt ggt gaa gac   2126
Arg Thr Asn Gln Leu Glu Ala Ile Asn Ala Ala Leu Leu Gly Glu Asp
            670                 675                 680 tgt ttt atc ctg atg ccg act gga ggt ggt aag agt ttg tgt tac cag   2174
Cys Phe Ile Leu Met Pro Thr Gly Gly Gly Lys Ser Leu Cys Tyr Gln
685             690                 695                 700 ctc cct gcc tgt gtt tct cct ggg gtc act gtt gtc att tct ccc ttg   2222
Leu Pro Ala Cys Val Ser Pro Gly Val Thr Val Val Ile Ser Pro Leu
            705                 710                 715 aga tca ctt atc gta gat caa gtc caa aag ctg act tcc ttg gat att   2270
Arg Ser Leu Ile Val Asp Gln Val Gln Lys Leu Thr Ser Leu Asp Ile
            720                 725                 730 cca gct aca tat ctg aca ggt gat aag act gac tca gaa gct aca aat   2318
Pro Ala Thr Tyr Leu Thr Gly Asp Lys Thr Asp Ser Glu Ala Thr Asn
            735                 740                 745 att tac ctc cag tta tca aaa aaa gac cca atc ata aaa ctt cta tat   2366
Ile Tyr Leu Gln Leu Ser Lys Lys Asp Pro Ile Ile Lys Leu Leu Tyr
            750                 755                 760 gtc act cca gaa aag atc tgt gca agt aac aga ctc att tct act ctg   2414
Val Thr Pro Glu Lys Ile Cys Ala Ser Asn Arg Leu Ile Ser Thr Leu
765             770                 775                 780
```

```
                                                            -continued gag aat ctc tat gag agg aag ctc ttg gca c gt ttt gtt att gat gaa    2462
Glu Asn Leu Tyr Glu Arg Lys Leu Leu Ala A rg Phe Val Ile Asp Glu
            785                 790                 795 gca cat tgt gtc agt cag tgg gga cat gat t tt cgt caa gat tac aaa    2510
Ala His Cys Val Ser Gln Trp Gly His Asp P he Arg Gln Asp Tyr Lys
        800                 805                 810 aga atg aat atg ctt cgc cag aag ttt cct t ct gtt ccg gtg atg gct    2558
Arg Met Asn Met Leu Arg Gln Lys Phe Pro S er Val Pro Val Met Ala
                815                 820                 825 ctt acg gcc aca gct aat ccc agg gta cag a ag gac atc ctg act cag    2606
Leu Thr Ala Thr Ala Asn Pro Arg Val Gln L ys Asp Ile Leu Thr Gln
        830                 835                 840 ctg aag att ctc aga cct cag gtg ttt agc a tg agc ttt aac aga cat    2654
Leu Lys Ile Leu Arg Pro Gln Val Phe Ser M et Ser Phe Asn Arg His
845                 850                 855                 860 aat ctg aaa tac tat gta tta ccg aaa aag c ct aaa aag gtg gca ttt    2702
Asn Leu Lys Tyr Tyr Val Leu Pro Lys Lys P ro Lys Lys Val Ala Phe
            865                 870                 875 gat tgc cta gaa tgg atc aga aag cac cac c ca tat gat tca ggg ata    2750
Asp Cys Leu Glu Trp Ile Arg Lys His His P ro Tyr Asp Ser Gly Ile
        880                 885                 890 att tac tgc ctc tcc agg cga gaa tgt gac a cc atg gct gac acg tta    2798
Ile Tyr Cys Leu Ser Arg Arg Glu Cys Asp T hr Met Ala Asp Thr Leu
                895                 900                 905 cag aga gat ggg ctc gct gct ctt gct tac c at gct ggc ctc agt gat    2846
Gln Arg Asp Gly Leu Ala Ala Leu Ala Tyr H is Ala Gly Leu Ser Asp
        910                 915                 920 tct gcc aga gat gaa gtg cag cag aag tgg a tt aat cag gat ggc tgt    2894
Ser Ala Arg Asp Glu Val Gln Gln Lys Trp I le Asn Gln Asp Gly Cys
925                 930                 935                 940 cag gtt atc tgt gct aca att gca ttt gga a tg ggg att gac aaa ccg    2942
Gln Val Ile Cys Ala Thr Ile Ala Phe Gly M et Gly Ile Asp Lys Pro
            945                 950                 955 gac gtg cga ttt gtg att cat gca tct ctc c ct aaa tct gtg gag ggt    2990
Asp Val Arg Phe Val Ile His Ala Ser Leu P ro Lys Ser Val Glu Gly
        960                 965                 970 tac tac caa gaa tct ggc aga gct gga aga g at ggg gaa ata tct cac    3038
Tyr Tyr Gln Glu Ser Gly Arg Ala Gly Arg A sp Gly Glu Ile Ser His
            975                 980                 985 tgc ctg ctt ttc tat acc tat cat gat gtg a cc aga ctg aaa aga ctt    3086
Cys Leu Leu Phe Tyr Thr Tyr His Asp Val T hr Arg Leu Lys Arg Leu
        990                 995                 1000 ata atg atg gaa aaa gat gga aac cat cat a ca aga gaa act cac ttc    3134
Ile Met Met Glu Lys Asp Gly Asn His His T hr Arg Glu Thr His Phe
1005                1010                1015                1020 aat aat ttg tat agc atg gta cat tac tgt g aa aat ata acg gaa tgc    3182
Asn Asn Leu Tyr Ser Met Val His Tyr Cys G lu Asn Ile Thr Glu Cys
            1025                1030                1035 agg aga ata cag ctt ttg gcc tac ttt ggt g aa aat gga ttt aat cct    3230
Arg Arg Ile Gln Leu Leu Ala Tyr Phe Gly G lu Asn Gly Phe Asn Pro
        1040                1045                1050 gat ttt tgt aag aaa cac cca gat gtt tct t gt gat aat tgc tgt aaa    3278
Asp Phe Cys Lys Lys His Pro Asp Val Ser C ys Asp Asn Cys Cys Lys
        1055                1060                1065 aca aag gat tat aaa aca aga gat gtg act g ac gat gtg aaa agt att    3326
Thr Lys Asp Tyr Lys Thr Arg Asp Val Thr A sp Asp Val Lys Ser Ile
        1070                1075                1080 gta aga ttt gtt caa gaa cat agt tca tca c aa gga atg aga aat ata    3374
Val Arg Phe Val Gln Glu His Ser Ser Ser G ln Gly Met Arg Asn Ile
1085                109 0                1095                1100
```

-continued

| | |
|---|---|
| aaa cat gta ggt cct tct gga aga ttt act a tg aat atg ctg gtc gac<br>Lys His Val Gly Pro Ser Gly Arg Phe Thr M et Asn Met Leu Val Asp<br>　　　　　　　1105　　　　　　　　1110　　　　　　　　1115 | 3422 |
| att ttc ttg ggg agt aag agt gca aaa atc c ag tca ggt ata ttt gga<br>Ile Phe Leu Gly Ser Lys Ser Ala Lys Ile G ln Ser Gly Ile Phe Gly<br>　　　　　1120　　　　　　　　1125　　　　　　　　1130 | 3470 |
| aaa gga tct gct tat tca cga cac aat gcc g aa aga ctt ttt aaa aag<br>Lys Gly Ser Ala Tyr Ser Arg His Asn Ala G lu Arg Leu Phe Lys Lys<br>　　　　　1135　　　　　　　　1140　　　　　　　　1145 | 3518 |
| ctg ata ctt gac aag att ttg gat gaa gac t ta tat atc aat gcc aat<br>Leu Ile Leu Asp Lys Ile Leu Asp Glu Asp L eu Tyr Ile Asn Ala Asn<br>　　　　　1150　　　　　　　　1155　　　　　　　　1160 | 3566 |
| gac cag gcg atc gct tat gtg atg ctc gga a at aaa gcc caa act gta<br>Asp Gln Ala Ile Ala Tyr Val Met Leu Gly A sn Lys Ala Gln Thr Val<br>1165　　　　　　　　117 0　　　　　　　　1175　　　　　　　　1180 | 3614 |
| cta aat ggc aat tta aag gta gac ttt atg g aa aca gaa aat tcc agc<br>Leu Asn Gly Asn Leu Lys Val Asp Phe Met G lu Thr Glu Asn Ser Ser<br>　　　　　1185　　　　　　　　1190　　　　　　　　1195 | 3662 |
| agt gtg aaa aaa caa aaa gcg tta gta gca a aa gtg tct cag agg gaa<br>Ser Val Lys Lys Gln Lys Ala Leu Val Ala L ys Val Ser Gln Arg Glu<br>　　　　　1200　　　　　　　　1205　　　　　　　　1210 | 3710 |
| gag atg gtt aaa aaa tgt ctt gga gaa ctt a ca gaa gtc tgc aaa tct<br>Glu Met Val Lys Lys Cys Leu Gly Glu Leu T hr Glu Val Cys Lys Ser<br>　　　　　1215　　　　　　　　1220　　　　　　　　1225 | 3758 |
| ctg ggg aaa gtt ttt ggt gtc cat tac ttc a at att ttt aat acc gtc<br>Leu Gly Lys Val Phe Gly Val His Tyr Phe A sn Ile Phe Asn Thr Val<br>　　　　　1230　　　　　　　　1235　　　　　　　　1240 | 3806 |
| act ctc aag aag ctt gca gaa tct tta tct t ct gat cct gag gtt ttg<br>Thr Leu Lys Lys Leu Ala Glu Ser Leu Ser S er Asp Pro Glu Val Leu<br>1245　　　　　　　　125 0　　　　　　　　1255　　　　　　　　1260 | 3854 |
| ctt caa att gat ggt gtt act gaa gac aaa c tg gaa aaa tat ggt gcg<br>Leu Gln Ile Asp Gly Val Thr Glu Asp Lys L eu Glu Lys Tyr Gly Ala<br>　　　　　1265　　　　　　　　1270　　　　　　　　1275 | 3902 |
| gaa gtg att tca gta tta cag aaa tac tct g aa tgg aca tcg cca gct<br>Glu Val Ile Ser Val Leu Gln Lys Tyr Ser G lu Trp Thr Ser Pro Ala<br>　　　　　1280　　　　　　　　1285　　　　　　　　1290 | 3950 |
| gaa gac agt tcc cca ggg ata agc ctg tcc a gc agc aga ggc ccc gga<br>Glu Asp Ser Ser Pro Gly Ile Ser Leu Ser S er Ser Arg Gly Pro Gly<br>　　　　　1295　　　　　　　　1300　　　　　　　　1305 | 3998 |
| aga agt gcc gct gag gag ctt gac gag gaa a ta ccc gta tct tcc cac<br>Arg Ser Ala Ala Glu Glu Leu Asp Glu Glu I le Pro Val Ser Ser His<br>　　　　　1310　　　　　　　　1315　　　　　　　　1320 | 4046 |
| tac ttt gca agt aaa acc aga aat gaa agg a ag agg aaa aag atg cca<br>Tyr Phe Ala Ser Lys Thr Arg Asn Glu Arg L ys Arg Lys Lys Met Pro<br>1325　　　　　　　　133 0　　　　　　　　1335　　　　　　　　1340 | 4094 |
| gcc tcc caa agg tct aag agg aga aaa act g ct tcc agt ggt tcc aag<br>Ala Ser Gln Arg Ser Lys Arg Arg Lys Thr A la Ser Ser Gly Ser Lys<br>　　　　　1345　　　　　　　　1350　　　　　　　　1355 | 4142 |
| gca aag ggg ggg tct gcc aca tgt aga aag a ta tct tcc aaa acg aaa<br>Ala Lys Gly Gly Ser Ala Thr Cys Arg Lys I le Ser Ser Lys Thr Lys<br>　　　　　1360　　　　　　　　1365　　　　　　　　1370 | 4190 |
| tcc tcc agc atc att gga tcc agt tca gcc t ca cat act tct caa gcg<br>Ser Ser Ser Ile Ile Gly Ser Ser Ser Ala S er His Thr Ser Gln Ala<br>　　　　　1375　　　　　　　　1380　　　　　　　　1385 | 4238 |
| aca tca gga gcc aat agc aaa ttg ggg att a tg gct cca ccg aag cct<br>Thr Ser Gly Ala Asn Ser Lys Leu Gly Ile M et Ala Pro Pro Lys Pro<br>　　　　　1390　　　　　　　　1395　　　　　　　　1400 | 4286 |
| ata aat aga ccg ttt ctt aag cct tca tat g ca ttc tca taa caaccgaatc<br>Ile Asn Arg Pro Phe Leu Lys Pro Ser Tyr A la Phe Ser | 4338 |

```
                1405              141 0              1415
     tcaatgtaca tagaccctct ttcttgtttg tcagcatctg accatctgtg a ctataaagc    4398 tgttattctt gttataccaa aaaaaaaaaa aaaaaaaa                             4437
```

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
gctgcactgc ttggtgaaga                                              20

<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
acacaggcag ggagctggta                                              20

<210> SEQ ID NO 6
<211> LENGTH: 28
<212> TYPE: DNA
<213> ORGANISM: Artificial Sequence
<220> FEATURE:
<223> OTHER INFORMATION: PCR Probe

<400> SEQUENCE: 6
cacctccagt cggcatcagg ataaaaca                                     28

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                               19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                              20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                              20

```
<210> SEQ ID NO 10
<211> LENGTH: 99500
<212> TYPE: DNA
<213> ORGANISM: Homo sapiens
<220> FEATURE:

<400> SEQUENCE: 10
gccaaaaggt gggaataacc aagcatccat ttatatggat gaatggataa a caaaatgta      60
gtatacatgt ataatggaat attatttagc ctcaagaagg aagaaattct g atacatgct    120
acaacataga tgctccttga agacattatg ctaagtgaaa taagccaatc a gaaaagagc    180
aattattgta tgattcaatt tatatgcggt acctcgcact tacagacaga a agtgcaata    240
tcggctataa ggggttgtga gaaacgggta acggggagtt actgtgtaac a ggcagattt    300
tctatttggg ataatgaaaa agttctggag atggatagtg gtgatggttt c acaacaatg    360
tgaatgtact taatgccagt gaactgtaca cttaaaaatg gtgaatttta t gttagatag    420
attttatcac acacacaaag aggagggagg gcgggaggga aggagagagg g aaggaagta    480
gagaggggag aagagaggaa gaaagaaag aagtaagat ctggcatcac a gggcccaca     540
ttcccgcgtg tcagcaatag gctgaaacag aagcatggtt tctcacgtgt c catggaggc    600
atctgagtgt gtgcccactt tcccggttca atgacaattt gcacctgctc g tgtagaggg    660
gtacgggtga aacagagacc agtattatta aggggatgga gaggagagac c gccaaaaca    720
tcgcagagac acaccgtcgg agccaagaga atggggtgca gacgcctggc t tggcctgtg    780
ggaactggca agtctcagct ctcaaacgcc cgggcttttc aacccgccac a gccgggttc    840
cagctgccta cttcctttaa agccttcacc gactctaaaa caccaaaaac a aagacccaa    900
ctagctccga agcccgaga tgtaaccgta gtcatctgac cctcccgtcc g gactctgat    960
tgggctttgg agatacgcgt ccctcccggc gctgtacggc gaccccgccc c agcagcctg   1020
aggggcgggg aacagatgtc cgagtgcgac agtattggtc ggcttcccca g gaagcagcc   1080
aatcggaata ggcaagcttc cggcgggaag tgagccaggg cttggcgcgg c ggccgtggt   1140
tgcggcgcgg gaagtttgga tcctggttcc gtccgctagg agtctgcgtg c gaggtgagt   1200
accgcgcgcg taactacggg tcggtccgca ttgatctagc cctgctctgg c ggcccggcc   1260
cggagctgga ggccgctcgg gttcttccgt ttcctgcact ggttcgcctc g gccgctga    1320
gtcctctagt ctggccaaca tcctgggagg acagcagata cataaatacg t tcccaaatg   1380
gggaaacaga ggcccggggc gggggcgaac tctgccaagg tctcccgggg c gtcggaggc   1440
cgagcatggg ctaggacctg gcatgttgtt gcccatatac tccagtgcgt a acatgatgc   1500
cctgcacaga gtaatcccag cccagacctc tggcactact acctccgtgt c cctcctgag   1560
gaacaacgaa aacactttgt acttttttctg tggccttcca taatcacgag c tgggctact   1620
cttgtttttg agtgtctact gtgtgccatg ttcctggcac ccttgatctt a caactgtag   1680
ctttacgata tcccagcaaa gcgaagtgct taagaatact gcatcagatt g cttgggttc   1740
gaattctggc tccttcacat ttagctctgt gtctactgca cgttactgaa a cactaagtg   1800
tcttggtttt cgtctgtcat atgggggaaa tggtctcttc tacttcctgg c gttttttgtt   1860
aggattaaac gacttaatat atgcaataat aaatgcttcg aaggctacct g ttacatagt   1920
acacagtaag ggttctgtta tcattaccca gagaagcgga tgaaattgtc c cattttag    1980
acatggagaa tctgaagtac aaagaggttg tctccgtaca gaaagagcat t tggtgatta   2040
agtgctagag atacaggatt tgaactaagc gcctgatttt aaagtatgtc c cacaacatt   2100
aggctttctc ctatagccct cacctgtcct taggtcacac agaactttag g tacctcatg   2160
```

```
gcgtgagatg gagcaggtga ctgacagctc cttgtgccac ccatgcagat a aataacact   2220 ggtgtgtcac tgtcaagatt aagggacagg aattcgagag actgcatgag a gatcagaag   2280 atgaagaagc gggtaggcaa aagtattctg tttggggaat agtaaataga a ttaattaaa   2340 tcaacatttt gttagctggg ctgcttatac tgtcagacag tagcttataa t ctactggga   2400 agaaatgaaa tttctgggtc ctgtgtcact ttcaatgcca ctcaccatga c aggtacctt   2460 ataagtatag tttacagtcc tatcagtaac ctggagaagt agttatttcc t tcgttttac   2520 tgaggaaacc aagagttaaa aaatcaggaa aagtgttaga tgtgcagtag a acatcatca   2580 tgctgggaag ttctacacat ccgcttcagg acaggtggta ttacctatga g caggaaggg   2640 aagggaaaaa ggtaagggga atgagtgata gtttattgtt ttgatttta a attttatc   2700 tgttttttcc tttttcatag tcattcctgg aatgagtgag tttgttttg t ttttgtttt   2760 tgggggatga gtctcgctc tgtcgcccag gctggagtgc agtggcgcga t cttggctca   2820 ctgcaagctc cgcctcccgg gttcatgcca ttctcctgcc tcagcctccc a aatagctgg   2880 gactacaggc acccaccacc acgcccagct aattttttgt attttttagta g agacgggt   2940 ttcactgtgt tagccaggat ggtctcgatc tcctgacctc gtgatccgcc t gcctccgcc   3000 tcccaaggtg ctgggattac aggcgagcca ccgcgcccgg ccatgagtga g attttaaat   3060 atatctgaaa tgaggccagg cacagtggct cacacccata atcccagcac t ttgggagga   3120 tgaggcgggc gaatcacctg aggccaggag ttcgagactt gcctcaccaa c atggcgaaa   3180 ctccctctct atagtaaata caaaattatc tgggcgtggt ggtgtgcgcc t gtggttcta   3240 gctactgggg aggctgaggc acgagaatcg cttgaaccca ggaggctgca g ttagtcaag   3300 attgcaccac tgcactccag cctgggtgac agagtgagag tccgtcagtc a atctacctg   3360 aaatgtttta tgccttttaaa agagagagaa tagggccgag tttaactttt t aaatttggt   3420 tggtgggtac atgggtgtaa ttctattttc tgtatcttta tgtaagaaat a ttaaaaatt   3480 aaaagatata catatatatt ttaatttaca tatatatgtg ttttttttcta a gagaaaaat   3540 ggatagaata aagaggtcca agataatcgt agaataatcc taggacttca g tgctgaaag   3600 cccctaaggg tctccactac ctgtaggata aaatctaaac tccttggcat g ataccagag   3660 gcttttgagc attctgtatc gctaacacat actattctac ctcagccttt g taccactag   3720 ttcatagact actcttcttc acaacctcag tcctgtctgt aaagttccac t tgtccttca   3780 atatccaatt cagtgttctt tgaaaagctt ctctatcatt tgcctgtttt t ccttaatct   3840 gggaagccat agtcttttaa gaaaagactt gattgtcaga cttatctcgt t gcattgtaa   3900 ttatttgttg acatgtctat tttctgctag tctataagct ccttgaaggc a gtaataatg   3960 tctttcccat ctctgtactt cagtgcctac catgatgcct ggcacagagt a gtcactgta   4020 gatattagct gaatgaaaaa tacaagttga agacagagag tgaaagttct t ggagttatg   4080 acatatggac tttgttctct ggaatgacag ggaactattg agtttacttt c tttaaaaat   4140 tcccgtattt tattgaaaca tattctcaat gtcaagaaaa atattccagt c ataatccta   4200 tctttcaaac acttgaacta ttttttatttt ccatgagtcc tttccaaatt t cagctataa   4260 aattagttat acagatttag ctatacagat ttcttaggta gctgtagcct t aatgtattc   4320 ataacttagt gttttctttt ttctttctt tttaaacctg acacttgagg a attttttt   4380 ttcttttctt tttttttgag atagggctca ctgcagctcc agcctcccgg g ctcaagtga   4440 tcctcccacc tcagctggga gtacagggt gtaccaccat gcctggctaa t tcttgtatt   4500
```

-continued

```
tgttgtagag atgggctttt gattttttgt agagataggg tctcgccgtg t tgttcaggc      4560
tgatctcgaa ctcgtaggct caagcagttt gcccacggag tgctgggact a caggtttga      4620
gcccaccgca cctggcctgc ttttttcaat attaaattat ttcctggctg g gcgcggtag      4680
cacatgccta tgatcccagc actttgggaa gccaaggttg gggattgctt g agcctggga      4740
gttcaagacc agcctgggca acatggcaaa accccgtctc taccaaaaaa t aaaataaaa      4800
atctaaataa attatttatt ttagtgaatc agtctttatg cttgtcattt g tcttataaa      4860
ttttcgcaat attcctctct ctttggttta ataggtatga aatgatgctc c atgttatta      4920
ttagaaaaat ttcacaattt tttcataaat ttacttagtg tctgtatatt c tggtgagct      4980
gttgtgttta tattccctga acatttgttc actggaactg gatgttcttt a tgtgttttt      5040
aatattaatc atttatctgt tatttgttgc taattttttct tttctttttt c tttttttga      5100
gatggagtct catcctgttg ctgaggctga agtgcagtgg cgtgatctca g ctcactgta      5160
acctccgtct cccgagttca atccattctc ctgcctcagc ctcctgggta g ctgggatta      5220
caggcacccg ccaccacgcc cggctaattt ttgtattttt ggtacagatg g gtttcacc      5280
atgtcaggct ggtctcaaac tcctgacctt aggtgatcta cccactttgg c ttcccaaag      5340
tgctgggatt acaggtgtga gccactgcat ccagcctaat ttttctttta a aaatatttt      5400
tattggccgg gcacagtggc tcgcgcctgt aatcccagca ctttgggagg c ctaggtggg      5460
cggatcatga ggtcaggagt tcgagaccag tgtggccaac atgatgaaac c ctgtgtcta      5520
ctaaaaatac aaaaatcagc tgagcatggt ggcacatgcc tgtaatccca g ctacttggg      5580
aggctgaggc aggagaatca cttgaaccca ggaggcagag attgcagtga g ccgagatca      5640
caccactcca ctccagcctg gcgacagagc aagactgcat ctcaaaaaa a aaaatttt      5700
ctttattatg acaaccaaga tacatttgta aaaatataca taatttcgct g gaaaccaag      5760
agttaaagtg ctcacgcctg taatcccagc actttaggag gctgaggcag g tggatcact      5820
taagggcagg agttcgagac cagcctggcc aacagggtga acccccatct c tttttttt      5880
gagacagagt ctcactctct ctcccagtct ggagtgcagt ggcgcaatct t ggctcactg      5940
aaagctccgc ctcccagctt catgccattc tcctgcctca gcctcccaag t agctgggac      6000
tacaggcacc tgccaccagg cccggctaat ttttgtatt tttagtagag a ccgggtttc      6060
actgtgttag ccaggatggt ctcgatctcc tgacctcatg atccacccac c tcggcctcc      6120
caaagtgctg ggattacagg catgagccgc cgtgcccagc aaaagcccca t ctctactaa      6180
aatacaaaaa ttagctggcc atggtggccc atgtctgtaa tcccagctac t tgtgaagct      6240
gaggcaggag aatcacttga acctgggcag cggaggttgc agtgagccta g atcaggatc      6300
acgccattgc actccagcct gggcaacaga atgagactct gtctcaaaaa a ataaaataa      6360
tttaaaaaaa gttacataat ttaaagaata gttacaaaga aattacaaag t ttagttatg      6420
cataaaaatt atattgtatt catggtaaat tgaagactca ttataaaatt a tagttacac      6480
ataactatca tctagatcaa gaaagaaata gaatattacc aggatcccag g accccagaa      6540
gtgtatcttt ctgatacctc ctccctatgt tagggataac tattgtccca a ttatgtatt      6600
tatttatttt gagacggagt tttgctcttg ttgcccattc tggagtgcag t ggcgcgatc      6660
tcggctcact gcaacctctg cttcctgggt tcaagcaatt ctcctgcctc a gcctcccaa      6720
gtagcttgga ttacaggcgc ctgccaccat ggctggctaa ttttttctat t tttagtaga      6780
gacggggtta tcatcatgttg gccaggctgg tcttaaactc ctgacctcag g taatctgcc      6840
tgcctcggcc tcccaaagtg ctgggattac aggcatgagc caccgctcct g gccctattg      6900
```

```
tcccaattttt tgtgataatg cttttcttgt cttcatagtt tgccctgatc t atacatcta    6960 taaataatat agctcagttt tgcctggttt tgagctctgt aaatgggata a tactatatg    7020 cattctactg agtctttcta gtttgcgtta ttatgtttgt gagattcttc c acgttgtag    7080 atatagttt tctttttcttt tttttttttt ttaatagtaa ttttggctgg g catggtagc    7140 tcacttctgt aatcccagca ctttgggagg ctgaggaagc aagatctctt g aggccagga    7200 gttcaagacc agtctggcaa caatgggaga cttgtctcta taaaaaattt a aaaaattag    7260 ttgagcatga tgtcatgcac ctgtagttcc agattctcca gaggctgagg c aggaggatc    7320 acttgagctt aggagtctga ggctgcagtg aactatgatt gtgccactgc g ctctagcct    7380 gagtgacaga gcaagacctt gtctctaaaa aaaattttt ttaaattgtt t ttcttaacc    7440 tcttaacaga gttttacatg tatagtacca cacagccaca atgttgtatg g cagatctct    7500 agaatgcgtt catttttgcat tactgaaact ttatacttttt tgattaacaa c tcccatttt    7560 cctgaaagcc cctaccctgg caaccactgt gcccctcttt gcttctatga g tttgcctat    7620 tttagatacc tcgttgcagt ggaatcatgt agtatttgtc ctgtgactgg c ttacttcac    7680 tttgcttaat ggcttcaagg ttcatctgtg tcatctcatg ttgcaggatt t ttttttttaa    7740 tttttttatta tttaacttaa ttgtattgta tttattatt tttcagacag g gtcttgctc    7800 agctatccag gctggagtgc agtagaatga tcgttgctca ctgcagcctc t aactcctgg    7860 gctcagatga tccttctgcc tcagcctccc gagaaggtga gactacagga g tgtaccacc    7920 atgcttggct aactttttta tttttttgtag atactgggtc ttgctttgtt g cctaggctg    7980 gtctcaaact cctgggctca agcgatactc ctgccttggc ctcccaaagt g ctgggatta    8040 caagcatgag ccacttcatc tagtcaattt ttttctttt aaaggctgaa t atttcattc    8100 tatgcgtata ccactgtaaa gaaaactcca tttcctctct actctgtacc c atataataa    8160 ttcctcactt ctgtcaccaa atgtgtggtg tttttttttcc ccacaatagt t cagttcttt    8220 agcagacact gggtgtccta catttagctc aggtctgaca ctaactgcca g gttgttagtg    8280 cagaccccaa atgttaagtc ctccctgtcc acccgcattc cagaccccccc a cttcagact    8340 acaagcacaa gtggtaagtc ctccacattc agtcacagaa cagtttcctt a ctagattat    8400 cagcttatta taaacaactc agaagcagcc agctggaaga aatacacagg a caaggtatg    8460 tgggaagggg tgtggcactt ccatgccctc tccaggcaca ccagcctccc a ccatctcta    8520 catgttctca ccaacctaga agctccctga gccctatcct tctgggtttt t acgtaggcc    8580 tccttaccta gacatgattg attaaataat tggccattgg tgattaagtc a ctccccagc    8640 cccttttgtcc tacccagagg aagttttgtt ttgttttttg agaaggagtc t cactctgtc    8700 gcccaggctg gagtgcagtg gtatgatctt ggctcactgc aacctctacc a gctgggttc    8760 aagagattct catgtctcag cctactgaat agctgggggtt ataggtgtgc a ccatcatgc    8820 ctggctaatt tttgtatttt tagtagagag agcgttttgc catgttgtcc a ggatggtct    8880 caaactcctg acctcaggtg atctgcccgt ctcggcctcc caaagtgctg g gattacagg    8940 cataagccac cacgcccggc ccccagagga aggttttatt gaattaatta c aaactgata    9000 ggtcaaagag tgtgtatgtt ttaccttact atgtaatact aaattgtttt c aaaagtgct    9060 tgcactccca ccaatgtatt agattttccg ttgctctgca tgctggctaa t actttatat    9120 ttacattttt attttccaat ctggtatatt catgtatagt agtattttct g gtagcattc    9180 atttctctga ttattagtga agatgagtac cctgatgtgt ttatgggcta t ttcctcttt    9240
```

-continued

| | | | | |
|---|---|---|---|---|
| tttacagtcc | ctttttttt | ttttgaggcg | gagtctcact | ctgttgccca g gctggagtg | 9300 |
| cagtggcacc | atctcggctc | actgcaagct | ccgcctcccg | ggttcacgcc a ttcacctgc | 9360 |
| ctcagcctcc | caagtcccaa | gtagctggga | ctacaggcgc | cgccaccat g cccggctaa | 9420 |
| tttttttttt | ttttggatt | gttttagtag | agacggggtt | tcactgtgtt a gccagggtg | 9480 |
| gtctcaatct | cctgacctcg | tgatccaccc | gcctcggcct | cccaaagtgc t gggattaca | 9540 |
| ggcgtgagcc | accgcgccca | gcctacagtc | cctttttttc | tgtcttctct a ttaagttgt | 9600 |
| ctctgtttta | tgtacatata | aacatattta | tatatagtta | tctacatttt t atatatacg | 9660 |
| tacatacaca | tttacatagg | tgtagcagat | atcttctact | ttggctttt a agtggattt | 9720 |
| aacataattt | tagtcaatga | ctttttttat | ttttacattt | ctttaaagtg a cataattgt | 9780 |
| accccaacaa | tttatggggt | acatagtgat | attttgatac | atatactgta t aatgatcag | 9840 |
| atcagggtaa | ttagcatatc | tatcatctta | aaacatttat | catttctttg t gttgggagc | 9900 |
| attcaatatc | ctccttctag | ctatttgaaa | ctgtatagta | cattattgtt a actgtagtc | 9960 |
| atcctgtagt | gctacagaac | accagaactt | attcttccca | tctagctgta a ttttatatt | 10020 |
| cttttctttc | ctttttttga | gatgaagttt | cactcttgtt | gcccaggctg g agtgcaatg | 10080 |
| gcacaatctt | ggctcactgc | aacctctgcc | tcctgggttc | aagcaattct c ctgcctcag | 10140 |
| cctcccaagt | agctaggatt | acaggcatgc | gccaccatgc | ctggctaatt t tgcattttt | 10200 |
| agtagagacg | gggtttctcc | atgttggtca | ggctgatctc | aaactcctga c ctcaggtga | 10260 |
| tccacccacc | tcggcctccc | aaagtgctgg | gattacaggc | atgagccacc a cacccagcc | 10320 |
| aattttgtat | tctttaacaa | atctgccct | acccttccca | gcctccagtg t cctctgttc | 10380 |
| tagattttac | ttctatgaga | gcaacgattt | ttaggttcca | catatgagtg a gaacatatg | 10440 |
| gtgtttaact | ttctgttctt | tattccactt | aacacaatgt | cctcaggttc c atgttgctg | 10500 |
| tgaataacag | gattttattc | tttttatgg | ctgaatagta | ttctgttgta t aaatgtact | 10560 |
| ataattttt | tattcattca | tcgcttgttg | aacaccttgg | ttgattccgt a tcttggcta | 10620 |
| ttgtgaatag | tgctgcagta | agcatggggg | tgcagatgtc | tctttgatat a ctgacatct | 10680 |
| tttcctttgg | ataagtgttc | agtagtgggt | ttgctgaatc | atatggtagg t ctatttgta | 10740 |
| gttatttgag | gaacttccat | actgttctcc | atagtggctg | tactagttta t attctcacc | 10800 |
| atcagtggaa | gtgtaagagt | tctctttct | ctgcatcctc | accagcattt g ttattttct | 10860 |
| gtcttttga | taatagcttt | cttaactggg | gtaggatgat | acttcattgt g ttttgttt | 10920 |
| ttgttttttt | aattttaaa | atttttgta | gagacggagt | cttgctgtgt t gcccaagct | 10980 |
| ggtcctgaac | tcctagcctc | aagcaatcct | cccgcctcag | cctcctaaag t gctaggatt | 11040 |
| caaggcatga | gccactgtgc | ctggccctaa | ttgtggtttt | gatttgcact a ttttttta | 11100 |
| acatcttta | ttgtgaatta | ttgtatgtta | tatttcatag | atataacttg t acgtgaatg | 11160 |
| agctaatata | gtaggcctga | aactgttacc | ttcagaaaag | cctgcttgca a aattggtcc | 11220 |
| ctggctgtgt | ctgagaactt | ggcttttgaa | acctttccta | cactgatcag g ttgttttac | 11280 |
| taatacctgt | tttccttctg | agagtctgaa | attttggtgg | gaggaaggtg c ctaagtgac | 11340 |
| cagccctcaa | taaaacccct | agattcagag | tctctaacca | gcttcttttg g gcagaaaca | 11400 |
| ttgcacacac | atagctgcat | tttcactgag | agaacatgca | ctttctcagg g gttagagag | 11460 |
| cattggaagc | ctgcacgtga | attcctacag | acactacctg | atgtgttttt t tttcccttg | 11520 |
| ctgatctggt | tgtgtatcct | taaagtgttg | atgatataat | aaatgttagc t tgagtaca | 11580 |
| actgtacact | gagtcccatg | agttcttcca | gcaaaatatt | gaacttagct g ttaagttcc | 11640 |

```
tccagaaaaa aaaaaagctg gaattttgat tagaaatgca tcaagttata g atgaatttg   11700 aggagaatta gcatctccat atcgtcttcc aatgtgaatg tggttcatat g attgtttcc   11760 tccctccttg acttctctta acgactttca attttctttt cttttttga g acagggtct   11820 tgctctctca cccaggctag agcaagtggg gcaatcacag cttactgcag c ctcaacctc   11880 ctgggctcag gtgatcctcc cacctcagcc tcctaagtag ctgggaccat a ggcacatgc   11940 caccatgacc aacaaatatt tgtattttg tagagacagg gttttgctgt g ttgcccagg   12000 ctgctctcaa actcctgggc tcaagtgatc tgcccacctt ggcctcccaa a gtgctggga   12060 ttataggcat gagccactgt gcccagccca attttctgaa tagatatcaa g gacataatt   12120 tgttagatgt attttttaggt atatattatt tcctttaaat tttttttgag a cagggtctc   12180 actctgtcac ccagactgaa gtgcagtggc gtgatctcag ctcaccgcaa c caccgcctt   12240 ccaggctcaa gcaatattcc tgcctcagcc tcccgggtag ctgggattat a ggcacgtgc   12300 cactactgcc accacgttca gctaattttt atatatttag tagagacggg g tttcaccat   12360 gttggccagg ctggtctcga actcctgacc tcaaatgatc cacccacctt g gcctcccaa   12420 agtgctgaga ttacaggcat gagccactgc acccggccgg gtatttaaat t tttgatgtc   12480 atcttaaaaa gttttctgac attttatttt ttgtttattg atgatataga a aaacaattt   12540 attttttgtat attgaccttg tctccagcag tcttcctaaa cacactgtct t agttttcta   12600 tagctgctgt aataaattac cataaactta gtggcttaaa acaacataga g gccgggaac   12660 attggctcat gcctgtaatc tcagcagttt gggaggccaa ggtgggagta t cgcgggagc   12720 ccagaaattc gagaccagtc tgggcaacac ggtgagtccc tgtctctgtt t aaaaataac   12780 aataacacac ggtagctcac acctgtaatc ccagcacttt gagaggccga g gcgggcagg   12840 tcacctgagg tcgggagttt gagactagcc tggccaacgt ggcgaaactc c atctctact   12900 aaaaatacaa aaattagcca ggcatggtgg tacgcgcttg taatcccagc t actcaggag   12960 gctgaggtag gagaattgct tgagcccagg agacagaggt tgcagtttgc c gagatcgcg   13020 ccactgtact ccagcctggg caacaagaga gaaactcagt ttcaaaataa a taaataaaa   13080 taaataaaaa caacaacaac atagatttat tatcttatag ttctgtagtt c agaagtctg   13140 aatgggtttc attgggctaa agtcaaggtg ttggcaggct gagttccctt c tggaggctc   13200 aagggcagaa tccatttcct tccccttttc agcttttaga gactattcgt a ttccttgac   13260 tcttggcttt cctcctccat tatcaaagcc agcaactttg agtcctcctg a agttgccat   13320 cttttctggtc tgtcatctta tttcctcttc cacttaaaaa gacacttgtg a ttgcattgg   13380 gtccatctgg ttagtccagg ataatcttcc tatttttaagg tcagcttatt a gcagtctta   13440 attccgtatg acagtaattc accttttgtca tgtaaccaag catattcaca a catccaagg   13500 atcaggatat agacatcttt ggatgggtat gggagatggg gatagtggtg g tggtcacat   13560 tattttgcct cctgcattca cttaagattt ttattttat ttttattttt a tttttgaga   13620 cgaagtctcg ctctatcgcc caggctggag tgcagtggcg tgatctcggc t cactgcaac   13680 ctccgcctcc cgggttcaag cgattctcct gcctcaacct cccaagtagc t gggattaca   13740 ggtacgcgcc accatgacca cctaattttt ttcttatttt ttattttttag t agagacagg   13800 gtttcactat gttggccagg ctgatctcga actcctgacc tcgtgatcca c ccacctcgg   13860 cctcccaaag tgctgggatt acaggcttga gccactgcat ccagccaaga a ttttaataa   13920 tttaatctga agattctttt agatgttcca cacacaaaat tatagccttt g tgaatatta   13980
```

```
atgattttac atctttccag ttaacacgcc ttttatttat tgttcatgat c tactgctct  14040 ggcttggact tccagtatat atctgataaa agtattgata gtgggcattc t ggaattgtt  14100 cctgatctaa aaagaaaagt ttcctaaact tcaccttact gtattctctc t gtcaggtta  14160 tagaagttcc tttctattcc tgtttgataa gagttgtgtt ttttttttgtt g tttatttttt 14220 gaggtggagt cttgctctgc cacccaggct ggagtgcagt ggcgcaatct t ggcccactg  14280 caacttccgc ctcccggttc aagtgattct cctgtctcag cctcccaagt a gctgagact  14340 agaggctgcg tcactgcgcc cagctaattt ttgtattttta ggtagagaca g ggtttcacc 14400 atattggcca gactggtctc gaactcctga ccttgtgatc tgcccgtctc a gcctcccaa  14460 agtgctggga ttacaggtat gagccaccat gcccggcgtg ataagagttt t cattatgaa  14520 tggatttcac tgtgaatgga tgtttgattt tatcatatgc ttattctaga a gtcttgaga  14580 cgatatggtt gttcagcttt aatgttgtgg tgaattatat taattgatttt t taaatgttg  14640 aaccacttct gagtcatttt ttagacaaca caacttggtc tcggtattttt t tattttatt  14700 tatttattta tccttttaga cagggtctca ctctgttacc caggctggag t gcagtggtg  14760 tgacttcagc tcactgcagc cttgatctcc caagtcatcc tcccatctca g cttcccaag  14820 tagctgggac tataggcaag tgtcaccatg cccagttaat ttttataaat t tttgtggag  14880 atgagattta atcacactgc ccaggctggt ctcaatcctg ggctcaagca a tcctcctgc  14940 cttggcctcc aaaagcgctg ggattatagg tgtgagtcat catgcccgtg g ctcttggtg  15000 tattttatac atggctagat ttactttgct aacatattgt ttgggacttt t gcatctaca  15060 tttatgaaaa agaattagcc tggagttttt cactgaggag ttgcccttac a ggacttagt  15120 atcagagtta tgctagcctc acagaatgag ctggggagtt ggttctttct a tattttgga  15180 atcgtttatg taaaactgga atatttttact gccataagtg cttagaagaa c tcacctgcg  15240 ccactctggt cttgatgcta tctttgtggg tagattttttg accatcaata g gacttcttt  15300 aatggttata aggctattag gttttctgtt tatttttgag tgagttttga t aagttaatt  15360 tttaaggaat gtgtccatct catctaaatt ttaaaattta ttgatgcaaa g ttgttcata  15420 acagcctaat gttatctttt aatgtctata gcatatgtaa ttaaatctcg t ctttcaatc  15480 tcttcttttt tgtcttttta cagaacaaac ttggttattt gatcctctct a ttatatatc  15540 tattattttt tactcttaaa aatttttttta aaaatctatt tatttattta t tttgagacc  15600 ggtttatgaa actggctaat ttttgtattt ttggtagaga tgaggttttca c catgttgcc  15660 aaggctggtc ttgaactcct ggcctcaagt gatccacctg ccttggcttc c caaagtgct  15720 gggattacag gcatgagcca atgcgtctga ccctcttctc tttaaaactg c ctcccttct  15780 attttcatca ggcttatttt ttcagtttct tttctaataa ttagggtcat c cattttctt  15840 gtaactactt ctttagttgc atattagata tttttatgtg tagattttcca t tattcagtt  15900 taaagtatat ttgaatactc actatgatat cttacttgac tgatggctta t tcacaagta  15960 tatttcttga ttttcaatac aaagggattt tctagatctc atttttcttta t tttgaaatt  16020 ttaaaaatct acagaaaaga aaacctacag aaaagttgaa gaattagtgc a gtatatcat  16080 cttcccaagt aaacaattta cattcataaa aatagttcat atattaggta a caaggaaaa  16140 cattagtaat ttcataaagt agaaatatta taattctgat caccatgcaa c aaaactaga  16200 aattaaaaat gaaatttata aaaaagcaga aaggcccttc catctggaaa a ttgaaaaca  16260 actattggat gtaaggaaaa cagaaactga aataaaggat ttctgaaaat t aacgaaatg  16320 aaaacacagc atatcagatt cttaaaaaaa aaaaaaaggt aaggcactag t caggggaaa  16380
```

-continued

```
atttataatc ttcagtacat attataaatg aagaagggga aataatgaaa t aaattccaa    16440
acttagaaag ttaggaaaag aaaaacaagt aaatcgaaag cacaagagaa t aaataataa    16500
agataaaaag agaaattagt aagagaacag gaaaacatct gattcaaaaa t taagattttt   16560
tatcttggct gggcgcagtg gctcatgcca gtaatcccag cactttggga g gccgaagca    16620
ggcagatcac gaggtcagga gatcaagact atcctgtcca acacggtgaa a ccccgtctc    16680
tactaaatac aaaaacttag ccaggcgtgg tggcatgcac ctgtaatccc a gctactcgg    16740
gatgctgagg caggagaatt gcttgaacct ggaaggcaga gtttgcagtg a gccgagatc    16800
gtgccactgc actgcagcct gggtgacaga gtgagactat gtctcaaaaa a attaaaaaa    16860
aaaagatgtg tatcttgaat tgtttaatga agcaaataaa ttagcctaat a gaaattaca    16920
aatatacaga ataagaaatg gtaagtggta agtaaccact gacacaggat a gtttttata    16980
acaggattaa tttatgtacc tttacgtaaa caaatttgaa aactaaaatg a aatggataa    17040
ttatgtgtga aaatctagtt taccaaaatt gactcaagta gatgttggaa g ttaaatagc    17100
tcaatttcca ttgaataagt ttttaaagtt atgaaataac tgtctcactg a aaaataaaa    17160
aacatgaggt ccaaatggtt taacaggaaa attctactac atttatggag t ccaaataat    17220
cctaatgcta aataaattgt tttagaacgt agaaaagaag gaaaacttcc a aattcttta    17280
ttttccaaat ggcttggtat tgtaaatgct gatttagttg tctgtctcca g ttgttgaag    17340
ggctgaagtg aaataaagta aaacatctta aaacactttt tagttcttag a ccctctttt    17400
ttaaagtagc tttattgata tagactgcac gtatttaaag tatacaattt g ttcagtttt    17460
gacatacaca catcatcacc ataattcagt taatgaacat atccatcact c tcaaaagtt    17520
tcctcatccc ccttaattct gccttcttgc tctcttcttg ccggtcaacc a cttatctgg    17580
tttctgtcac tgtagaataa ttagcatgtt ctaggacttt taataaatgt t ataatacag    17640
tgtgtattct tttgtatctc acttctttta cacagcataa ttattttata t cggtttta    17700
tgaagcaagt ataaaacaaa tatttaacat aaaaattaaa ggtagcacaa a gaaaattac    17760
agatgaatat tatgtataaa aattatgtaa aagttctaaa taaaatacta c caaacagaa    17820
cagaatccag cactctatta caaaactatt agctcatcac caagatgtat a ccaggaatg    17880
caaagatggt ttaacattag aatcatcaat gtaattcacc atattaatta a cctaaggag    17940
aacagtcata tatttacttt tatatatgct gaaaagcct ttgacaagat t caacaccaa    18000
tatatagtaa aaactcttaa gaattatat tgtaatcaat acttcttttt t ttttttga     18060
gatggagtct caccctgtcg cccaggctga agtacagtag catgacctca g ctcactgca    18120
acctccacct cccaggttca agccattctc ctgcctcagc ctcccaagtc g ctgggatta    18180
caggcgccca ccaccacacc tggctaattt ttgtattttt agtagagatg c ggtttcacc    18240
atcttggcca ggctggtctc aaagtcctga cctcaggtga tctgcccacc t cggcctccc    18300
aaaatgctgg gattacagat gtgagccacc atgcctggcc aatcaatact t cttaatgat    18360
ggtattctct ctctctctct ctgtctctgt ctctcacgca cacatacaca c acacgcgcg    18420
cacgcacgca cacacacaca cacacgcgca gagagagaga gagagagaga g agagagaga    18480
gagagacttt attcctaaat cctgtatttt atctaatagg aaaatactag a ggcatttt     18540
actaagattg agaaaaatat agagatactc accaactcca cttgtattta a cattgtact    18600
gggggcttag ccaatgcagt tagataaatc aattagaggc acaagatttg g aaaataaaa    18660
agtaatattg tccctacttg caggtgatat ggtagtgtgt ctggaatact g cagaaaatc    18720
```

```
aataatgaaa ctaactaaac agaaaaggaa ttttataaga atatgcaaaa a tcagtagtc  18780 ttcatataca caacaagttt gaatatataa tgaagggtaa aatcccattt a cagcaacaa  18840 gaaaagaga aaatatttag gaatttaaaa acatgtaaaa cctaggtgaa g aaatcttta  18900 aaacacttct gaataacaaa aatagcctta acaaatgaa atcttttgtt c taggacagg  18960 acaacaacat cataaaagtg cctaagttaa tatatatata tatatatata t atatatata  19020 tatatatata tatatatatt taagttaata catataccta agttaatata t aaatttaat  19080 gcaatctcaa tataaatatc aacagagttc tggcactaga caagttgatt c taaagttca  19140 tatagaaaaa taaacatata agaataggaa aacagaagag ctacaaagag a aagtagact  19200 tccagatatt gtaacatgtt gcaaagcttc tatcatgata atattgtggt a tagaccaat  19260 ggtatagaat ggaaagtcaa taattagtct cctaaacaca tgaagaattt a gtgtatgat  19320 aaaggtagtt ctgaaattat tagggcagag atggactctt aataaaatag t gctgggaca  19380 acttgttagc cacttgaaaa aacaaaatta tatctatact ttatatcaga c acaggaata  19440 aactccaaat gaaccagaaa tctaattttt tttaaattac ctactagaag a atacataga  19500 tgagttttct gtaacctgga tgtggagaag ggcaataaaa gaggggggaaa a attggctac  19560 attgaaaagc aaattcttga ttacaaaaat gaaaaacacc ataagcaaat t taaaagata  19620 gatgagaaac caggaaaaaa atctgcaaaa tacattttaa agacctacta t ccctagtct  19680 aaattgagag aaaaaaatac taaaatttgg ttaaaaaggc agaatacatg a gcagataca  19740 atttttttaaa aagattcaaa aaccatcctt aaatatgtga agaaaatatt c aatttcacc  19800 taaacaggaa gtgtaaattt aaagctgcac tgaaataccg tttctcacct a tcagctctg  19860 cactaattag aaagcttcac aagaagcccc attggtgagg ctgtgaggaa t gcaaacttg  19920 taaaacctcc tttgagggag aagttggcaa tccagcagac tacacatgca t ttgcccttt  19980 gacccagcca ttccacttgt agaaatattc cctaaagata catttctttt c tttctttc  20040 ctttttttt gagacagggt cttgcttgtt gcccaggctg aagtgcagta g tgtgatctt  20100 ggctcactgc agctcaaact cccaggctca attgatccca ccttggcctc t ggagtagct  20160 gggaccacaa gtgcatgcca ccacgcctta ctaatttaaa aattttttt a tagagacgg  20220 agtctcacca tgttgcccag gctggtcttg aactcctgga ctcaagcaat c ctgtctctg  20280 cctcccaaat tgctgggatg acaggtgtga gccaccgtgc ccggccttac g ttttcaaca  20340 gtagggaaat atgaatgcac aaagttattt gttgcagcat tatttgtaat t gtaaaatat  20400 cagggaatac cttaaatgtc catacaggaa atttgttggt aaatatctac a caatggagt  20460 actgtacagc tgtaaagaag aatgaggaaa atctttgcaa acgggtgtag a gtgatttct  20520 aacatgaatg gaaagcgtac atacagtgtg ctatttttta tgtaagaaag a agggaaaat  20580 atgagactct aatgtctgct tattttgcaa aaagaaaaac aggaaagata a atcagaaat  20640 tattgaaatt gataacccac aggaagtaga tggcaaagga tggagaggga a gaacacttc  20700 tctgtgggga aaaacagtct tttatgtagt tttaactttt agaactatgt a aatgtttta  20760 tatattcaaa aatcaaatcc acaagaacag tacaaacaca aactaatcta a ttcaaatga  20820 tgaatgtaat caccctgaag gtgaggtggg actgaccaat caagtaactt t tgaatatag  20880 tactttaatt atgtaccctt aatctgaaga aagaaatgca actgaattt g aactcttct  20940 tagtaggttt ttttttttta gtgacaggag tgtagcaatt tgaaattact t cctatagtt  21000 tcagattgaa taaatgaata aatatatgat ggttttttct atgaatttta a gatagatgg  21060 atagatcaat ggatgtatag ctgtagatac agaaatagat agaagtgttt a tatttccta  21120
```

-continued

```
gatctgtcta ctaaaagggc ctaggagcaa tgatatgcaa gtagcagatc a tatctaatg   21180 gccaggtctt agattttaaa gattttttcct cattaaaata aatgaaggct g tttgaggaa   21240 atggtgattc tatggctgaa gcaggaaaag taaatgaaga ccatgaatgt t tgtgccaggt  21300 aataagaaag tgcctgatgg gaacacttta aaggacagag gaaccaatgg a ttaaagaag   21360 aaaacaagag acattagagt atatcttgag acaatgaaaa cgaaaacaca a catgccaaa   21420 actcatggaa tacagtgaaa gcagtactag aaaggaaatt tatagctaca a atgcttaca   21480 ttaaaaaaga aagatctgaa atcaacaatt taacttcaca cttaaaggaa c agtaaaaag   21540 aacaaaccaa acccaaagct acagaaacaa ggaaataata aatattaggg c agagataaa   21600 caaaacaggg actagaaaag cagtagagaa attgacaaaa cagaattgat t ctttgaaat   21660 gataaaaaaa ttgataaaac tttagccaga tggactaaga aaaataaga c aaattacta   21720 aaatcagaag tgaacaaggg gacattataa ctgatttaca aagtaaaaa g atttataag   21780 agaatattgt gagcaaatgt atgccaacaa atttgataac ataaatgaaa t ggataaatt   21840 cctcaaaaca cataaccacc aagacagaat catgaagaaa cagaaaatct g aacagacct   21900 ataactagta aggagattga gttagtaatc aggtatcacc caacaaagaa a agctcaggg   21960 ccagatggcc tcactggtca tttctaacca atatttaaag aagaattaag t ccaattttc   22020 ctcaagctct tccaattaat gatatatttg ataaaggttt aatacccagg a tatataaag   22080 aactcctcag cactttggga ggctgccggg acggagaat ttcttgagcc t aggagttgg   22140 agaccagcct aggcaacatg gtgaaaccct ggctctacaa aaaatttaaa a atttgccag   22200 gtgtgatggt actttgctgt ggtcccagct actccgtagg ctgaggtggg a ggaccactt   22260 gagcccggga ggtcgaggca gccgtgagct gttgcactcc agcctgggtg a cagagtgaa   22320 accctgtttc aaaaaacaaa acaaaacaaa acaaaacaaa acaaaacaaa a actcataca   22380 gctcaacaaa taacccattt agaaaataga gaaaggactc gaatagacac t tcaccaaag   22440 aagatataca aatggccaat aagcaaatga aaagatgcct attatcacta a tcattagag   22500 aaaggcaaat caaaaccagg agataagacc tcacacctgt tagaatgcct g ttataaaac   22560 aaaacaacaa ccagaaaata acaagtgttg ctgaggatgt ggagaaatta g gatgtggaa   22620 aaatgggaag ccctgtgcat tatttatagc aatgtgaaat ggtgcaacca c tgtggagaa   22680 cagtgtggtg gttccttaaa aattaaacat aaattaccat atgattcagc a attctcaaa   22740 aagatatttg tacacccatg ttcataacag cattattcac aatagccaaa a ggtggaagc   22800 aaccctaacg tccttgaatg gataagaaaa tgtggtatgt atctacagtt a gatattatt   22860 cagccttaaa aaggaaggag cggccaggcg cggtggctca cacttgtaat c ccagcccctt  22920 tgggaggctg agacaggcag atcacaaggt cacaggttca agaccagcct g gccaacatg   22980 gtgaaacccc gtctctacta aaaatacaaa acagaaaaat tagctgggct t gatggcacg   23040 cacctgtaat cccagctact caggaggctc gggcaggaga atcacttgaa c ccgggaggc   23100 agaggttgca gtgagctgag attgcgccac tgcaccccag cctgggcaac a gagcaagac   23160 tccatctcaa aaatattaa taataataaa ggaaggagcc tggcatggtg a ctcatacct   23220 gtaatcccga ctactccgga ggcagaggtg ggaggatcat tagagctcag g agattgagg   23280 ctgcagcgag ctctgcacac aggaaattct gacacatgtc tcacaacata g ataaagctt   23340 gagaacactg tgctgagtga aataagccag tcccgaaaag gcaaatactg t atgattcca   23400 cttacagtgt gaatacatta tgattcccat actgtatgag tctgctgatg a caaactatt   23460
```

```
gtttttttga taatctggaa gtgtctctat ttcttgtggc attttaaata a cagctgtat    23520 tgttttaaa ttattatttg tttattttt tgagacaggg tcttgctctg t tgcccaggt    23580 tagagtgcag tggtgcaatc acagctcact gcagcctcga cttcctggtt g agcagtcct    23640 cccacctcag cttcccaagt agctgggaca acaggcatgc accatcattc c tggctaatc    23700 ttttgtattt tttgtagaga tggggtttca ccatattgcc caggctggtc t ccaactcct    23760 gggctcaagc gatcccccg cctcagcctt ccaaagggct gggattacag g catgagcta    23820 ctgtgtctgg cctgaatgac aggtctattg aaatacatta cacatataaa a ttcacccat    23880 taaactgtac aatccaatgg ctttgagtat attcacagtt atgcaaccat c accgcaatc    23940 aatgttggaa cattttcatc agcccacaga gaaatttgca tacccttgc c atcatcccc    24000 aaatcctctc atctttccca accctaggca atcagtagtc tacactgtat c catggatat    24060 gtctattctt atacatttca tataaatgga atcatacact agttcatctt t tgtggctgg    24120 attctttcac ttaacataat ggtttcaagg ctcgtcatta ctgtagcatt t atcagtact    24180 atattttttt gtgtggccaa ataacatttt gttgaatgga tatacacatt t tatttatcc    24240 attcatcact tgatggacat ttgagtggtt tctgaatttg gctattgtga a taatgctcc    24300 tgtgaacaat ttgtgtacaa gtatttattt tgagtaccca tttttcactc t ttcgcatat    24360 atagctagga gtgaaattgc tgggttacat ggtgatatgg tttgcctgtg t ccccattga    24420 aatctcatct tgaactgtgg ctcccataat ccccatgtgt catgggaggg a cctcgtggg    24480 aggtaattga atcatgggtt tttcccatgc tgttcttgtg agagtgaata a gtctcacga    24540 gagctgatgg ttttataaaa ggcagttccc ctgcacacac tttcttgcct g ccaccatat    24600 aagatgtgcc tttgccctc ctttgccttc tgccatgatt gtgaggcctc c ccagccatg    24660 tggaactgag tccattaaac ctctttttct ttataaatta cccactctca g gtgtttctt    24720 catagcagta tgaaaatgga ctagaacacg tggtgactat gtttcgtttt t tgaggtact    24780 gcttgactgt tttccaaagt ggctgtgcca ttttagagtc ctaccagcag t gtatgaggg    24840 ttctgatttc cccacattgt tgccaacact tatctgttgc ttttattata g ctacttttt    24900 aaaaataaca gctttattga gatataattc ataccatg aaattcacct t taaaaacct    24960 agtgtacaat tcactgccct tgatttgtga aagatatttt ttctgggaaa a gaattctgg    25020 gttaatttct atcagcacat cgaagatatc attccactgt cttttgattt t cattttgc    25080 taaagagaaa tcaattttt gtccatatgg tacactgata tatttgggtg t ggatttctt    25140 tttatctctg cttggaattt tttggctttc tcaaatctga aggttagtgt c tttaattag    25200 tcctggaaaa gtcccagctg ttatcttttc aaatattaat tcttccctat t ttctcttct    25260 ttctggaact ctggctagat ttatgttaga cttctactc tgtcttccat g tctcctaac    25320 ttctcatatt ttccatctgt tttctctatc tctctgtgtg tgcatctatt a agtcaaaaa    25380 ctatgaaggg tctgagattt taccctacat ttatagctat atttatcttt a gccacttt    25440 ctgaagttct aattatctat tgttatgact gatttttcttt gggttgtatt g gtatattat    25500 caagttgtct acatataatg ataatctcat ctcttctagt attccttttt c gaatattt    25560 ttgcattggc aagagcatcc aatatgggag tgaaatgag agaacaatat t gttttgct    25620 gttgttttta atggattcac ccctagtgta aaatatatgg tatttgttgg t tctagattt    25680 taaacacttg taatttttgtg ttttaatgtg tttgttagac atggtttgag t tttattagg    25740 tgccttttca aaaatgcatt gataatacat actgtgtgat tctatatata t gaatcaaga    25800 agtttaagaa accatgaacg aagagaacat atgacataaa attctgtcaa a aatctctct    25860
```

-continued

```
ttgtctagaa attgtgtttg atgtttaatt ttatcagaga acagaaagtt g cttgcccca    25920 gtgccccagt taaggtaaag ctgaggttca taaatacctc aacttaaaaa a atacaaaaa    25980 gtagatttt  tgatcgttct tagttaggct caccacctt  gccccaggga a agtaactcc    26040 tcccctttga acagtcactg agtgaggctt acagagcgac gctctgtttt t caggaacca    26100 cccccctaaaa tctccacttt tagcagaaga ctggaaacag aaacatctaa a tgttacttg    26160 gcactgaatg tcttggagta gtcttttgg cagtctatcc cttgatagac t gaaatagcc    26220 atctttgaca acaaaatgaa taaaaagtaa ggtttgacct agtcttaatt t tgatagatc    26280 cccaaccagt aacttagtg tcacttattt caaagaaaag gcactctttt t ttctgctgt    26340 gttttctcc atcccatgtc tctctctctc tctcttttt  ttttaaaggt t tattgtgtt    26400 tactttatt  cttttttat ttttgagaca gggtctctgt tgcccaggct g gagtgcagt    26460 ggggtgatca tggctcactg aaacctcgac ctccgggct  caaatgatcc t tcccacctc    26520 agcctcctga gtaactggga ctacaggcat gtgccacctc actcagctaa t ttttgtgtt    26580 tttttgtaga gacaggtcgt actttgttgc ccaggctgct ctgcagctcc t gggctcaag    26640 cgatcctccc gctttggctt cccaaagtgc tagtattaca agtgtgagcc g ccgtgccca    26700 gcctatttga aaaattctta atagccagtt ttaaaggtaa tgcttgaagc t tacatttcc    26760 tgtgactttt ttttttttt  tttttaaaca cagggtctca ctgtcacccc a gctggagca    26820 gtggcacaga attgctcact gcagcctcga actcctgggc tcaagggata c tcccacctc    26880 agcctccctg agtagttggg actgtaggtg tgtgccacca tgcctggcta a agatgggat    26940 ctccctgtgt tgcccaggct agtctcaaac tcctgggctc aagccatccc c ctgcctcag    27000 cctcccaaag tgctgggatt ataggcgtga gccaccgctc ctggcctgct t atttatatt    27060 cttttgtaat ggcatgataa cttctttcat atatgtagga gaaaatttta a tcattttcc    27120 agattgaact tgtgattctt gtggtcattc taattcatag gtttatttt  t tagtttctg    27180 gttgctcatt gcacccagaa attgttcctt tttttaatat tgtgaaactt c actagcctc    27240 aatttatttg ttttcagtta attttctcc tttatcactg gtctttgtta t tgtggatga    27300 acaatttt  ttaagagatg gggtctcaca gtgttgccca ggctatagtg c agtggctgt    27360 ttacaggtgt gatcatagtg cactacagcc ctgaactcct gggctcatgc a atcctcctg    27420 cctcagcctc ctgagtagct gagactacag gcatgttggt gaacaatttt c ttttgtgt    27480 ccaacaattg tatcgatatt ttgatggagt atgtacagaa gagacaccct t atggttctt    27540 agtactcacc aacttcctga aagcattccc actgaggatt tgagtaaga a aattatgta    27600 ctcattacca tacttcagaa tatgattctg gctggagggt gctacctcgt g aggaataac    27660 caaagagcag tgcattttaa aagcaggaag aggtcccctg gagttaaggt t gactgcatg    27720 ctagctgtga atccatagtg taatcactac agttataaaa tagttaatca a acaattgta    27780 ctcctgggat ggctaagtag acatataaaa ccatgctgtg gagtaatgta g gaaatctct    27840 tattaaaata tcatggctag ttttgatcca aaataagta agttatggaa g gaatgtggg    27900 aaaagggtaa gtaatgatgc catagaccac tttgttctgc ttagtgtcat t aagactgaa    27960 gatctgtgta cctctgcctc cttgtcagta gtctactttg ttgatgttga a attcttaga    28020 gggcaatagt ctgacttcac tcttatcac ttcgtattta ttcatgtggg a aagactccc    28080 acattgtaca ggaccttgaa gaggggacgc ctcaacaaaa gatcaaggct t ttattttt     28140 atttatttat ttatttttg agacagagtc tagctctgtc accaggctgg a gtgcagtgg    28200
```

-continued

```
cacaatctcg gttcactgca acctctgcct cccgggttca agcaattatc c tgcctcagc  28260 ttcccaagta actgggatta caggcacatg ccaccatgcc cagctaattt t gtatttta   28320 gtagagacag ggattcacca tattggccag gttggtcttg atctcctgac c tcatgatcc  28380 gcccacctcg gccttccaaa gtgctgggat tacaggcgtg agccaccgtg c ccagccaag  28440 atcaatactt ttaaactgga ttccaaatgg tgaagtgccc taggaaatgc a gagattaag  28500 ggcttaaaat atgctccatt aaaaagaatc agggaggctg ggcgcggtgg c tcacacctg  28560 caatcccagc actttgggag gcggaggcag gaggatccct tgagcacagg a gttcgaggc  28620 cagcctggga aacatggtga aaccccatct ctaccaaaaa tacaaaaaaa t tagtgggc  28680 atggtggtgt gcacctgtgg tccagctgtg tgggagggtg aggtgggagg a cacttgag   28740 ctggggaggc ggaggctgca gtgagtcacc actgcactcc agcctgggca a caaagtgag  28800 accctgtctc aaaaagaaaa agaaaaacaa gaattaggga tgcttgacga a atggccgat  28860 tccaaatctg gtgcaaaaaa atgcataagg tatgcctgga acatcttttg a gaggaaaga  28920 agctctcaat gactcataag gttaagtcat aaggactgaa gagcccgcct g aaaagactc  28980 ccactggcca aacatgaatc aatttgagaa tcaataagga tgatcactgt a ttggattga  29040 aacacaccta atatgtttaa tccatgagtt cataatgata ctgaaaaaaa a ttcatcact  29100 atttgaaggt ggtgaaagaa tgaatatcat tttttattta ttattgttaa t gtatgtaag  29160 ggatacaagt gtagacttct ttttgttgt tttttgaaac agggtcttgc t ctgttgccc   29220 aggctggagt gcagtggcac aatctcagct cactgcaata tctgcctcct a ggctcaagc  29280 agtcctccca cctcagcctc ctgagtagca gggaccacag gcccgcacca c catgccagg  29340 ctaattttt tatagttctt tagagacagg gttttgccat gttgcccagc c tggtctcaa   29400 actcctgggc tcaagcgatc cgctcacctc agcctcctaa agtgctgggt c tatgggcat  29460 gagccactgc tgccagccac gtgaatataa tgtatagtag tgaagtatgg g cttttagtg  29520 tactgcatca ttattttgaa acttacgata aaagtcttac agctgggcta c gcatggctc  29580 acacctgtaa tcctagcact ttgcaggct gaggtgggga aatgacttga g ctcaggagt   29640 tcgagaccag cctagtcaac atggtgagac cctgtcttta ccaaacattt a aaaattagc  29700 tgggttgtgg tagtgtacac ctgtagtccc agataactca ggaagctgag g tgggaggat  29760 cacttgagcc caagaggtcg aggctgcagt gagctgtgat tgagccagtg t actccagcc  29820 tgggcaacag atcaagaccc tgtctcagaa agaaaacaaa caaacaaaaa g tattcctgc  29880 taatgagtga aagaagtaat aacagaatcg aaatgtcacc attttggagg t ggacttcca  29940 aaatggtgga gtaaggacct cagggtgtat gtatagctga aacaatattg g atgagttga  30000 taattgttga atctgggtga taggtatgta gggattcatt ccttccatct a cttttttgg  30060 gggtaataat taagatataa ttcacatgcc agtgtgaatt attcaatgtt t attaaataa  30120 ctagctatat tacctaaagc atgttaaaga gggaaaagaa gcagaaataa t ccttctgg   30180 agaaagtggg acaaaagctg tattatgatc atgcttataa acatgaagat t tctcaattg  30240 gatgtaactt agtttcttct aaattctgat tttcactgtt atctaaagtc a agatggttg  30300 atagatatgg gttaatgagt ggaacacgg ttatgcgaaa cttcatattt c tagaaatat   30360 catctagtgt taaccctgcc tcctaagata tatgctataa aataaaaata g atgtctagt  30420 aaaggtaggg aaaagggttt atggggttat aactatcagc taaagtgagg a ttttttaa   30480 ctatgcatgg attacagcta ggatcttcct ttagccccag taatttaag g tggtttaag   30540 ctgtttgtta tcctgggcta tagctcagcg ttaccacagc ttgttacaca g agatataaa  30600
```

```
tgtgcttggt aaacgtattc tttcaggttg aaactagatg attatgaagc a tagtatctt   30660 gctggtaaac ctttgctctc attggtggtg gtgttcctcc tttccccagt t ctgcccttg   30720 tgcagaattc agttattcat ttgttctttg ggctttccgt gtgctttgat c atttcctcc   30780 cacctcgctc ccttccagct ttcatttatc cttccaggcc aggtcccatt t ttctaaaag   30840 cccttttccta ataatcccct ccctaatgtc ttttgtactt attttagcat t gtggaggaa   30900 gagaggggga acctggttat tctgttattc aagtgagcct tcagttagtt g aagattata   30960 tatttcaagt gtcactagtt gtaaatgtca aaacagtcta ttgaccaaaa a aaaaaaaaa   31020 aaaaaaaaaa aagtcctatt actctgggca cagttggaac aatgcctgtt t gaatcaagt   31080 ccttcctccc ctcaaaaaac attgtgatta atgcaaagta cctaactcca c tgatttctt   31140 tttccctcac tttttaggat tatggctgct gttcctcaaa ataatctaca g gagcaacta   31200 gaacgtcact cagccagaac acttaataat aaattaagtc tttcaaaacc a aaattttcg   31260 taagtgtttt gactggtttg ctgtcacata ggcactaact taccacattg t acacatgag   31320 atatcttctc tttaaactcc cccattgtac agatgaggaa atgaagctga g agattcatt   31380 gattttccca ctttgccaat taatggtaga gtatgtttta gcagcaccag g tgagattgt   31440 gtctcatctt tgcatggttc ctggcacata atatttgctc aataaagatt t gttgagtaa   31500 atgaataatt gatcttgtaa atttgggcaa ataagtgttt tttaagtttt g ggggttttt   31560 tttgtttgtt ttgttttgtt ttgttttttc ttttgagacg gagtctcgct c tgtcgcaca   31620 ggctggagtg cagtggcgcg atcttggctc actgcaagct ccgcctcctg g gttcacgcc   31680 attctcctgc ctcagcctcc cgagtagctg ggactacagg cacctgccac c acgcctggc   31740 taatttttttt ttgtatttttt tagagacggt ttcaccttgt tagccaggat g gtctcgatc   31800 tcctgacctc atgatccacc tgcctcggcc tcccaaagtg ctgggattac a tgcatgagc   31860 caccgtgccc agcctttttt ttttttttctt ttttgagacg gagtttcgct c ttcttgccc   31920 aggctggagt gccatggcac aatcttagct caccgcaacc tccgtcttcc g ggttcaagt   31980 gattctcctg cctcagcctc ccaagtagct gggattacag gcatgcacca c catgcctgg   32040 ctaattttgt attttttagta gagacaggat ttgtccatgt tgggcagact g gtctcaaac   32100 tcctgacctc aagtgatccg cccaccttgg cctcccaaag tgctgggatt a caggcgtga   32160 gccaccacgc ccggccaatt attttaatat aattttatat actttcgaag a acagtttat   32220 aaggaaacta cagctctcca gttctgcctc tcctctaagc tatactccag a ctccttcta   32280 atgatatcta ataataattt atattataag tgatgctttt accaggttgt a gactttgtt   32340 ctgggtgcct ggctttgaag tcaccactga ctttgagatc attaaatcca g cagatagcc   32400 acgattcctg cgtcttttac ttgtcctgca gattttaaca gagttagcag t ttttaactc   32460 tttttccccct ttaagttctt atcagagtag caaaaagtag ccatatttga a tctcttccg   32520 tttttctttt ttcttttttt tttttgaga cagtctcgct ctgtcaccca g gctggagtg   32580 cggcagtata gtctccggctc actgtaacct ccacctcctg ggttcaagct a ttctcctgc   32640 ctcagccttc tgactagcta gggcttcagg catacaccac tatgcccggc t aattttttg   32700 tgtttttatt agaggtgggg tttcaccatg ttggccaggc tggtctcgaa c tcctgacct   32760 caagcattcc acctgcctcg gcctcccaaa gtgctgggat tacaggcatg a gccactgca   32820 cccggcctct tccctttttc atttatgctg tcacccccgct ctgagatgc t attaactaa   32880 ggactactag cctgagaaat aaagtagtgg gaatgacctc tcaaagccaa a taattagcc   32940
```

```
tctgaatggg aaggaccaga gaacgaatac aatttaagtt acctgataaa t ttaaaatcg    33000 agagagatgg attctttgct cagttgggat acaattaatg taacctgtgt g aattagttt    33060 aaaaaattag ttttgtagag ttgggggggt tcttaaaatg gatccatcta a tctagtttt    33120 tccattattt ttcagaggtt tcacttttaa aaagaaaaca tcttcagata a caatgtatc    33180 tgtaactaat gtgtcagtag caaaaacacc tgtattaaga aataaagatg t taatgttac    33240 cgaagacttt tccttcagtg aacctctacc caacaccaca aatcagcaaa g ggtcaagga    33300 cttctttaaa aatgctccag caggacagga aacacagaga ggtggatcaa a atcattatt    33360 gccagatttc ttgcagactc cgaaggaagt tgtatgcact acccaaaaca c accaactgt    33420 aaagaaatcc cgggatactg ctctcaagaa attagaattt agttcttcac c agattcttt    33480 aagtaccatc aatgattggg atgatatgga tgactttgat acttctgaga c ttcaaaatc    33540 atttgttaca ccaccccaaa gtcactttgt aagagtaagc actgctcaga a atcaaaaaa    33600 gggtaagaga aactttttta aagcacagct ttatacaaca aacacagtaa a gactgattt    33660 gcctccaccc tcctctgaaa gcgagcaaat agatttgact gaggaacaga a ggatgactc    33720 agaatggtta agcagcgatg tgatttgcat cgatgatggc cccattgctg a agtgcatat    33780 aaatgaagat gctcaggaaa gtgactctct gaaaactcat ttggaagatg a aagaggtaa    33840 caattatttt atcttcattt tagtatgttc attgtacttt tttattcaaa g ctagccatt    33900 gggaatagtc atgaatatat agagctttg tccttaaggt tgttagggtc t ttagtggtg    33960 ctttttgaat aatctgttgg ccacatttt gaggcaggac gtactgatga a atggaaggt    34020 tttagtctgc taatatagtt tccaggatag ctctgtgatt ttatacatga a gaaaataca    34080 ggagtttccc cttgtccaca gctttgcatt ctctgaggtt tcagttaccc g cagccggct    34140 gaggtctgaa aatattgcat cacttctctt gcgctttggg accattatta a gaaaacaca    34200 agccctgcaa taccgcgaca gtcaatctga taactgagac cactactaag t gattaacag    34260 caacccaggt ggacagatca ggtcgggca agattttatc acactatact c aaaacagct    34320 tgaaactgaa cacttatgaa ttaatttatt tctgggattt tccatttaca t cacaatgcc    34380 tacatcattc acctctcttc atctcatcat ataggcattt tttatcatct t atatcttta    34440 caaaggaagg gtgagtagag taagatattt tgagcaaggg agaccacagt c aaataactt    34500 ttattgcaga atattgttat aattgtgcta tttcattagt tgttcacctt t tgctgtgct    34560 taattaataa attaaactct atcataggta tgtatgtata ggaaaacaca t agtacttat    34620 cgggtttgat actatccgag atttcaggca tccaccgggg tcttgtcaca t atttcctga    34680 agataagggg gttgctgccg taagatccat agaggttaaa atggtggtta g tggtaaatt    34740 ggaaaatgaa actaagcctt tctactgtaa ttcctttatg gcttgttgcc a cctaatatt    34800 gatgtataat gtgctctaat tgcactatta agtattata aattacattc a agtttttc    34860 ctggctagat cttgtaatta tttaatgtcc aaaattgagt aactgagatt a cccacatgg    34920 ggaagtaact caccttatga agcagttgca aatatgagag taaaattttt a aaccctga    34980 atcccattaa ggttactcta gggtgagaga gcactgaaaa gtgattgacg a taagcaaaa    35040 ctatagtctc atcaatgatg cctctgtttc tgaaggaa atttgttaaa a gatagacag    35100 caacaatttg ggttgtgttt tcccacatag tccaaaagag agacttaaat a actgggaaa    35160 ctttgtgtta aagatgattt gtacaagcag ccgtgtttgt gttattatca g acttatctg    35220 ttgcactta cccttattta aatatgagtg aaaagttaaa aactagaaac g tcaatagca    35280 aatacgtgtt tcgtaattaa ccagagacag acatgaaaat ccctaagcaa a tcttcggcc    35340
```

```
tcagtcgagc attcactgga cttaatccac ttgactcaat agtaatcatt t atgaataaa      35400 taagccagca ttagcatgta aagggagagg atccatacaa agtggtgtga t tgtttgtga      35460 cttgccagaa gcactcattc ttaatcgctc atgccctgtt ctttctgtct c attagtggt      35520 taacaaatct atgtttatca actgttttac tgtagataat agcgaaaaga a gaagaattt      35580 ggaagaagct gaattacatt caactgagaa agttccatgt attgaatttg a tgatgatga      35640 ttatgatacg gattttgttc caccttctcc agaagaaatt atttctgctt c ttcttcctc      35700 ttcaaaatgc cttaggtaaa ctagctaaat aattagcatt attatttgtt t ctgggatac      35760 tttaaattgt ttaatttagt ttataatatc atttctatat aaaagtattt t gtgctttct      35820 acaattattt tacattcaag tgaaagcctc aaaaaaaaac cctgtttata c atttaattg      35880 gttgcattct aaagatgaag tcccattatg attaattaca tgaaacttca a acaatttta      35940 ggtagctgat ttttttttt ttttgagaca gtctcgctct gtcacccagg c tggagtgaa      36000 gtggtatgat cttggctcac tgcagcctcc acctcccggg ttcaagtgat t cttgtgcct      36060 cagcctccca ggtagctgga actacaggtg cacaccacca tgcctggcta a ttttttgta      36120 ttttcagtag agacgaggtt ttgccatgtt gcccaggcta gtcttgaacc c ctgagctca      36180 ggcaatccgc ccgccttggc ctcccaaagt gctaggatta caggcataag c caccttgcc      36240 tggcettata tagttgattt tgacataagg aatatatttc taaaaatatt a tatttccaa      36300 acctgacctg aaatgacaca aagctaaccc attatatggg aagtgaatta g gacattagt      36360 actttttaaa aaaatcctac aggatagaat tggccattgt atttgttatt c actcaattt      36420 tagcaaattg gtgacatgat tattgttaat tggtagtatt acgagaaaaa t agatactcc      36480 acacgactca tcaacagctt aaattgctaa gtgtcaatgt taccttcgtc c tcatcccag      36540 tctcactctc agaccagttg agtggtagag tatagtatat actaaactga g caaaagttt      36600 atatagagtc tcaattctaa accagcattc tcatttacca ggtgaaacag c tgaggccca      36660 gggaggagca aggaattgcc caggttgata caatgaatga caaatggact c agatccagt      36720 gtagtgcctt ccctggtgtc atactgattc cttgttgaat gcctggcttt t ttctttact      36780 cattaaaaat gtgtgttacg caaataatat aatcatttta acaaggattc t aaataagaa      36840 ggaaggagca ctgctgggtg cggtggcatg gtagtggcct gtagtcccat c tactcagga      36900 ggctgaggca ggaggatccc ttaagcccag gagttcaagg ctgtagtatg c tgtgattat      36960 gcctgtgagt aaccattgca ctccagcctg ggcaacatag cgagaccctc a tctctaaaa      37020 aattaaaaag agagagagaa ggaatactag tagtcccaca attctgactg t tttctttat      37080 ccatcttcag ttttgataca tgtgtgtttg atttctgcat tgttgtaatc a acatgtaat      37140 tataatttta tattctactt tatttctctt agcattattt ctaaatcatt t tccaattgc      37200 tacatattta attcctttta atggctacat aatttatcaa attgtcatat c ataaataaa      37260 tttacctaga gtcttagcaa ttaaaaaagc ttgttttaca agtatttcc a aggtagact      37320 ctctttgtac atttcccatt gtaacttagt atacatatgt gtatatatta t aaaactgaa      37380 atagaatttt cacaatattt tttgtgcaat gcacagctta aattctatgc t acattttat      37440 ttcagtttta aaaaatactg gttgtaacct ctgaatttca gaagtcaagt g gtcagacag      37500 tatataacag agaagagaga cctgtttttc aaactcctct tttccaaaac c tctgtagct      37560 ggccctcaag attctccatc ttctggccac aatttacctt tttcagcttt a tctccactt      37620 atgcccttgc aataacccag tggttttaat gagtcaaacc aacaatctag a aagcatatc      37680
```

-continued

```
atttcttta attataatgt tattgtttaa aaaataaat taaaaagtta c actgttttg  37740 atttagttag aaagttgcat tccaaaatta ttctttagga aaatacagtt g attcccaga  37800 tgtcaagcaa atagaaatgt ccttttaaa atctttcttt catagtctga c actttcccc  37860 atacttgtca ttcagtttgc ttaaatctta tctccttggc aaagccttct a aagttccaa  37920 aaaatgttac ctttctttgg atttccacag tatcctctct ttaacactca t tcagtacta  37980 atttattttg ttatttgtaa agtattttt ctatgtaatc agactgacca g gtttatatg  38040 ttaatatgtt tttgtataat ctgtgtggtg aggtaattat atatgcagac a cacaaaaac  38100 acatgtacat atatttgcat aataagagaa gtccagaaaa agtgctttga a atctcagaa  38160 aaagagaca ttaataatca cttgctggag aagtaatgct ttggctgggg c tagaagaac  38220 aggtgtgatt tgggtacgaa gagattggaa tggcaggttt tccaaattga g aggatcagt  38280 ggcaaaatcc ccaaaatagg caatgcaggg cttatatgaa gaatgtaagt g gtacagtat  38340 gactgaagat ttgtgttact gaaaggacat aatcggagat aatgttgaaa a gggctcttt  38400 ctggacaact tgaggacca gctaaagaag ttttataatt gaggaaattt a aaaaactac  38460 ttctcttttc tgttatatat tgtctgatca gtggtagaaa aatattaagg g tttcaaaat  38520 tatacattta ttgagtctag cctatagtat gattggctta acattttttt t atttgcagt  38580 acgttaaagg accttgacac ctctgacaga aaagaggatg ttcttagcac a tcaaaagat  38640 cttttgtcaa aacctgagaa aatgagtatg caggagctga atccagaaac c agcacagac  38700 tgtgacggta caagcaatat tttagacata ccatgtattt caactactta c ttttgaaaa  38760 caacgtaaca caaagattgt gttttgaacc tgtggctgta tgttataaaa t ggcagattt  38820 gtagtttctt ttcttctaat gtcataacct tgttactgg ttagccagca t ttgcctgaa  38880 caactcatga actcatgctc tcacaagggc gttcattccc cattttgaaa a tgctacttg  38940 ttagaaatca tctctcatac tgagccaaga tctgcaactt taattctagg a ggtttttaa  39000 atttttattt acaaatgaga acttccacaa aatcctgtgt ttcagaaaca c ggaccacag  39060 agcgtaatct catcataata gagtttccct cccctccctt gactaaatat t attaggtct  39120 tttaactctc cttgctagaa attgctttct tgaccttca tcctccggtt c tcccttgta  39180 tatactctga gtctaggtct gggtcttgat gttcatttaa agctaaatac t tgtttgctt  39240 gttttgtttc taattcattt tttattttt attaaatatc tagtgtaaat a atcagatag  39300 cagtgcaaga ctttgataaa cgacagtccc ccttcccact cttggtgtct g ctgctcaga  39360 ggcaccttca gtctgaaaat atacatcctc ttgtagacat ttttctggca t tatttcttt  39420 ttaccttctt tttctctttt tcactcttcc tggaacttct atgatttgca t gttagactt  39480 ccattaatta tcttttctat ttttcatctc ttgatttct acttttagg a tatttcctt  39540 gatttatct ttaactcttc tgtggaattt ttaaattct atcaaggcaa t ttccgagag  39600 ctcttctttg ttctctggat atctctgtcg tgcattcgag tctgagggct g ctgggcttt  39660 tttagcgacg tctgcatgca tgtgcgggtc atgtgtgtag tgttctctgt g tgttgtttt  39720 tgtttcctcc agtttttttg tggtttattt tggactcaat ttattttaga g atattcagg  39780 aggtgactga tgtgctgggc gctcttataa agtgccttac aatattaact a attcagtca  39840 tcaccataaa ctacctcaaa ctttaaggta gtttcctttt tttttttttt g agacggagt  39900 ctcgctctgt cacccaggct ggagtgcagt ggcacaacct cagctcactg c agcctccgc  39960 cttccaggat caagtgattc tcctgcctca gcctcctgat tagctgggat t acaggtgtg  40020 taccaccata tctggctaat ttttgtatt tctaatagag acagggtttc a ccatttag   40080
```

-continued

```
ccaggatggt cttgatctcc tgaccttgtg atccgcccac ctcggccccc c aaagtgctg   40140 ggattacagg cgtgagccac cgcgcctggc ccactttaag gtagtttctg t tatccccat   40200 ttaacagata atgaaactaa ggtacaggag cgttaaatag ttacacaccg t catagaatt   40260 agcctcagag ctaggatctg aacacagcag tcttgaggct tttgagtttt c attgataac   40320 aactgcatta tactgtctct gtatcattaa gtttcactaa taaaatggtt a gctagaaca   40380 ggggcaagga cagagttcta cagcatgtca atagaggctt ccctcttggc t tacaacagt   40440 ccattcatca ccacttcttg ttcagctagt tacatatctg tcttcagacc a tgtttctgt   40500 tctttatcca tggagacaca aaagacttga ctatgtgact ccaaaaagtt a gaggtgtga   40560 ggcagcaaga aggaatgggt gggacattga ctctagagtc ctacagacct g taatagaaa   40620 cctgtctcct cctactcttg actatgtgac tatggcaaat agttaaactt c tctggactt   40680 cagtttttc ttctataaaa tgaggagaat gatatctacc ttgctgggta g ttgtcagga   40740 ttcaagataa agtgcctagt acactgcagg cctttcataa atgataacta t tgttatctg   40800 ccagtctagt aatccttta aaaaggaaa tacattaaga cggatggttt g tttttatga   40860 actttgcta actctattat tgtttcctcc cccttagagc tcacaaagca g ctatttgat   40920 aacaggctct agaattttgc tttgaattta catcaaatca ccagcctgta g tttttggca   40980 atcactttca aattttttga aaattagaac aatgtttgtc tgtcctcact t tccatcagt   41040 tctcttattc actagatgcc tcacacacgt gtcagtgaca ggggctctga g atcctgttt   41100 gcaggtttcc tttgtactct gaggtataat ctgtctagac aaggagtctt g ggctagtct   41160 ctgatagcta ggtacccct tttatctccc tctgagcctg tcttggcttt c agttccatc   41220 cgaccattgt gtattctctt tccaatctga tgcttgtttt ccttgcagag a aaacagaag   41280 taagatagga attcagcaat tccatttac atctcatacc tcacatttct c tcagtcacc   41340 agaagtccaa atttcccagg ccattcttgt gcagatgccc ctcctcaccc t gccatcttc   41400 actccctgtt ctgtcctcac ttcctgtcct tcctggcttg taaaccattt a actgactgc   41460 tctgtcagca atgtccctgt agcctcatcc gcttctctga tcattttctt c cccttcttt   41520 ctctaattgt tttctgagga tatgtactgt tccctgca gcccacctaa a ctgttttt   41580 actctcacag actttaggcc tgagaggtgg caaaggcatc tgttgtcctt g cttcctatt   41640 gccattttt ttcctttttt tcatctttt ttttttttct cgctctgtca c ccaggctaa   41700 agtgcactgg cgcaatctct gctcactgca acctctgcct cccaggttca a gtgattctc   41760 ctgcctcagc ctcctgagta gctgggacta caggcatgca ccactatgcc c agctttttt   41820 gtatttttat tagagacagg gtttcgccac gttgaccagg ctggtgtcaa a ctcctgatc   41880 tcaggtgatc ctccagcctc agccttccaa agtgctggga ttacaggcgt g agcaccata   41940 cccaggcgca gctgaggttt tagatgaagg aaagggctgg cacggtggct c acgcctgta   42000 atcccagcac tttgggagac cgaggtgagt ggatcatttg aggtttagga g ttcgagtcc   42060 agcctgccca atgtggcaaa tccccatctc taataaaaat acaaaaaagc c gagcgtggt   42120 agcgtgtgct tgtagtccca ggcactcagg aggctgaggc aggagaatca c ttgaaccgg   42180 ggaaacggag gttgcagtaa gccgacattg caccactgca ctccagcctg g aagacagag   42240 caagaatctg tctcaaaaaa taaaataaaa taaaacctct actgctttga a attctattt   42300 attagttatg gctaattttt taaaatggga gtgggctggc aggattcagt t gttcaaaca   42360 tcatatcagg agttgctctg tctctcactt cccttctctc tcctctcttc t gtcccatct   42420
```

```
ctccgggtca aacctccatt tctttctatg tgctttctac ttttcctttg t atcaatctt    42480 atttgaaatc tgtctttctt tataaggtga cagaaatggc caccagaatc a tattaagct   42540 tggaaaaagg gaggtacttt ttcccagtca gccctaagta tttccagagt t aattttcac   42600 tgggctgcct tgtgtcagat gcctactgag ggagtgggaa gggtaggtct a ataggaaat   42660 cttggtaaca gtatatgtta ccattaaagg gaagcctgga ttccaggcag a tcaaaacaa   42720 caggtagggc tcttgcctgt ccaacgctta acaatacact ttgtgttggc a cagtgagct   42780 ttgcacatga agttagttaa aaataaaatc atagttaact gataaacctt t gttccagcc   42840 aatgaccttg cttaccccaa gaaatattat ttattaaata ttatgaaatt a aatgaaaac   42900 agttatgagc tcttatgata aagcgtagag acaacccaat ttcaagttaa t tcacaggaa   42960 gataatagga caatatatgg ttgtttatga tcttgttttt acactgcttc a tattttaca   43020 tatgtgactt tcaaaatctt aagacttgac tgggcacagt ggctcacacc t gtaatccta   43080 gcactttagg aggccaaggc gggaggatca cttgagccca ggagtttgag a ccagcctgg   43140 gcaacatggc aagaccctgt ctctacaaaa aataattaat taaaaaaaaa a aaagaaga    43200 agatgtgttg tgttgctggg cacagtggca taggcctgta gtctcaccta c ttggggagg   43260 ctgaggcagg aggatctctt gagcccaaga gtttgagggt tcagtgagca g tgattgcac   43320 cactgcagtt taacctgggc aacagagcca gaccccctt cttcttcct t tcttctttt    43380 cttttttttg tgagacaaag tctcactttt gtcccccagg ctggagtgca a tggcacgat   43440 ctcagctcac tgcaacctcc acctcccagg ttcaagcgat tctcctgcct c agcctcccg   43500 agtagctggg attacagaca cgcaccacca tgcccggcta attttttatat t attagtaaa  43560 gacgggtttt caccacattg gccaggctgg tctcgaactc ctgacctcag g tgatctacc   43620 cttcttggcc tcccaaagtg ttgggattac aggcgtgagc caccgtgccc a gccccactt   43680 taaaaaaaaa aaaaaaaag aaaaagaaat caagatctta agactttttt t tttttttt    43740 agtgacaggg tctcactgtg ttgcccaggc tggtcttgaa ctcctggact t aagcaatcc   43800 tcctgccttg gcctccccaa agggctggga ttacagtcat gagccaccat g cctagccaa   43860 gactttttt ttttttcctc aaagaaaaat attaacaaca taattatttt a tagctagac   43920 agataagttt acagcagcag cttattcatg tgatggagca catctgtaaa t taattgata   43980 ctattcctga tgataaactg aaactttggg attgtgggaa cgaactgctt c agcagcgga   44040 acataaggta tcttaatttt ccccttctg gaatatatct gattatattt c taccactct    44100 aagtgaaaaa tggacagggc aaaatgttca ggctttctgg cctggaaatg g cataaggat   44160 gatcatcatg ccactatgtt tttgatttgt ttacttttca aaccactcct t taacattcg   44220 tattcatgtt tttaagattg ggaaaaaagc gaatatattt tgctacaatt t ctatttggt   44280 atgaaaacta cagatttgct tttgtggcct accagagtaa actacttata t ttaatacgt   44340 tgttctcttt tctctcttca gaaggaaact tctaacggaa gtagattta t aaaagtga     44400 tgccagtctt cttggctcat tgtggagata caggcctgat tcacttgatg g ccctatgga   44460 gggtgattcc tgccctacag ggaattctat gaaggagtta aatttttcac a ccttccctc   44520 aaattctgtt tctcctgggg actgttact gactaccacc ctaggaaaga c aggattctc    44580 tgccaccagg aagaatcttt ttgaaaggcc tttattcaat acccatttac a gaagtcctt   44640 tgtaagtagc aactgggctg aaacaccaag actaggaaaa aaaatgaaa g ctcttattt    44700 cccaggaaat gttctcacaa gcactgctgt gaaagatcag aataaacata c tgcttcaat   44760 aaatgactta gaaagagaaa cccaaccttc ctatgatatt gataatttg a catagatga    44820
```

```
ctttgatgat gatgatgact gggaagacat aatgcataat ttagcagcca g caaatcttc   44880 cacagctgcc tatcaaccca tcaaggaagg tcggccaatt aaatcagtat c agaaagact   44940 ttcctcagcc aagacagact gtcttccagt gtcatctact gctcaaaata t aaacttctc   45000 agagtcaatt cagaattata ctggtaagtt taaaataaat tgaatgctta t atgaaaaca   45060 aaactgtccc aaaataggaa ttatataaga aaaaccatag caaatcatca t tgcctgaaa   45120 acattgttgc tatgcaaatt tctactgatg atatgaatta caaatcacaa t ttcaaaagc   45180 aagttgctct tttgtctcta tagcagctgt agttttataa aatgtgtaat t ataacctat   45240 tgtagtacgg ctctaaagtc attacaaatg tgatgtgcct ttgaattaac a ttttttagt   45300 tcctaaaaca aactcatgag ggccaagttt ttaatgattt tgggatgggc a aaagcaaaa   45360 atggattcgc atgctaaaaa tgtattttag aattctgtac tgatgagaat c gattaatac   45420 aaagtagaga agcatgtttt atgtgttaaa atgttaaaat atagggtagt c tataaagga   45480 tatgaagtca ggagtgtctt aaatcagtca aactacttct ttgggtctaa g ggctcactg   45540 catgccatgt gctatgttgg gcgccgatca tttaaagatg aataacaaat a ctaagtagt   45600 tcctgccctc ctggagctca cagcttagtg agagagaagt tttgagagga a tgaaattag   45660 ccactgaagg ctccagagaa aagccaaaaa taatttttaaa accttacatc a accctataa   45720 agttatcaaa agtatttttt agctgaaata agtttataaa gtacagccct c ctattttt   45780 gccattgatg acttaatacc acggaggttt ttcttacagt tacgctgctg a cctttaaaa   45840 caacgattaa tggatttatt tttgtatcat gttagaatgt gtcatacttg a tgtttgcaa   45900 ttatcttgag acagttgagt gttggggtta gcgtaactgc cagagctccg t gagtacctc   45960 ttgttctctg tgctgaacca gagttgcgac agccaggctg cagagcaggg g cacgtgtga   46020 gagatgttat gaaagaagag cctgaggaag ctcagatgac tccaaggttt c agacactga   46080 tgactgggaa aactgtgaca ccagtaacac aaacagggga gtcaggaggc g gagtcagat   46140 ttggagaaaa gctgagaagg gctagtttaa gtctagaggt taaagtgctg g taagtcatt   46200 caggtaccaa tgtcttgcag acaacgggag ctgtgtgcag gactggaact t aggagggtg   46260 tcagttgggt cttaagagag gtgtaggcat ttgctgcaca cgggtcatgt t taagatcat   46320 aggactagga aagctccaaa aaagaatgtc tacagagccc agtcccaaat a tctgaaaga   46380 ctccctcccc tatttatggg gcagatggag gtagtagagc caggaaaggg a atttaaaat   46440 gagtagaaaa ccatgattgt cttggtggtc atggttggag gaagggagaa g aggaaggaa   46500 agaataaaag tagtggtagg tgctgtagaa aaagtcaagg aaatacttga t ttgggactt   46560 tggcaagttt ttggtggctt tgagacttgt agggaaggaa agccagtaaa g agtttaaga   46620 actgtgctgc agggaaacgt gtgccagtga ttctgcaggg caaggaaat g ctaaagctg   46680 tactttcact gtattcatgt actgattttt cttaacgttg attattttcc t agacaagtc   46740 agcacaaaat ttagcatcca gaaatctgaa acatgagcgt ttccaaagtc t tagttttcc   46800 tcatacaaag gaaatgatga agatttttca taaaaaattt ggcctgcata a ttttagaac   46860 taatcagcta gaggcgatca atgctgcact gcttggtgaa gactgtttta t cctgatgcc   46920 gactggtatg tattttagaa agtgaattgg caggaatcca ttggcagatg t taaatgaaa   46980 gctctttaat agaaataaaa agaccaccta cacagtattt ctatcattta g ggacctctt   47040 aaacctcctg taccatagtg agaaagcata ttactttata tcctttgttc t ggttgttga   47100 catcatgaag tttatagccc tgtaagattt tcaactcgaa gctcattgtg t tgaactgat   47160
```

```
ctagaatttt tctttgggaa tttttctttt ttctagtcta agcagttttg g aaatcaaac  47220
agaaaaatcg ctgtcagaga ccatgaccat ttctggcagt ttatttgcaa c aatctggtg  47280
ttgcatagtg gttaaatcat atatgcatat atgcatagtg gtccatcagc t atggaccaa  47340
aggcctggac ttaaagaaca gctctgctgc tcacagcagt gtggccacat g caaggcact  47400
ttactccctg ggcccatttt ctcatgtgtg caatggtgat agcagtaaag t acctggttc  47460
acagagtggc atgaggatta aatgaaaatc atttagcacg atattgtgtt g gccccactt  47520
taaagagtct aggacattca ttgtgctgtt aaagcttatg acagctgttc a atgatttat  47580
agtcattcac atgagaatat taaatcaaca gggcagagcg caaggagaat t gcagtttc   47640
agtacctatg tgtagtcctc cctctgtcta tcacctgact tgtgaccttt a gcaagttag  47700
ctagtgctgt cattattgta taatgttgac tgggcatctg aactttttca t cctggtttt  47760
tagatttaga tagccttggc ttaataatca gcatttcaat ttttattaat t tattaatca  47820
ctctgtgcct tccttcaac cctattttgg tgtttcagaa ctctaacgct g gaaaaaacc  47880
ttggcaatga tctaatccat tgatttttt tttccaggg ttcccattgt c ctttaggt   47940
ttcaagaggg cattttaag gtccttccac cccaatttca accacttgtg a gagagagat  48000
atatataata tataattata tataatatgt atattgtatt gtataataa t gtctattat  48060
atataattat aatatatagt gtgtgtgtaa atattccaaa taagtttat t ттатттта   48120
ttcttatta ttttgagac agggtctctt gatctgtcac ccatgctgga a tacagtggt   48180
gctatcacag ctcactgcag cttcaactgg gttcaaacaa tccccccac c ttagcctcc   48240
caagaagctg ggctacagg catgtgccac cacacctggc taatttttaa a tttttgta   48300
gagatgggat ctcactgtgt tgcccaagtt gatctcaaat tccctgggct c aagcagtcc  48360
acctgcctca ggctcccaaa gtgatgggat ttataaataa taaaagtaaa t aaacattat  48420
atagaaagta attatttaa tcctagtgtc atttttagag actcttctac t actagaaat   48480
aaaaacttta ctgtattcca ctacatttta agtttcctgc ctaattctt g cctttgcta   48540
ttatatgt ctatataaga tgtcctaggc cgggcgcagt ggcttgtgcc t ataatccca   48600
gcactttggg aggctgaggc aggtggatta cctgaggtca ggagttcaag a ccagcctgg  48660
ccaatgtctc tactaaaaat acaaaaatta gcaggatgtg gtggtgcatg c ctatagtcc  48720
tagctactgg gagggtaag gcatgacaat tgcttgaacc tgggaggtgg a gattgtagt   48780
gagctcagat ggcaccactg cactccagcc tgggcaacag aatgagactc t gtctcaaag  48840
acaaaaacaa aaacaaaaaa aacactttt tttaaagat cattttaca c атTаттааа   48900
atTgcctaaa tataatagtt tgagtcattt gagtatggca aatTgttggc a ccagggaca  48960
atATgccttg gtgtccttat aatgatatga tttctttgt aacttttaca т tcatgctct   49020
gaagacagaa cctgacagat atttttcat tgttctcttt caggaggtgg т aagagtttg   49080
tgttaccagc tccctgcctg tgtttctcct ggggtcactg ttgtcatttc т cccttgaga  49140
tcacttatcg tagatcaagt ccaaaagctg acttccttgg atgtaagtta т aaaaatact   49200
aataaaaaca cgccttagaa acaatTaaat ttcagtcctc tggataacct т ttattaaa   49260
tagttcgtga tttgtaaaaa ataaagcaca gcagttaaat tgcagttga a cagaagtct   49320
gaaaatttga tacagataac ctctagttca atctgtttt attctacaag a atgtatctt   49380
agtaagaact ttaaccaat gctattttt gctgatgtaa atttttttaa c gaatagaaa   49440
atcatttctt ttttcagtac тgccagтgтcg gcatagttct ctttccctta т atcttaaag  49500
tgcatacaca catgcatgcc tgcacacata tatcttttt tctcatggct g agtttaagg   49560
```

```
aagtaaatga atgcattcta cttaactctt cacaatgtag ttgggggtgg t ggctcatgc   49620 ctgtaatccc agtgacttgg aaggcaaagg tgggaggatt gcttgaggcc a agaattcaa   49680 gaccagcctg ggcaacacag caagactttc tctacagaaa aataaaataa g ctggacatg   49740 gtggtgaaaa cctgtggtcc cagctgctta ggaagctgag ggaagagggt c gctagagcc   49800 caggagtttg aggctgcagt gggtcatgat catgccacta caatctagcc t tggtgaaag   49860 cgagaccccg actcaatcac attgtgatta aaaagaactg ttttaagagt t atgagtcac   49920 caccccctcaa taagaccact agtttggttt tcttccaaag aatgtcttag t gcagtggtg   49980 gtagccattg ttcaaccatt tgtcatatta tggcccttc attgtcatta a tctttaaaa   50040 ccctgaaata catttatcta aaaaaaagat gccatacagt aggactggaa t atcttgtat   50100 accaaattca tatttatctt atttacaaag atgaaaaata aagcaagaaa a ggaaataaa   50160 taatgagaag accattttgt gttatgcttt tttttgtttt gttttgtttt g ttttaagac   50220 agtcttgttc tgttgcccag gctggagtgc ggtggtgcaa ccttggctca c tgcaacctc   50280 tgcctcccaa gctccagcaa ttttcctgcc ttagcctcct gagtagctgg a attacaggc   50340 acctgccacc acgccaggct aattttttgta ttttcagtag gatgggggtt t ctccgtgtt   50400 ggccatgcta gtcttgaact cctgacccca agtgatccac ctgcctcagc c tcccaaaat   50460 gctgaaatta caggcgtgag ccaccacgcc ctgcctgagt tatgcttaat a agggttttt   50520 taaaatgtat gtacttacat acttgttatg ttgagatatg tatttccttt g ataggtttg   50580 atatgtgact aataaaatat ttataaaacc taaggacaaa tgtaattttg t caggttaat   50640 gtataaaatt gaaattgttt actactttta tacttagatt ccagctacat a tctgacagg   50700 tgataagact gactcagaag ctacaaatat ttacctccag ttatcaaaaa a agacccaat   50760 cataaaactt ctatatgtca ctccagaaaa ggtttgtatt tatatcatta t tttaaaata   50820 tattaaagac cactagaata catatatttt taagatttta acaaaatttt g tatacgtag   50880 tgcaaagaat ttttgtacaa ctttcatcca gaaaccccaa atggtaacat t ttactataa   50940 ttgctttgta ttctctctct gcatatattt tcctgacaca tttgattgaa a attgcagac   51000 atggtatcct tttaagccct aagtacttca ctgtacattt cctaaaaaca a cgtattctc   51060 tcatataacc tcagtacaat gatcaaaatt aggagatgta cattgatgca g tactattac   51120 ttaatctgta aaccttattc tggtttcact agttgtccca ataatgtcct t tatagcaaa   51180 agaaaatccc agatcatgca tgcattccgt tgtgcttctc tgtaatcttg t aaacagttt   51240 ctctctctta atatctttcg tgattttgaa gttttttgaag gccagtcgtt t tcggaattg   51300 tccctcaatt tgagtttatc ttgcttcctc ctgcttagat tcctgttact c cttgaatat   51360 cacagaaaca gtgatatgtt ctcatgccca ctgtcaggag gcacttgatg t cgattcgtc   51420 ccattactga caatgttagt taactgatcg cttggttatg gtagtgtctg a tagacttct   51480 ccgctgtaaa gttactcatt tcttttttggc ctttgtaatt agtagatatc c tgttgtggg   51540 atgctttgag actatgtaaa taccctgcta gtgatcagaa ttttacccac a agtttagt   51600 atccattgat gattcttccc caaatcagtt attactatga tagatataaa a ttattttttt   51660 aaatgtagtt ggtgttttgc cataaggaag agttttcctg ttggttacac t ttttttttc   51720 tttttttttt tttgaggtag agtctcactc tgtcacccag gtgggagtgc t cggctcact   51780 gcaatctcgg ctcactgcaa cctggggttca agtgattctc ctgcctcagc c tcccaagta   51840 gctaggaata caggtgtgtg ccatgatacc tggctaattt ttgtatttttt a gtagagatg   51900
```

-continued

```
gggtttcacc atcttggcca ggctggtctc aaactcctga cctcaggcga t ctgcccacc    51960
tcggcctccc aaagtgctgg gattacaagc gtgagccact gtgcccagcc c acatattta    52020
ttgatactag catgaactcg acttcttaat ttattcaatg agttacattc a attatcaag    52080
tattttgatg ttctaattgt cctacatgtg accagtgaga catctctctc a agctggctt    52140
ctctgtcctt tgacatgtc ccggtcaaga tgtgagtgct acatgtgctc g ttgctactg    52200
agatgtcatt gcttctaggc cctgttatga agagagctat aaaatatata a ttttccc     52260
cagccaacac gcatccatat aacccagata tgtaaccctg ttgccaatgt a aatgtatgg    52320
tggccctcag atgtcttgaa gcagacaaaa gtttgagaac cactaacctg c taaataagc    52380
tgtttgctta atgttggtga acattctaaa atttgatctg ctattttcta t tacttctgc    52440
tgttctcttc atagattgaa ataagaacca attttatatg gaggtgtttt t gttttgtt    52500
tttgtttttt cgagaccgag tttcggtatt gttaccaggc tggagtgcag t ggcacgatc    52560
ttggctcact gcaacctcca cctcccgagt tcaagcgatt ctcctgcctc a gccttcctg    52620
agtagctggg attacaggca tgcaccacca cgcccggcta attttgtatt t ttagtaaag    52680
gtggggtttc accatgttgg ttaggctggt cacaaactcc cgacctcgga t gatccaccc    52740
acctcggctt cccaaagtgc tgggattaca ggcgtgagcc accgcacccg g ccttataga    52800
ggttttaata cagcttaagt tgtgatggaa tttgaagacc acagaatcat g aggtgatgt    52860
gtttcagtgt ttttacatgt ctaatgtatt tctggcctag atctgtgcaa g taacagact    52920
catttctact ctgagaatc tctatgagag gaagctcttg gcacgttttg t tattgatga    52980
agcacattgt gtcagtcagg taaatactgt tttttatatc cggaaatacc g ataaataca    53040
tactaccaac aatatatgta tttactgaat aaaaacccac actgagtgaa c gagtctcct    53100
attttactga agaataaggt agttcttaat acattgagca gtgttggctt t ttatagaag    53160
gaagctccaa gtagtctgaa aagcagtatt tttttttcca actagtgggg a catgatttt    53220
cgtcaagatt acaaaagaat gaatatgctt cgccagaagt ttccttctgt t ccggtgatg    53280
gctcttacgg ccacagctaa tcccagggta cagaaggaca tcctgactca g ctgaagatt    53340
ctcagacctc aggtgtaagt tgttgcacgt cacgtatttg agaaccctgg g gcagtgact    53400
gccagagctg ctacatgtta gaatcacctg tggcgcttta acgccaccac c caccccca    53460
ccccaccccc atgcccaagt tgtaacccga tggcagctaa atcagaacgt t tggggctga    53520
gagccagtat tttttttaaaa atccccaagt gattacaatg tgcagcagag t ttgggaacc    53580
agagtcctag ggcttttctt cacttactga aattaaaact ccttttcagt a cctacttta    53640
gaagtaggga taaattgcat gccatatcta tcatccctgg tatagtccca g taataaatt    53700
aatttttact tatctaattt tggcttccat atatcctaga gtatacttct t gaaatgaaa    53760
gatgaccctg ctttgtcatt tccccctaag gtcccagttg aatccaggat g ttgaaaata    53820
gtccagatac tatgtcgaat agctttttta ctttgttttc ttctcaacaa c aaaatgctt    53880
cttgttgcca ccaaatccat aattcttcag taacaaaatc tactataaaa g aaatcccc    53940
ccccctttt ttttttttg agatggagtc tcgctctgtc gcccaggctg g agtgcagtg    54000
gcctgatctc ggctcactcc gagttctgcc tcccggggtt cacgccattc t cccaccta    54060
gcctcccgag tagctgggac tgtaggcgcc cgccaccacg ccaggctaat t ttttttgta    54120
tttttagtag agacggggtg tcactgtctt agccaggagg gtctcgatct c ctgacctcg    54180
tgatccgccc gccttggcct cccaaagtgc tgggattaca ggcgtgagcc a ccgtgcccg    54240
gccaatcccc acatatttat ctaggctgta ctggattatt ttatacttct a cctgagttt    54300
```

```
gtagagatat ggattctttg gtaggtttat tcactcagca aatatttatt t aacaactgt   54360 tgtgtgccga gttttaaagta ttttttcttc tgatttatta gtgtgcactt t agtttcaga   54420 tgtaaacatt aacatggtat gcctgaagga gtaatgactg aattggatat t gaggtgaat   54480 ttttaaagca cggcttttgt tcatttgaaa ataaagacaa gctggtgcta t aaatattat   54540 aagcagtaag aatagcaaca gtatctctta gagggttatg agaagaactg a aggttcctt   54600 atgaaggata tgaatgggtc atgtgattaa gatagctaca aaagcttttg c aggttaaac   54660 tggcagcttc taaattatct gatctaaatc aaggaattca agcattttgg g tttcttcca   54720 gcctttaagt tgtttggttc cagcctagaa ttatttttatt gctagtagca c tgttatata   54780 gcacaaatga ccatactcaa gtgcaaggat tttagagtcc tcagaatttt g tgtgtgtga   54840 tcacaaagtt tggaatggaa tattgtaatt taatctcact tgcagaggag t atttgtatt   54900 aaatttgggg aaaaatattt tgcgtctata attgatatgc attataatgc t atatttaag   54960 atgtcgtatt aggctgggtg cagtggctca tgcctgtaat cccagcactt t gggaggccg   55020 aggcaggtgg atcgcctaag gtcaggagtt cgagaccagc ctggccaacg t ggcgatacc   55080 ccatctctac taaaaataca aaaattagcc aggcctactg gcgtgcgcct g taatcgctg   55140 ctactcagga ggctgaggca ggagaattgc ttgaacccag gaggcggagg t tgcagtgag   55200 ccaagatcac gccactgtac tccagcctgg gcaacagagt aaggccctgt c tcaaaaaca   55260 aaaaacaaaa aacaaaaaaa aagatgtcat attatacttt agattctaat a aataaccta   55320 tttgcaagta agtacttctg taagtactac attgatctat aattttttttt t tttttttt   55380 tttgagaca ggtcttacca tgttgccatg ttacccaagc tggtctcgaa c tcctgggct   55440 taaacagtcc tcccatctca gccttcctaa gtgctgagat tcttctgtcc t cttacgccg   55500 gatgcaatct actgttcttt tagatcagtt acatcaatgg caaatgccta t agttaaatg   55560 ataaaaaaaa tttctttttcc ttttgaatga cttttttgtaa gtataggatt t gtgatttat   55620 gtttgagtaa acagtgtaca tatttattta tttatttaga ggcaggcacc t gaatctgt    55680 tttcttagta ctgtggggaa gagatctgcc tgggaaagca aggttgtgga t tccagtct    55740 ccagcacttg gtacataatt ggcactcagt aataatcaat aaatgaaaaa t gtgaaggaa   55800 tttgggtaaa tgtaaaaatg taggcatgtc tgttgactcc ttaatgtgtt t ggcacttct   55860 ctgcatttgg aagtaggaaa ttttaaggaa tactttctgg gactctgttt c ctgatcttt   55920 tctgccagta ggccctggtt tggattaaat ttgctcaact gctgctatgt c gtggccctg   55980 gcgaagtcag gtattcctaa ggttgaagcc acagccctg tgctgctctc c tcccgccag    56040 tctgtaataa tattcttcct ctttgggaaa tataaggcac acaaaaaagg c tttattcca   56100 tttccttagg gccttaaaat atgaactgga agagagcaaa gagacaggca c atagagtta   56160 actataatag aacaataata atagctaaca cttacatatc cagcctactc a gtgtgccag   56220 gcactgttgt catttttaagt gtatttacct ccttgtccac acaaaagcaa g gtaggtact   56280 cctatttttcc tcattctaca ggtgaggaaa ttgagacaca aagagattat a taacttcat   56340 atgcctagca agggttggag tgagaactta aaacaccaga tagctggttt c agaatcctt   56400 taaatactag gtcaaattgc agaaagaaga agcagtgat ttgagatgta a attacagct    56460 gcaggaactg aagaagacaa gataagctag aaccccccagt aacagctgtt a caaggaggg   56520 gtcagatcaa gttttgtaaa ggcactgggc attgtaggag gagtagttta t ttaaaagca   56580 taggttgggc atggtgactc acgcctgtaa tcccagcact ttgggaggcc a aggtgggcg   56640
```

-continued

```
gatcacctga ggtcacgagt tcaagaccag actgaccaac aaggagaaac c ccgtctcta   56700 ctaaaaatac aaaactagcc gggcctggtg gtgcatacct gtaatcccag c tactgggga   56760 agctgaggca ggagaatcac ttgaacccgg gaggcggagg ttgcagggag c cgagattgc   56820 accactgcac cccagcctgg gcaacaagag cgagactgtc tcaaaaaaaa a aaaaaaaac   56880 aaaaagata aaagcgtaga cagcagccga gcgcagtggc tcacagctgt a atcccagca   56940 ctttgggagg ccaagggaga cggatcacct gaggtcagga gttgaagacc a gcctggcca   57000 acatgttgaa accccatctc tactaaaaat ataaaaatta accaggtgtg g tggtgggcg   57060 cctgtaatac cagctacttg aaaggctgag acaggaaaat tggttgtacc t gggaggcgg   57120 aggttgcagt gatccaagat catacgactg cactccagcc tgggtgatag a gcgagactc   57180 catctgaaaa acaaacaaac aaaaaaggc ttaaacagct gtattgaaat a aaatttaca   57240 taccataaaa ttcacctaaa gttgacactt caatggcctt tttttttttt t tttttttt   57300 agtttataag gttgtgcagc catcaccatt atctaatttt agaacatttt t gtctctgtt   57360 gaaaggggaga gtatacccat tagcagtcaa ttcctacttt ctcactttcc c cattcttag   57420 gcaaccctc atctactttc tgtctctgta ggtttgcgcc tattctggac a tttcatgta   57480 aatggaatca cataacatgt ggccttttgt gactgacttc tttcactgag c atgttttta   57540 aggttcctcc atgttgtagc ctgttttcag tatttcattc ctttctattt t cagataata   57600 ttccattttta tggatcctac tttctgtttt atttgcccat tcatcatttg a tggatgttc   57660 aagctgtttc agtgttttgg ttttttgaa taatgctgct gtgaacattt g tgtagaagt   57720 tgttctgtgg tcatcagttt tatttctctt gggttgctgg gtctgtggta a ctgtatgat   57780 taacctttc aattcaagga ctactaaact agttttcaaa gtgcctccgt c tttttttt   57840 tttttttttt tttttttgag gcggagtctc actctgtcac ccaggctgga g tgcagtggt   57900 gcaatctcgg ctcactacaa cctccacctc ctgggttcaa gcgattctcc t gcctcagcc   57960 tcccaagtag ctgggactat ttttgtattt ttgtattttt ctaatttgt a tttttagta   58020 gagatggggt ttcaccatgt tggccaggct gttctcaaac tcctgacctc a ggtgatcca   58080 cccatctcga cctcccaaag tgctgggctt ataggtgtga ccactgcac c cgaccgcct   58140 ccatcatttt atattacctt cagcagtgtg tggggttgc agttttcca c atgcttatc   58200 aacacttgtt actgtctttt tttattacag ctatatgaag tggtaggtga a cggcatttt   58260 agcaggcaaa gagtgaaaat tcaggctga agtttctgtt ataaaagtac a ggtcaggcc   58320 aggctcggtg gctcatgcct gtaatcccag cactttgggt ggccgaggcg g tggatcac   58380 ctgaggtcag gagttggaga ccagcctggc caacatggtg aaaccccatc t ctactaaaa   58440 atacaaaaat tagccgggcg tggtggcatg cacctatagt cgcagctact c gggaggctg   58500 agacaggaga attgcttgaa accagaaagt ggaggttgca gtgagccgag a tcatgccac   58560 tacactccag ccaaaaaaaa aaaaaaaag tacaggtcag gcccaaggaa t ggtgaataa   58620 tccattggat aagtggagaa acatagagaa gggatgaccc tgacaaggtg g cttgacgcc   58680 agatcatgga ggatcttgca tataacgatg gtaaaatgtt tggactttat t cttttggca   58740 ctttaacctg ggaagtggct tgatctgaac tgtgtggatg aatgataacc c tggcaagag   58800 aatagaggag aggatgagtg agagaacaga agttagagg tagagcagcc t tcaggaac   58860 ttattgccta ttgcagtcat tgaggagaga tgatgctggt ggaaacagca g aagtggaag   58920 gaagaaacag agtcaagaga gagggcagga atggtaacta aatggaatga g aagagtgga   58980 tacggttgaa gtttatacta gttcctgggg caggtgccta gaaccattga c cataaatgg   59040
```

```
aatggaggaa ggaagatgag taataaattt gattttagat gcatgatgcc t gggatgttt    59100
aagggatgag tggatgacca cgatagccat cttcatacct tctttggtca c atgtacctc    59160
ctgaaaaaat cctggaaaac tatgtacctc ctgcatatat acatatatgt t ttaaatata    59220
tatataatat atatgtattt tatatatatg tgtgttttta ttttttatat a tatatgtgt    59280
gtgtgtgtgt gtgtgtattt tagaccaagt ttcactcttg tcgcccaggc t ggagtgcaa    59340
tgacacgatc tctgcaatct ccacctcccg agttcaagtg attctcccgc c tcagcctcc    59400
tgagtagctg ggactacagg cacttgccgc catgcccggc taattttttct a tttttagta    59460
gagacggggt ttcaccatgt tggccaggct ggtctcaaac tcctaacctc a ggtgatcca    59520
cccgccccag cctcccaaag ttctgggatt acttgagcca ccacgcccgg c cataagcat    59580
acattttgat tgagaatgta tctcttaatg agataggcct tttgtttgtt t gtttgttta    59640
agagatgagg tctcgttata ttgttcgggt tagtctggaa ttcctggcct c aagtgatcc    59700
tcccacctta atcttctaaa tagtgtggac tacaggtcca cacccagcta g gacttttgt    59760
tgttcactta gttgacatat ctggatgaat tgggtccatt tatatttctt a tttttatgg    59820
atgtaagcac taagaaatat tgctcacata acatgtaga tgggaatgga a ggcattttt    59880
tgtagctgta acaattattt gaattccttc tgatgtatat gccaagatta c gtaatgatc    59940
agtcatcaaa aattatttt aattatctgt caattgacaa ctcaattagg t ctttcaaat    60000
ttgtggtaag caaagaattg gaaactctct gggaaaataa gcaagatcaa t cgttattca    60060
ctttactttt tctaggaaaa ataccctaaa aaaaagcttt accaatactt a cctaatgac    60120
tattaagtag tcttattatt cttttcaacaa gaatcttgtt ccctgtatcc a atatgtatg    60180
gaagagttgg ggaaatcaaa atactgttag tttcagtata cctttccaat a tgatatttt    60240
tgacaaaata cttttattgt gtgatacgct tttctaataa ctttttttgtt g ttgttttt    60300
gagacagagt cccaatcttt cacccaggat ggaataagta cagtggtgcg a tctcggctc    60360
actgcaacct ctgcctccca ggctcaattt atcctcctgc ctcaacccgc c aagtagcca    60420
ggactacagg cgtgcaccac catgcctggc taattttat gtttttttgtt t gtgttgttt    60480
ttttcgtaga gacggagttt caccatgttg cccagactgg tctcgaactc c tgagctcaa    60540
aggatctgcc tgccccggcc tcccaaagtg ctgggattac aggcgtgagc c accattccc    60600
aaccatattg tgtgacatac ttttaaatag agttttgtca aaactgtggc t atagattag    60660
ctctttccaa aaatgggaaa tgaccaccat ataacctaat tggtaaagcc a gtctttatt    60720
gctaaattag acttcttttc tttgtgggtt ttgttttgtt ttgttttgtt t ttgttttttg    60780
ttttggagat ggggtcttac tctcactatg ttgcccaggc tggtcttgaa c tcctgggct    60840
taagtgatgt tcctgcccta gcctcctgag tagctgggac tacaggcaca t actaccatg    60900
cctggctggc ttcatttccc ttttctttt tgaggggggt gggggaatg g agtttcact    60960
cttgttgccc aggctggagt acagtagctc accgcaacct ccacctccgg g attcaagtg    61020
attctcctgc ctcagcctcc caagtagctg ggattacagg cgcccgccac c atgcccagc    61080
taatttttg tatttctggt agagacaggg tttcaccata ttgcgcaggc t ggtcttaaa    61140
ctcctgacct caggtgatct gcccgcctcg gcctctgaaa gtgctgggat t agaggcgtg    61200
agccactgca cctggcctca ttttcaatt cacataaact atttagtaca c atcccatga    61260
caactattgt caattccaaa agcaacaagc tgagctctaa ttgactttgt t tcctcacac    61320
aacactttga aaagacatga gtttgacacc ccaaacagga taatatttac c attttaatg    61380
```

-continued

```
gtaatatcca gcagaacctt agacaagaaa cagtagaatc taacttttaa g aaaacttta  61440
ttaaaatgta attcacacac tataaaattc atccatttaa agggtacaat t tagtgggtt  61500
gcttttttc tgtattttca cagaattgta caaccatccc caatatctaa g tttacagca   61560
ttttatcac cccagcgaga aacctggtac ccattagcag ctgctccgca t cttctccct   61620
cttgtttgtg cccggcttct ttcactgagc gtagttttca agggtcatcc a tgttgtagc  61680
attggtcagt aagtacttca ttcatttta tagctgaata atattgcagt g tatcagtat   61740
tttgcatttt atttatccat ttatcaattg atgggaactg tctgtaacta g gtatttggt  61800
aattccaaac atcttatttt ccaacaggca gagtaagatt tgttacatgt a ataaactcc  61860
aagggtctat taactttttc attataacaa attgtgtaaa tattgctttc a gttagttac  61920
ccacagtcct tttgcagtag agatagttgt cttggtttta attggattca t gatctacaa  61980
ctttatgttc taatctcatg tcatttttat tattttagt aaaagtaatt t gtttgacta   62040
aattaactgg taaacagttc tgagctttt caattgtgtc tacaaatttt a agaaattca   62100
gattatgtgc cagatgtttt tagtaacagc tttgttgcgg tataatccac a taccataca  62160
attcccatat ttaaaaagta caattcaaag tttttagtat attcagaatt g tacaaccat  62220
tgccagagtt ttagaacatt tcatcaccct ccaaaaacac ccatgcccat t gcagttcaa  62280
tctccttttc ccctcacatc cccatcctgc cagccctagg caaccactaa t ctgctttct  62340
atgtatagat ttgcctactc tgggtatctc gtgtaaatag aatcatccaa t atgtgatct  62400
tttttgtgac tgtctactta gcataatgtt ttcacggttt attggtgaat a atattccat  62460
tgtagacgtc tacgcattt tattcatcag ttgatattgg gttgtttcca t ttttatttt  62520
ttactattat gaataatgct ggtataatca tacatgtata aatttttgtg t ggacatatg  62580
ttttcatttc tcttaggtat atgcccagga gtgaaattat tgggtcatat a gaaactcta  62640
tgtttaaccc tttctttttt ttttttttga cacggagtct cactctgtag c ccaggctgg  62700
agtgcagtgg tgcgatcttg gctcactgca acctccacct cccaggttca a gtgattctt  62760
ctgcctcagc ttcctgagta gctgagacta caggtgtgcg ccaccacgcc c agctaattt  62820
tcgtattttt agtagagatg ggggtttccc catattggcc aggctggtct t gaactcctg  62880
acctcatgat ccgcccaact cagcctccca agtgctgga attacaggca t gagccaccg   62940
tgcccagcct atgtttaacg ttttaaagaa ctgtcgcact gttttccaaa g tggctgtgc  63000
cattttacat tttcactagc gatgtatgag ggttctaatt ttttcatatc c tcaccaaca  63060
cttgttttg tctctctttt tgacccaaag attttttaa attaataaaa c actttctg    63120
aaaataaata tatttttta atgtgggaaa agcaataag gccattgtta t gcccagtca    63180
ccatagcatt cctatcggtg gagagactca tgcaccgttt ccaacttaag c ccaaatcaa  63240
ctcaaatgca ttttaagatt ttcttcatca tttgtattcc tagacaattc t ttaatctac  63300
tacctttttt gccacaatct gctacacatt ctgccttttc aagcactaaa a ggactctag  63360
gagttttttg caaagaaatg ctgtcataag agtggtggta tcaaagtatt g tttaacggt  63420
agtctcaaag actttcaggg taatgcattc tgtgattata gagatgaaag a aacaacatc  63480
ataaagtgaa ggtcatcttc attcccacca ccttattctc agtatatctg a aatcagaac  63540
atcctaataa ggaccaaaat actttgttcc tagttattct tcacccttaa c agaaataag  63600
taaaacaccg aaagatatga ggccctccta ccaaggattt ctagtgcttt a attaaagaa  63660
aatttcacct acactcatac tatttttcag tttgctttgt ttggtgtcct g gaggttttt  63720
acatcctgga acagtgcaca gtggtaaaat tcagaatgga tgaaaagtag g attggtttg  63780
```

-continued

```
tttgttttca ggaagtgagg caatcgtaaa agggaaaaat gggaaaggcg a aacaagcag 63840
gatgtctttt tttttttttt tttctttta gacagagtct cactcttcgc c caggctgga 63900
gtgcagtggt gtgatgtcgg ctcactgcaa cctccgcctc tcaggttcaa g cgattctcc 63960
tgcctcagcc tcctgagtag ctggaattac aggcacgtgc caccatgcct g gctagtttt 64020
tgtatttta gtagagacag ggtttcacca tgttggttag ctggtttca a actccagat 64080
ctcatgatct gcccgccttg gcctcccaaa gtgctgggat tacaggcgtg a gccaccgcg 64140
cccgtccagg atgtctttt tctaattaga gacgagggtc tcactttgtt g cccaactgg 64200
tcttgaattc ctgggctcaa gtgatcctcc tgccttggcc ttccaaaatg t tgagattat 64260
tgatgtgagc caccacccct ggccagaatt tcttgtctgt gggagcattc t cagatcagt 64320
cttatgaaaa aggacagcca gcccttccta tctgcagttt ctgcatctgc a gattcaccc 64380
aactgtatat caaaaacatt tgaaagaaaa atagtttctg aaagtttcaa a aagcaagat 64440
ttgaatttgc tgagcaccaa gcgctatgct gtgtccacat gaatgaagtg a tgtgtaggc 64500
atactctgct gtatcctccc gccaggacag aagaaaaatg tcacatagtt a ctgacagta 64560
cagtgtagca actatttaca tggcatttat ttaatacatt gtattgagta t tataagtaa 64620
tctagagatg gtttaaagtg tgcaggagga tgtgcatagg ttatatacat a tactacacc 64680
attttatatc agggacttga gcatccttgg atttaggtat ccgaggaggc c ctagaacca 64740
atcccccatg ggaaaccaag ggatgtgaaa attgagggtc tgaatttgtt t aagattcac 64800
agaacagact gaaaagacaa gagaggagat aatggagaga acaagctcac t gaggaagtg 64860
ggcgggagga aatggggcaa gaatagtaga ccagaggaag aggaggagca c atctgtctc 64920
agagtcagcc acatttatt tggggccaag aacaaaaata aagtgactgt a atcagtagg 64980
gctttaactc cttctgctgt cctgcagtta gcttttatg tatcctgggg t gtccaatct 65040
tttggcttcc ctgggccata ctagaagaag aacgattgtc ttggaccaca c ataaaatac 65100
actaactggc cgggtatggt ggctcacacc tgtaatccca gcactttgag a ggccaaggt 65160
gggcagatca cctgaggtca ggagtttgag accagcctgg ccaacatggt g aaaccccat 65220
ctctactaaa aataacaaaa atgagctggg tgtggtggcg gcacctgta a ttccagcta 65280
ttcaggaggc tgaggcagga gaattgcttg aacccaggag gtagaggttg c agtgagcca 65340
agatcgcacc cttgcactcc agcctgggtg acaagcgcga gactccctct c aaaaaaata 65400
ataatacact aacagtaaca atagctgatg agctttataa aagaatcata a aaaatctca 65460
ctgttttaag agagcttatg aatttgtgtt ggaccacatt caaaaccatc c tgggctgca 65520
tgtggcccgt gggctgcggg ttggatgagc ttgagtacct ggtcaaaatt t gggaacatt 65580
gatggcctaa aaatacgtat atttcctgtg tgatttcctt aatattttaa a taatgttct 65640
aaccatctct gcttttagtc agcctcatct tggagtcaag agactgggct c ctgacttac 65700
tttgtctttc tatatgtttt ctcttccaca atcctaattt tttgtcatct a gtcccataa 65760
acattccctc tttatcacca ttcttttctt taacccttag ccttacttcc a tttcagtgt 65820
tctattgtgt aagctgctag cgacaatatt caacttaaga ctacttggta g gctgggccc 65880
ggtggctcat gcctgtaatc ccagcacttt gggaggccaa gcaagtgga t tgcttgagg 65940
tcaggagttc gagaccagcc tggccaacat ggtgaaactc tgtctctact a aaaatacaa 66000
aaattagctg ggcgcgatgg tgggcatcca taatcccagc tacttgggag g ctgaggcag 66060
gagaatggct tgaacccagc aggcagaggt tgtagtgagc caagattgtg c cactgcact 66120
```

```
ccagcctggg cgacagagtg agactctgtc tcaaaacaaa acaaaacaaa a caaaacaaa  66180 aactacttga tattagcttg ggctgctatg acagaatact gtagactggg t ggcttaaac  66240 aacagaaatt tatttctctt ggttctgaaa gccaggaagt ccaagatcaa g atgctggca  66300 gatcccaagt cagatgaagt ccctcttcct ggtttgcaag tggtagtatt c tctttgcat  66360 actgacatat gcgggtgggg agagccagca aggtctctac ttattttga g cacttatct  66420 cattcataac tccaccoctc atgacctaat tatctcccgg aggctccaac t cctaatacc  66480 atcacactgg gggttaggat tttaggggg acacatgtag tctataacaa t acctaaagt  66540 catatttcct cataataact aaattttatg tttgggactt ttttaggttt a gcatgagct  66600 ttaacagaca taatctgaaa tactatgtat taccgaaaaa gcctaaaaag g tggcatttg  66660 attgcctaga atggatcaga agcaccacc catgtgagta cagccatgtg a ttagctgtc  66720 tagaagtaac aaatgtcttt ttagtaccac aataagatat ataaaattgc a tattaaaca  66780 ttccttttg cattatgaca gcactaactt gctctttata gagcagacta t tgcaactct  66840 ctcaattctg gaaattataa aatctcattt ggtttaataa caataaattc t aacaaaaat  66900 atattaaata ctccctccta cacacgtata ttataacttt tggtttcaat g tctttcctc  66960 aggcttctat cagtgtttga attatacagc ttttgtttt agtgccttgt c ccaagcctg  67020 tctgcctttg cattatgtta actaaaatga gattctgaaa ttcatagtag t tttccatgt  67080 aaccccctt ccactttcc atggagaata tttttggtat ttctattta t tttttagaa  67140 attagtatac atatttgtgt ggacaaatca gtcagtagag atctaccaag a aaaagtcag  67200 tgatttcccc gctcagactc acctccccca ggcagctaat gtcaatagct t catgtgtat  67260 atctagacct ttggctcagt cacagagaga tgacttttcc tttaatatct t ttaatttcc  67320 atttctaaaa ataacacaca taataataaa tataatatat gctcattaaa g aaaatttat  67380 atggccaggc actgtggttc acgcctgtaa tctcagcatt tgggaggcc g aggtgggtg  67440 aatcacttga ggtcaggatt tcaagaccag cctggccaaa acggtgaaac c ccatctcta  67500 caaaaattat ccgacgtggt ggcacgcac ctgtaattcc agctattctg g aggctgagg  67560 cagaagaact gcttgaaccc gggaggcaga ggttgcagtg agttgagatc g tgccactgc  67620 actccggcct gggcgacaga gcaagactgt ctcaaaaaac aaaaaagaaa a tttagaaag  67680 caacaaaag aagaaacaaa agacaaacat cactcaatga gcaaaatcac t gttatgtta  67740 ttattaattt ctagtatttt tctatgcatt tttttctact agcatactat a tacgtttct  67800 accgttaatc tactttatat atcatgagca ttttcccatg tcttttaaaa a cttagaaaa  67860 cacttttgat agttatagta tattttattt cacagttccc tgtatttgtt t ccctaatgt  67920 tgctcagtaa aatctttgta atttttaaag tttgaagtaa aacttttgtt t atgtccttg  67980 tatcacttta tttcctaatt tcccagaaag aaactgagtc aaaggtattt c taagactct  68040 tgatacatac tgccatatgc ttttgacaaa gtttgtgcaa gaatggcttt t cttttttt  68100 ttttttttt tttttgagg ctgagtctca ctctatctcc aggcaggagt g cggtggtgc  68160 gatctcggct cactgcaacc tctacctcct gggttaaagt gattctcctg c ctcagcctc  68220 ctgactagct gggattacag gtgcccacca ccacacctgg ctgattttt t tgtattttt  68280 agtgaagata gcttttcacc atgatgtcca ggctggtctc gaactcccga c ctcaaatga  68340 tctgccctcc ttggcctccc aaagtgctgg gattacaggc atgagccacc g cgcccggcc  68400 aaggatggct ttttatacc cacatgtatc tagtgtgaag tagagcccag a gttcatcca  68460 ggtccacctc acgagtcatt agcagcgaca ggattaaaag ccacatctca t ttccagcac  68520
```

```
acatgaattc cttgcttgaa ttattcacgt gtgtggtctt ccagcagtat a agaacacta    68580 cgggagatct atttatggtt catatatttc tgaaaatgta gtgtaaattg t gttttgtt    68640 tatgttaaaa attcttgttt ctcagtactc ttggtttctt ggcagatgat t cagggataa    68700 tttactgcct ctccaggcga gaatgtgaca ccatggctga cacgttacag a gagatgggc    68760 tcgctgctct tgcttaccat gctggcctca gtgattctgc cagagatgaa g tgcagcaga    68820 agtggattaa tcaggatggc tgtcaggtaa catttttaaa gataaacaaa t aatagaaat    68880 aatcttttat agcatataac caaacatgca catgtagaat gcaaactgtt t ttaccttga    68940 aggtagtaaa catcaaaata agactgaaat ttaaaaaaca gatttttctttg agacttcta    69000 aagttgcttt ttctttcata aaaaaaatct gcttgagata taattcacat a tcataaaat    69060 ttatcctttc aaagcaaaca agttagtact ttttagttta tttgcaaagt t gtacaataa    69120 tcatctctat ctaattccag aatttttgat caccataaaa agaaacctca t acccagtca    69180 cttcccccac ccctaatgc ctggaaacca caaatctact aactactgct a acctgtttc    69240 tagagtttat tactctgtac attgcatgta aatagaatca tacagtatgt g gtctttgtg    69300 acttttcttt tttttttttt tttccggaga cagagtctca ctctgtcgcc c agactacag    69360 tgcagtagag agatcttcgc ttactgcaac ctccgcctcc caggttcaag t gattctcct    69420 gcctcagcct cctgagtaga tgggattaca gatgtgcgcc accatggcca g ctgatttt    69480 gtatttaata ttttagtgg agactcaaac tggtctcgaa ctcctggcct c aagtgatcc    69540 acctgcctca gcctcccaaa gtgctgggat tataggcatg agccacctcg c ctggcctgt    69600 ttgctttta ttagcataat ttttcaaga tttatccata ttttaggata t atgagtact    69660 tcatacctttt ttatggtcag ataatattct gttatatgga tataacacag t ttgtttatc    69720 tactcatcag ctggttagac atttggcttg tttcgtttct ttctttttttt t ttttttttt    69780 tttttgaga caggtgtctta ctctttcatt caggctagag tgcaatggca t gatctctgc    69840 tcactgcaga ccgtacctca aacaatcctc ccacttccca agtagctagg a cgacaggcg    69900 caccactatg cctggctaat tttttttattt tttgtataga cgaggtctcc c tgtgttgcc    69960 cagcctggtc ttgaactcct gggctcaagt gataatcctg cctcaaccta c caaattcct    70020 gcgattatag gtgtgagcca ccatccccga tgtgtttcta cttcttggct a ctatgaata    70080 atggctttgt gagcattcac gtacaagttt tccacggac atatgtttttc a gttctcttg    70140 ggtagacacc tgggagtgga cttgctgggt caaatggcaa ctctttgttt a acttttaga    70200 ggaactgtga aactgctttt caaagtggct ctgcagttct gcattctcac c agcaatgta    70260 tgaggtgcca gtgtctccac gtcttcacca atattttttta ttgtccagct t ttttaatgt    70320 attcatcctt gtgtgtggga aatggtatct cttttgtgggt ttttttttat t tacatggaa    70380 gaccacacac gtgaataatt caagcaagga attcacgtca cccaggctgg a gtgcagtgg    70440 cgcaatcttg gctcactgga acttccgcct cctggttcaa gcaattctcc t gcctcagcc    70500 tcccaagtag ccgggactat aggcacatgc caccacaccc agcttattttt g tattttta    70560 gtagagacag ggtttcacca tattggccag gctggtcgtg aactcctgac c tcatgatcc    70620 gcccactca gccccccaaa gtgctgggat gacaggtgtg agccaccacg c tggccctc    70680 tttgtggttt tgatttgcat ttccctagta actaacaata ttgggcatct g tttccgaga    70740 tgagaaattt gccgtcaccc aggtgggtgg ggaggaaagc tgaaaatact t taggcatct    70800 ctttttttttt tttttttttt tttttttttt tgagacggga gtctcactct g tcgcccagg    70860
```

```
ctggagtgca gtggcgcgat ctcagctcac tgcaagctcc gcctctcggg t tcacgccat   70920
tctcctgcct cagcctcccg agtagctggg actataggca cccgccacca c gcccggcta   70980
attttttttt gtatgtttag tagagacgag ggtttcacca cgttagccag g agggtctcg   71040
atctcctgac ctcgtgatcc gcccgcctcg gcctcccaaa atgctgggat t acaggcgtg   71100
agccaccgca cccagcctac tttaggcatc tcttattgtg gtaaatgcca g ccttggata   71160
gatccctcta aatgaaagga tgaatttcag caaaacaact aataattact t ggagccaat   71220
gaaaagtttc agctcaggaa aaagtattta ctttgaagat tcagaggaaa a atatctctc   71280
aaaattgttt tctctgggaa aacagaaaat tttagaggat atcagtttag t atcccgaga   71340
aagatataag aagacttaat atacgtgaac tagtaacaac ttccataaga t cacagggtg   71400
agatgaaggg agaaataaaa atccagttta tggccaggtg cagtggctca c ccctgtaat   71460
cccaccactt tgagaggccg atgtggacgg atcacctgag atcaaggagt t tgagaccag   71520
cctggccaat atggtgaaac cctgtctcta ctaaaaatac aaaaattagc c ggacgtggt   71580
gatgggcatc tgtagtccca gctactcagg aggctgaggc aggggaatca c ttgaacctg   71640
ggagccgaag gttgcagtga ccgagatcg tgccactgta ctccagcctg g gaaacagaa   71700
caagactcta tgtcaaaaaa aaaaaaagaa agaaaaattc agcttatcca a gtaagaaaa   71760
acaaaactaa gagcagaatt atatattaag acacaaatga aatgactcag t ctcagtgga   71820
gacaatagaa tcagtgatgt agtgagtagc ttgagaatgc aagggaaaaa a gagattaaa   71880
atggggtggg gtggaaatta tctttgttga caaaaggagg taaggattca g cctaagaat   71940
agtaagtgta cccaagcaag aaagcaggat aattgaaaca gataagtgtg t tataaataa   72000
atacataaca gatatataac aaaaataata gaagactgtt ttcagaattg g aagaaggaa   72060
gactgggact gaagaatttc gtacccagct cactgtcatt tatgttgaaa c caacaaaag   72120
gtcattttca gatatgcaaa aagtttagaa atacatcact catttgtctt c actgaaata   72180
ctgattttag tcttcccaaa ttagtttata tatttaaccc aaatgccagt g ttttgtttt   72240
tttttttttt ttttttttgg ttttttgttc ttttcccttt gataaacttt t tctaaagtt   72300
tgcctggaag aatattcaag tgaaaataac taagagagtt tggcaaaaaa c taataata   72360
caggaacact agtttgcagt acattatagg cagatcagtg gaacaggaaa a catgtaaaa   72420
acaatacatg ataaggaaaa agtttgcatg aaagggccag gcatggtggt t cacacctgt   72480
aatcccagca ctttgggagg ccaaggtggg aggatcactt gagcctagga g ttcaagacc   72540
agcccaggca acatggcgaa acccatctc tacaaaaaat acaaaaatta g cctggcatg   72600
ctggtgcaca cctgtagtcc cagcttctcg ggagtctgag gcaggagaat a gcttgaacc   72660
ctggaggtgg aggttgcagt gagccaaaat cacgccactg cattccagcc t gggcaacag   72720
accgagactg tctcaaaaaa aaaaaaaaa tgattttttt caagtgcttt a aatggttat   72780
gtatagtata aataatctac aatggagata tatatatata tatatataac t tgataaaa   72840
aatatggtta acaatagggg gtttataaaa acctaattat ttctgctctc a gactaatta   72900
atccttacag tcagcatgta atattagcct acaccagctc gacagacttg a tctcgttag   72960
attcatgaga tagaataaaa cttggccatt attcttcaca aagaatgatt g tggcttgaa   73020
gtttttaaaag cgcagaaata aagaaggaaa tcacaattaa acaaagccac t tttcccaat   73080
ttcaagaaat aagagctttc agaaagagtt ggcagccttg catcctcatc t ggaggctgc   73140
aggcggtgcc tcacagccct gtgcccgccc tgatactggg agatgcacct g gacttcatg   73200
gaaccctgtg ggtcatgctt ccggacctgt cggctgacac atcttgctgt g cagcttctc   73260
```

```
cacctgctct ccatcactag aagctacaat agtctttctg tttccaagga g atttgcctt   73320 tgatcagagt gccataaatg tagatggatg actaaccgag agcgcaggcc a ctcaccgcc   73380 attcctggtg ttgataaatg taccccttta ctgtccacat actccagagc t tgcagttcc   73440 ttccgctggt actcacagtt actgaaatca tgtcattagt ctcagtctgc c tgccagata   73500 tttcagatgc ctttgaaata ctgttcttgc agtagcaatt cattttttta gtgctaaaa    73560 aaaaacttgc agttttattt gtgaagtgta attttgcctg agatataaca t tttggtct   73620 gggttaaata gctcctaaat tctcaactga aatggatatc cttgaaaact g attatcaa   73680 gctcctgaga gtgaactatc accttgcttc cactaagtaa tttgtaaggt c taagatccg  73740 cagtccctgg tgttttttt tttttttttt tttttttttt tttttttggt a taagtagct   73800 ctcagacttt tacccacatg agtttccatt aaaattgtac aagctttgac t ttaaatcag  73860 ctgatgaata gaaggagttg atgtgtgatc agctggtgct attgggaaaa c tgatgataa  73920 gcagtggagc aggtaagaac gtattgttcc tgaaccattg gaggaactag c agcagtgac  73980 ctctgaggag ccctgggaac accctggagc tcctgagcaa cacgttgctt g tgatcactg  74040 acctggatat catgactgtg tgagcaacac ccccacacc tcagtagcaa a aacagagaa   74100 cagtggcagc acatcgtggg ctgactgcag ttgattctgg ctctcttaca t gagaatgcc  74160 aagtcataca agaaagtgcc tgccatgctg agcttctctt taccttcttg g gttttaatg  74220 gcattgcaag ttatcagtat aaaaactcat attagttata ctaaatagtt g gaccaagtt  74280 aagatattag gttgttatgt agtgtgcatt ttaaagtaaa acaaatgata g agcttttag  74340 aagcatctat tatgaaaatg ttccttcaag tctgtgcctt atgaatctaa t aagctttg   74400 cttttatatc aggttatctg tgctacaatt gcatttggaa tggggattga c aaaccggac  74460 gtgcgatttg tgattcatgc atctctccct aaatctgtgg agggttacta c caagaatct  74520 ggcagagctg gaagagatgg ggaaatatct cactgcctgc ttttctatac c tatcatgat  74580 gtgaccagac tgaaaagact tataatgagt aagctgggct ccattgtaga g acattctgt  74640 catcttcagc ctcatgatag tagtctactc ctgctattgt ggtacttctg g tccagtttt  74700 ccttaaataa tcgtagaaaa atagaggagt ttatacagat tggcaatttt a ttttagttc  74760 attttttatta taaaagtggt aagtgcttat tttgtaaaac tcaaatgata c agatgtgta  74820 caaggcagaa aatttacaaa ccatgccttg tagttttgcc cccaaaataa c tctagttat  74880 tggtttcctt tgtatccttt cagaccctat ttctgcatgc attcttgcat g taacacata  74940 tttcaaacat gcaggaagat aaaaaggaga aaataatgag ctgtcatata c taccatctg  75000 gattaagaaa taaaacacaa tcaatcgagc tgaacccctc ccaccaccc c atagcctct   75060 cttgtctcat ccgtcctctc ccattagagg caggcaaata tcttgtattt g gtatgtacc  75120 ttttccaaat gcacatattt taaatgtaa atgggattat attatacata c tttatatat   75180 ataatgaccc gatttttttc agtcaacagt aggatgtaat tatcattcca a tgaatacat  75240 acagcctgac tacctagaat tccgtagtat ggttattcca tggttattaa c taatcccc   75300 tcttactaga tcttgtttat tgttttcac tgttatcaac aatgcagtat t gaacatccc   75360 tccctataca aatatctttg ggcattttg cagttactta tataagattt t ttttttttc    75420 aagaccgagt ctcactctgt cacccaggct gcagtgcagt ggcagaatct t ggctcactg  75480 caacctccgc ctcccgggtt caagcgattt tctcacttca gcttccagag t agctgggac  75540 tacaggcatg tgctaccatg cccaactaat ttttgtattt ttagtagaga c agggatttc  75600
```

```
accatggtgt ccaggctggt ctcaaactcc tgacctcagg tgatccgccc a cctcagcct   75660 cccaaagtgt tgggattaca ggtgtgagcc accacgccg gccttatagg a taaatttct    75720 agagttaaac ttgctgggtg aaagtgaata catattttag aattttatta c attctttgc   75780 tcatttttct cctgggttgt gagagttaaa tatatttcct aaatatatgt a tttcttctg   75840 agaccacttt tttttttctt tttttttttt ttgagacgga gtctcgctct t gttgcctag   75900 gctgaagtgc aaaggctgga atgcaatggc acgatctcgg cccactgcaa c ctctgcctc   75960 ccagatgcaa gcagttctcc tgcctcagcc tcctgagtag ctgggattac a ggctcccac   76020 caccacaccc agctaattttt tgtattttta gtagagacag ggtttcacca t gttggccag   76080 gctggtcttg aactcctgac ctccagtgat ctgtccgcct cagcctccca a agttctggg   76140 attacaggcg tgagccacta tgcccagccg agaccacttt taaattaact c tggcagaag   76200 tacagtgcat aggaaatggc acttaccaag cactgtgccc aacactgcat a tatcacctc   76260 attaccttat ttgttcaaaa caactaactt gtgatgtaga ggtactccca t aaaagtga    76320 gcttcggaaa ggttttgtaa cttttcccca ggatcactga tatggcagga g caataagag   76380 tcgttgtagt agtagtataa caatggtaat tattatagat aagtgtttat t tagcccttc   76440 ctatgtgcca ttctaaatgc cttacatgta tcatcaacta atttcatctt c acaataacc   76500 ctcagagata aacctttgc tttcctcatt ttacagagga ggaaaatgaa a tgcagaact    76560 agtaaatggt agagccctga cagaacccaa gttcgtctga ttccaaagtc c atgttcctt   76620 gcactatacc aaagtgattc tcagtgaaga aaattaaata tttacacttg g tttgcccat   76680 ttgtgttttt tttaaaatct atattaaagc taggcccaaa catggccagg c atggtggct   76740 cacacctgta atcccagcac tttgggaggc cgaggccaaa aaaaaaaaaa a tttaggccc   76800 aaacaattta atagatattt aagtcctgat agcagcaact atttggggga a aaatactca   76860 taaactggaa gaaaaaaata atatttttta aaaattattt tctttttttt t tttttgaga   76920 cggagttgcg cttttgtcac ccaggctgga gtgtgatggc acgatctcag c tcactacaa   76980 cctccacctc ctgggttcaa gcgattctca gcctcagcct cccgactagc a gggattaca   77040 ggctcgcacc accacaccca gctaattttt gtattcttag cagagacagg g ttttgccat   77100 gttggccagc tggtctcaa gctcccgacc tcaggtgatc cgcccacctt g gcctcccaa    77160 agtgctagga ttacaggcgt gagccaccgt acctggtgtt aaaattctta a gtaacaaca   77220 gttgcttact gatggaaagt atgccactgc tgttctcaca cattggaatc a aatccgaca   77280 ctgccaccct catttcctgt ttcacattga ttttcttgag atacttcttt t tatcatagc   77340 aactgcgaaa aacccagctt tgcaaagatg agatattgct aataggaatg t agcacaatc   77400 taatgttaat accattaact acctcaagct aataatttgg gtgatgttca a cagatgtta   77460 ggcattgctg tgtttccctt catgtaaaat attctgtctc tgtgagttca c cacagcacc   77520 cccgggcttg ttggcacaca attttggaac cactggtgta actactttga c ctcagatac   77580 tcagagaagt gcatggccac tgccgtaatc tcaggctctg cttcctcagg a tgttcagtt   77640 cggtggatgc tcgactgata aatacagcaa atataagtca aaccatcatc a ttggggata   77700 atgaagattt gaaaaaaaaa aacctaacat ttattcctat agtactaaaa t cttgaggat   77760 gaacattaat actcagttaa ttataatata gaatgccatg ttgacaatgc t gttaacagt   77820 aattttctta tttaatattt aaagttatat gaatctattc taaatatttc t atgatatgc   77880 tctattttc ccctataagt atgtcttact atagtcttca tctcttttag t ggaaaaaga    77940 tggaaaccat catacaagag aaactcactt caataatttg tatagcatgg t acattactg   78000
```

-continued

```
tgaaaatata acggaatgca ggagaataca gcttttggcc tactttggtg a aaatggatt    78060 taatcctgat ttttgtaaga aacacccaga tgtttcttgt gataattgct g taaaacaaa    78120 ggtaaaaaaa gaagttttaa aattccttat aattaaattt tttatctctt a ctttaaaaa    78180 tgtagataca aattagattg caaaaggtgg tctccgacag attaacaggg g aaagacagc    78240 ttccttccag tagtaatttg gaatggaaac atttaaaaag taatttcatg c ggtatcttt    78300 tctttataat tagaaccctg ttaaaaaata taatggacat cagcatatcc a gaatattga    78360 gtttatatat gtgcactgat gattacagaa tattttagaa atattaatat g caaacatcc    78420 aaaaagatcc aacatgggca ggtagaatat tttaaattta atatattaat g ttattaata    78480 taatacatta tattaaaaat ttaattgatt aaattaaata tattaaaatt g acgtattaa    78540 tatttaatat tttaaatatt taattaatat actaaaaatc tcattctcaa a agagtaata    78600 actagtgtac cgtatgtttg aattcaaatc aattacatta ctcttttttt t taactataa    78660 agaataacag taactgcttg tggataaatt cactattatc tgtcctaaaa t accettgga    78720 aggttgttaa attcagtcat taggtactta ttttacctat cttggtaatt c tacatttta    78780 atgtctactg taacctactg cttactgagc attttcacgt ttggtgtatt a tttacctat    78840 ctgggagtat tagacttata tgtgcaagat gctggagagc cacaagtgac c atggtatgg    78900 accaattcat agactggagt ggagaccgac atacatgtgt tcatagaagt t taacactct    78960 ggcttggcgc agtggctcat gcctgtaatc ccagcacttt gggaggccga g gcaggagga    79020 tcacctgagg tcaagagttc aagaccagct tgaccaacat ggtgaaacct t gtctctact    79080 aaaaaaatac aaaattggtc ggctgtggtg gcccatgcct gtaatcccag c tacttggga    79140 agctgaggca ggagaatcgc ttgaacctgg taggtggagg ctgcagtgag c caagatcat    79200 gccattgcac tccagcctgg gcaacaagag cgaaactcca tcaaaaaaaa a aaagtttag    79260 tactctcagt aagtatagtt aaaaaataca gagcacaggg cagaacagag g gtagtctct    79320 ctcagtgtgg aactggcaaa ttcatgccat ctcctcccac cccacccat c ccttaaaca    79380 ttgctatcag ttccctcatt caacagatat ttgttgggct gtgtaacagg c actgttgta    79440 ggaatttggg atacatcact aaacaaaatg aaaatccctg cccttgtgga g cttacactc    79500 tagcagaggg aggccagtta caaacaatat acacaataaa tatacatgaa a ggataagag    79560 ctgtggtgaa tggcacagca gagtaaaaag acaggaggaa tgggtagagt g caggatgca    79620 gtattagacg gggtggtcct tggaagtcta actgagaaga tgggagctga g gaaaatctt    79680 gaagaaggga gttagctggc agctccctgg atgtgagctt tcctgcaaga a gctttggct    79740 agagcaaagg ccctaaggtg ggggtgtgcc tggtgtgttc gagagatggc a agggagccc    79800 atgtggctga gcaggattaa gagccagtga ggggaagagg tgatggagag c cagagcagt    79860 cagttgaggg ctagagtccc agagtaactg gaggcctgag taactggaag g atggagtta    79920 tccttggcta agatgcagaa ggctggttgg cagagaagat caggagtttg t tttgggtta    79980 cctaaattgg gaatctaata ttgaattaca tattaagatt caaaaattct g aaaacagac    80040 tggtggcaca tgggtgatat ttaaagcatg gccatcagct gacagtcggg a taagagaag    80100 ggacggaaga gaaaggagaa agtatgaaat agttgtctag dacagggtc a gtaaacttg    80160 cttttaaagg gccacagcat aaatattgta cacttcgcag ccatagtctc t gtcacaacg    80220 actcacagct ttgccattgt agtctaaatg cagacataaa taataaatac a ccaatttc    80280 tagtcatctt ccatggctgt gttccaataa aactttatgc acaaaaacag g catccagct    80340
```

-continued

```
cctgggccat agtttgctga cttctgttgt gagagaatgg aggaatgata g gctagggaa   80400
gtataaagat aatgattgcc tacagcatta acagtccatt cgagctttgt g gccacgtag   80460
tgacagtgaa aatgccaagt tcagccacat aggtacaggg acctatggag a tggagaatt   80520
ggatccatta tgttttgcca ggtaatatgt tgaagtgatc taagggcaag a gagctgagg   80580
gtctatgaga ggtagtgatt ataatgatcg actggaattt cagctgagtt a ggaggacat   80640
ctgaggttga ggatcagcag atgggcattc ccaggggatt gttggagtca g aataccaca   80700
tggtatgagt tggaaagata ggatgtggtg gtctgagaat ggaggagttg c cattattag   80760
taagcttaag gtaggaagtg tgagcggctg atgtatgtgg aggacaggat c attggagca   80820
gaggagatca agaaccaaaa gaccaaagta agaggatcag ctctgtatac c taatcacca   80880
agaattaagg tagatggcca ggtgcagtgg ctcacacctg taatcccagc a ctttgggag   80940
gctgaggccg gcggatcacc tgaggtcagg agttaaagac tagcctggcc a acgtggtga   81000
aaccccatct ctactaaaaa tacagacaaa ttagtcgggc atggtggcag g tgcctgtaa   81060
ccccagctac tcaggaggct gaggcaggag aatcgcttga acctgggagg t ggaggttgc   81120
agggagccaa gattgcgcca tcgcactcca gcctgggcga cgagcgaaac t ccatctcaa   81180
aaaaaaaaaa aaaattaaga taggaatgga gtgacagggc acttttctt g atgactcta   81240
gatagggcct cagaatcact tgcagttgtt agtgtaagac cagaaacctg t tcatctcca   81300
ggttattggt gtgtgcaaat gacaaggatt agaaggtagg gagggctgca t acacagaag   81360
caccaagcat gatgcagctt tttacacctg tgagtggtca gtattgatgg t agagagaac   81420
tagggggagag aaaggcaaaa agtcatctag taacggggac tctaaaaagt g ggcaaagtt   81480
tggggatagc tgaaggaaat gagaaaggaa actagcagga gatgatgaaa a gagcgttga   81540
ctatggcacc aaagacccca gaggggttag aatccgtgga tttacgtggc a ccccacagg   81600
ttcccaccca gtatgtaaca gagcactatt ctaggaggca tggaggattt a aattgtgtg   81660
tttgtgtgtg tgtctgtgtg ttatatatgt gtttctaccc acagagtgct a tcaggtagt   81720
tgaaagacaa gacgtatctc tgtgaaacag taacaacatc gagtggtagt t gttctagaa   81780
cttagataag aatgaacatt tgaaatttcc gtaggttttg gtctcggtat t ggtctggaa   81840
atgggttatg atgaatctac tatagttaat attaaaccct agtaatctag g cattgttac   81900
cttaattata gcagaaagta ttctcttttt attcatagga ttataaaaca a gagatgtga   81960
ctgacgatgt gaaaagtatt gtaagatttg ttcaagaaca tagttcatca c aaggaatga   82020
gaaatataaa acatgtaggt ccttctggaa gatttactat gaatatgctg g tcgacattt   82080
tcttgggtaa gtcatctgtt ttgaatgttt gagttacttc aattgaaatt g aacatctaa   82140
agaatttatt acaagtacat agaaaaactt tttgtctatt ttcttataaa a cttgagttt   82200
ctgaataaaa cttttaagta acaaaagaaa gtcaattatt atactgtttt a tataatgta   82260
tatgtcacta agttgagatg gtttcacata caaagaagaa aataataaag c ttatgcgag   82320
ttcatctgag tgggtggaat gtaactatta aaatgtcagt aaggaaataa a atgaggatt   82380
agacccataa cagcatagag aataggagag agactattat cagattagtg c cttaaaaat   82440
ctctcagggg ctgagcacag tggctcacac ctgtaatccc agcactttgg g aggccgagg   82500
cgggcggatc acctgagatc aggagtttga gatcagcctg gccaacatgg t gaaaccctg   82560
tctctactaa aaatacaaaa aattagccag gcatggtggc atgcacctgt a atcccagct   82620
actcgggagg ctgaggcagg agaatcgcta gaacccggga agtgaagact g cagtgagct   82680
gagatcgcac cattgcactc cagcctgggc aacaagagtg aaaccgtgtc t caaaaataa   82740
```

```
taaataaaca aacacacaca aaaattagcc aggtgtggtg gtgggcacct g taatcccag   82800 ctactcggga ggctgaggca ggagaatcgc ttgaacctgg gaggtggagg t tgcagtgag   82860 ccgaggtcac gccactgcac tccagcctgg caacagagtg agactccatc t caaaaaaag   82920 aaagaaatgg acagtaaaga ggaagaccaa ataaatagaa tatttgaccc t gggtgatag   82980 aaataattga aaatagtagt ttgggagaga ggggagagaa gactccttag t atcgtctta   83040 aagagttttt aaaataaata cttaaataat aattgaataa tggaaaagaa a taaaaatga   83100 gaaagagctg tcaattttaa atgattgaca aagtaaattt agtggagagg t tggaaaata   83160 aagtcaagaa aatttaggaa ctgatcaaaa tgatatatgg aaaatagaga a agcatagaa   83220 aggattaatc ctcagtagat gtaaaatctg acaaaaattt tggaaataga a aataaaggg   83280 aattatcaaa ccaatgatct aggaaaactt cctagagtgg aagagataaa a gttttggat   83340 taaaatgctc actgaatgcc aaataagatg cctgtaaaaa aaaaaaaaaa a aaaaaatta   83400 agacatatgg ccacgagatt tgagaatact aagagttaaa gacatgtcaa a gaggaaaaa   83460 cttttcctca accctcttag gttcagtgat ggggcctgca aattaaacca a caaaaaaca   83520 gattagcaag ggaaaagaca gatttagtca tgtgtggata ggagttcaca g aaaaatgtg   83580 gttcaaaggg gcagttagaa tgtggggctt ataccatc ttaatagagg a aggggagaa   83640 ggagggggc acttatggaa aaacaaatga ctgttaggaa agacagatgg a ctgttagga   83700 gaccagatgg gagatacaaa gttttttatga caatgtctgt ttaagtgtgg t gtgaagtct   83760 tatctctgtt taaagggtc agccttccct ggttttttccc agggaggcaa t ttatgacaa   83820 ctgagttctt ttgggaggcc ctgctttttg gcagataaga gatttcagat g ccttctgct   83880 caaaataatt tttatgccac agtggcatat tctgtacccc ttcagagaca a ttctgaaag   83940 ctctggaaag aaaacaggaa cccaaaccag actgacatca gcttaatatc a gcaatcctg   84000 gagactagca ggcaaagaaa gtgagcacag gtcgtgattt gataagtggt g gaacccacc   84060 catgggtcca gtgaagaaaa cccatagtca cagtcaggca gcagggccag t aagcaatct   84120 atgcagacta acaaaagtca ggaggaggct gggcacggtg gctcacgcct g taatcccag   84180 cactttggga ggctgaggcg gcggatcac aaggtcagga gttcgaggcc a gcctgacca   84240 acatggagaa actccgtctc tactaaaaat acaaaataag ctgggcgtgg t ggcacacac   84300 cagtaatccc agctagtcgg gaggctgagg caggagaatt gcttgaaccc g ggaggcaga   84360 ggttgcagtg agccaagatc gtgccattgc actccagcgt gggcaacaag a gtgaaactc   84420 catctcaaaa aaaaagaag gaacagggcc cacccaacgt agagagagag t aagaaagga   84480 atggttttat tgataacagt gaagaatgca aatgttaggc tcaaccaaa a aaaaggaga   84540 gaggccctta gaaactccag ggaaaagatt atacaagaga gcaagatcaa a tataaaaca   84600 aaggaagttg tggccaggca cagtggctca tgcctgtaat cccagtactt t gggaggcca   84660 aagtgggtgg ttcacttgag gtcaggagtt tgagaccagc ctggccaaca t ggcaaaacc   84720 tcatctctac aaaaaaatac aaaaattagc cgggactgat gttgtgcacc t gtaatccca   84780 gctacgcagg aggccgaggc agaagaatca cttgaatctg ggaggcggag g ttgcagtga   84840 gctaagatcg caccactgca ctccagcctg ggtgacagag caagactcca t ctcaaaaaa   84900 aaaaagttg gtaaaatgta caaaaagtc atccatttga catgatgggt a aacattctc   84960 cttttggttc cataagagtc atgacattgt tccaattagg gaaggaaatt t gtcatcatg   85020 taaacaacga ttgaaatcaa catacagacc taaacaaggt tacaggacag a acaagatgt   85080
```

-continued

```
aaatgttaat attgatgata taaaagtaaa agtacaatcg ctaaaagtaa a agaaggcat  85140 acagggaagg cttgggtact aatgacatct cacattgtgg gaaggggtag t ggtcagaag  85200 ttctattgaa agttagaaac ataattagta catgacccaa cagtatcata t aactagcaa  85260 aattcagaga agaataaaac aaagtggggg tggtatgaat gagataaaac c tcatctttc  85320 ataataaagg ggcaaggaca atagataaat gtcaggcttt tggacagaag g caagatttc  85380 aggtccttct gtgtgtaggt agccacctga agagctgaaa acaaaaactg t ttaaaaagc  85440 gattcccttg gggaagggaa ggatgagtca ggggaatgtt gcttttaatt a taaacctt  85500 ctgtctgggt acagtggccc atgtctgtaa ttccagcact ttgggaggcc a agacagacg  85560 gattgcttga gcccaggagt tcaagatcag cctgagcaac ctggcgaaac c ctgtctcta  85620 ccaaaaatac aaaaattaat caggcatggt agcacgcacc tgtagtgcca g ctactccag  85680 aggctgatgt gggaggatca cctgcgccca tgagatcgag gtggcagtga g ctgtgatcc  85740 cgccactgca cccccagcct gggcaacaga gcaagaccct gactcaaaaa a aaaaaattg  85800 tatttcagcc agctttcgta gttgtcctca gcagtaaggt tggtccatac c attcagcct  85860 atcattagca gaacggtagt tctgtttcta taatgtggcc tttcagggat a caaattact  85920 taaagaaaat tttgaataat tcaggatata tggccagaag ccatttgaaa t ggacaataa  85980 tataattatt tggaactctt taaaacagag ctaaagcttt acgtaataac c attaattct  86040 gatttttata aatgtcacaa ggtctcttaa gtagattgtt acaataaagt t gtgtttata  86100 atgaagacat tagcagtcac agcagcttat gaatgaaaca aaggatccag c caactgtgg  86160 ctctcggcta gtaagagaaa gagggaagtg tgtgtacata ttcctgtctt c atctctccc  86220 cttgagcatc ttataggggtg ttgtgctttt cttttagaat ttgaataggc t tcattagtg  86280 agggtgacaa aaagaataga cttaaatact tggattataa actagtagca g ttttgataa  86340 ccagggccag ggatcatatt tagaaaactg actgtcaaaa attgtttgta g ccaggctca  86400 gtggctcatg cctgtaatcc caatactgtg agaagccagg gtgggaggac t gcttgaggc  86460 caggagttag agaccagcct gagcaatgta gtgagaccct cgtctctaca a aaaaattaa  86520 atattataaa ataatgtaaa gagtgtcatt ggattgtttg caactcaatg g ataaatacc  86580 tgagggaatg gatggcccat tctccatgat gtgcttactt cacactgtat g cctgtatca  86640 aaatatctca tgtactacac aaatatatac acctactatg tacccacaaa a atttaaaaa  86700 ttaataaata ctagatgcac ttaaatattt aaaattttta aattaggtga g tgtgatggc  86760 ctgcacctgt tatctcagct agtcaggagg ctgaggcagg aggatcactt g agcccagga  86820 gtttgaggct gcagtgaacc atgattgcac cactgcactc caacctccac a atagagtga  86880 gaccctgtct ctaaaaaaaa aaaaaaaat gtagataagt aatgcacagt t atcctaata  86940 catagcacag tgataggaag ctattatggt ttatgtaaac tctttctttg a tttatttgc  87000 tccaatataa ttttgctgct gttttttgtc catgtgtatt gtaaaaagat a aggaaaagt  87060 acatacaacc atagaaattt tagcgttcta ctcaaatact ctcatttaac a gaatgagt  87120 gtctgtgcca ggggtttgtg atctattcca tctgtccaaa cctgtccata a atgactttt  87180 tagcctcttc tatttgaggg tgatgatata cgtacattta ctcatcttac t tcctgtatc  87240 ttcttatcag ggagtaagag tgcaaaaatc cagtcaggta tatttggaaa a ggatctgct  87300 tattcacgac acaatgccga aagcttttt aaaaagctga tacttgacaa g attttggat  87360 gaagacttat atatcaatgc caatgaccag gcgatcgctt atgtgatgct c ggaaataaa  87420 gcccaaactg tactaaatgg caatttaaag gtatagtatt tttcatgttt a ttttattat  87480
```

```
ctcacaatga gtgaaccaaa atatattatt gtgaagtata gtgtctttgt c caagcttat   87540 agatactgaa tttatatata ctgttctata cgaacatatt ctgttttttct t aaattggaa   87600 agagatctta aaattcaacc caagtaatat gacacctgtc aaaagtaatt t aatgggtta   87660 tcaggtcact aaatctttat atattcatta aagaagcatt tatcaagagg c tattctatg   87720 cttgacactg gagatacaaa gatggagaat gcacagcccc tgttcccagt g ggctcacta   87780 tctgcatgac agaatagaat taccccccaa aaatgcaatt aagcattaaa t aaagcccct   87840 gtatgggtac aagtgcacat atacccactc ctatgatttg tttctctctc a taaaggtag   87900 actttatgga aacagaaaat tccagcagtg tgaaaaaaca aaaagcgtta g tagcaaaag   87960 tgtctcagag ggaagagatg gttaaaaaat gtcttggaga acttacagaa g tctgcaaat   88020 ctctggggaa agttttttggt gtccattact tcaatatttt taataccgtc a ctctcaaga   88080 agcttgcagg tgggtacaca tgtatccttt gttacgtggc acagattaat a ggccgaaag   88140 ttaatcttgc tagggaactc cttaagtgat aaatatatct cagtggtttg t ttcttttttg   88200 gggtttgttt tgagacgggg tctcgctgtg tcacccgggc tggagtgctg t ggcgtgatc   88260 atgactcact gcagcctcaa ccttctgggc tcaagtgatc ttcccacctc a atttcccaa   88320 gtagctggga ctacaggtac acaccagcat gcccagctaa ttttttgcatt t tttcgtaga   88380 gacagagttt caccatgttg gccaggctag tctcgaactc ctgacctcag g ttatcccct   88440 tgcctcagcc tcccaaagtg ctgggattac aggcatgagc caccgcatcc g gccggatta   88500 ttgtaatttc taaaacgaga cattacttca ttatttgtgc tgattatttg c ctgctttgt   88560 agtgtttagc tgtgttatgt acaaatatct gcaacctccg cctcctgggt t caaacgatt   88620 ctcctgcctc aacctcccga gtagctggga ttacaggcat gcgccacca t ttactttga   88680 ttatatgtat ttttcatata ggcacagagc tgtggataat aaaaatcaat g tccaaatca   88740 gtaaaaaaaa ttcttttcaat aaaagcactg tgtcatagtt taattagcag a attttttttt   88800 tccttaatag tccataaaat aacggttttct taaaaaagtt ggcatcttag a tccaatgaa   88860 atattgtaat gaccaattgt aatattgtaa tgggctgggg gccatggctc a cgcctgtaa   88920 tccctgcact ttgggaggct gaggtggacg gattgcctga ggtcaggagt t cgagactag   88980 cctggccaac atggtaaaac cccgtctcta ctaagaatac aaaaattagc c aggcgtggt   89040 ggcgggcgct tgtaatcccg gctacttggg aacctgaggc aggagaattg g ttgaaccca   89100 ggaggtggag gttgcagtga gccaagatcg tgccactgcc ctccagcctg g gcgacagag   89160 cgagactcca tctcaaaaaa aaaaaaaaag tctgcaatga agagctagtt t ccttatgaa   89220 gagattatgt tttatgcttc tttgaatctg gatctagcac actgctatgt c tttagttaa   89280 taaatactta ctggtctgag ttatttccat gggcagatag cccaacccag a atttcagta   89340 gtagagttcc tggaaaacaa cgtcttcata tagttggcca gctgggctat a ttaccttcc   89400 atattcttct tcataaaatc tcataatcat caccttctct cttcttcatt c cctctccta   89460 cgataatcgg tcattacaat atttcactga ctctaagatg ccaactatat t aagatactg   89520 ttactttatg gactattaag gaagaaaaaa ttctgctaat taaactatga c acagtgctt   89580 ttattgaaag aattgttttt tactgattta gacattgatt tttattatcc a cagctgtgt   89640 gcctatatga aaaatacata taatcaaatt accgtagtac ttataaaagt t cacattcaa   89700 agcctgactc ttctgagtca cttttttgact gagtcgtcca tgtctttgtt t ttccctatg   89760 tcatcactaa cattctcatt agccataagg catttccaga gtgttccact a ttttcccca   89820
```

```
ggatttaatc gaaatctctg ttatcagttc tgttttgaag gtggtggttt c ttgatgata    89880
ccagaaggtg tcaacagaag gttgtacatc tctcagtaac aaaaatgtag t gcggcctca    89940
tctactttgg gcatcttctt tcttaggtca cgtaaagcac ttggttgtac t tgcgagaaa    90000
ctatggaatt gggggcctgt gtcctcagag acaaatagtg cctgggtttt t tttgttttg    90060
ctttgttttg ttttttttgga gataagatct tattctgtcg cccaggctgg g tgcagtggt    90120
tgaacacagc tcactgcagc ctagacctcc tgggctcaag tgatcctcct a ccccagctt    90180
cctgagtagc tggaactaca ggcatgtacc accatgcttg gctagctttt t tattttttt    90240
gcagagacag ggcctcactg ttacccagac tggtctcata ctcttaggct g aagcaatcc    90300
gccctgtctc agcctcccaa agtattggga ttacaggcat gagctaccac g ctcagccag    90360
atagtgcttt tcttaatacc aaatgtattc cctgctactc tgtttcagaa c ttttctgca    90420
ttcacaatca ctttttaat gctaatcaca gtatagtctt tttgaagaca t gtcatggca    90480
gttagactca atacatgagg tacaaacagt gcagtgactt tgttgacatg c tgacagtac    90540
taatagctat gactaagttc tcacaagcat gagcagtaac aaccgcaagg c agctgccat    90600
ttagccatca gcagttctaa gacatatctt gacctcagga atgctaaatt g tgaaaaggt    90660
gtgtgtctta gaattgatga aatttggtat tttatgatat gttatttcta g gcgattagt    90720
gtagtttctt aactgtcctc cttacctcca gctgtgaatg tgatgtacat t ttaatcttt    90780
caaaacctag taaaactaca acagcttccc agataaagta tacattttat c aagggtcta    90840
catttcttcc tgcctctcct actttatctt tcattaaacc cccttcataa a ccttctgtt    90900
ctgtccacag tctcttgctt ttcctctaaa catgggaatg atgtgaaaat c acagatggg    90960
aaaggatttg aaatccactc tttgctcagc tcaaatacat aggaatggtt a ctccctcac    91020
tacccagagc cagtgcatca gtcagtccta cagagccagc ctccaaaact c acccaagct    91080
tgcttcactg tgtctccact actgcattcc agttcactcc atcctcactc g ctcctgcaa    91140
tggcttccac caggctcccg gattctactc tttcctttac agtcaagttc t taaacagca    91200
gccagggtgg cctttaaatg acaggcttgt ctagctgcaa gactgatatg c gacctctat    91260
gcagaggact cagctggctg cttgttgcct caaccccat ggggaaagag t ggaggaaga    91320
aaagtttgtg ctggaggaag taacaatttg gttatgccat ctagggtggg g tgtacaagt    91380
ctggagtgca gagaagaggc tggagctgga aatagaaatg cagcgttctc a gtaaagaga    91440
gggcacacca gtctcagcta gatgagtact ggccatggga acagtgggca a gagcagatc    91500
tgctccactc cacgcacatg gcacaggtcc caccctcagc ttcctcctgc c ctggctctt    91560
gcccttgctc tgcccctggcc tatgccgctg gaattggatg gtgggttcct g ccctctgtg    91620
cctgtctgct gcctctgagg tgctaacttt gccttttaca aaattggcct g tgttcccag    91680
taccctgcag ttagttggca cttagcagac gtgtgctgaa tgcgtgaatg a gcctgaatt    91740
cagtgggttt tctatgggtg ataatttaaa ttcctaattt tatgcctttg c acagaatct    91800
ttatcttctg atcctgaggt tttgcttcaa attgatggtg ttactgaaga c aaactggaa    91860
aaatatggtg cggaagtgat ttcagtatta cagaaatact ctgaatggac a tcgccaggt    91920
tagtacacag ccatgtgtgt tctctaaaag cctgtttaat gtgaagcgac g cgtctcact    91980
gaattagaag gatgcagttg tgtgaatgct tcctacacct cgtcacactg a catccaagt    92040
cagcccccag tggtgtgcca gtcacctctg agaggacact agtgcttatg c ccctgtga    92100
gtgccagttc tgaacttact cataggatcc aaaagggac ctttgggccc a ggggttgct    92160
ggttcccgta atgcaagtgc tcaagggatc agagccctgg gtgccagttc c agatctgcc    92220
```

```
accacgtcat gctgtgtggt ctctagcagg ccaccaatag cctctttgtg a atcaggttc   92280 ctccaccaag gaaggaacat gttatctgac aaacatgtct aaagataaaa t ttaagacta   92340 gtgtttaaat gttttggaga aatgagcatg cagctagaat gttattattg t tagtcattg   92400 atagaacctg cctgagtgca tcattatcag acgttcccgg agtcacgtta g gcctgtcct   92460 gtggcacttc taatcatgag cttcatcatc attacagctt tagaaatcat t gacctgggg   92520 gaaatgagaa caacaaagca ttttgttgta ggaaatattg agagcacaga a gtcttctgc   92580 cctctgataa catcaccacg taataggaca caacagacag gcccggttca g tgttcttcc   92640 tgcttccaga caggcagtgt gggggtcttc ccaaggatga tggaaatgat g agcaggatg   92700 agatagttca agttctctct ttacctagtc gcttttttttt tttttgaca g agtctcact   92760 ccaggctgga gttcagtggc acaatcttgg ctcactatgc ctcccagatt c aagcaatta   92820 tcccacctca gcctccccag tagctgagac tacaggcatg caccaccaca c ctgacttat   92880 ttttgtattt ttttggtaga gatggggttt cactatgttg gccaggctgg t cttgaactt   92940 acgacctcaa gtgatccacc tgcctcagcc tcctgaagtg ctgggttac g ggagggagc    93000 caccacacct ggttaggttc tcctaaattc ttccatatgg taattagtcc a ttaaaagcc   93060 ttgttccgaa tacattttga cagtgagcca gggttggagc agccatggtg g agtcctgtg   93120 ccctccatgc tgctcctgta gggtggcctg taggacaagg cagaccagcc a ggaaatgga   93180 gactgggtcc ccgtgtgacc tatctatagg gaggtttcat gcttttggg t gccttggga   93240 tgcaaatact tatggaaatt accatcttct ttgcaaatgt gtgctttcat g cggtctcac   93300 ctcccgcata atatgtgaca tgttcagcca tattgtgcaa agacaagttt t tttgtctgt   93360 aaagagtaaa ataggatcta gaattttctt atgttcattt actaagaaac t attgttcaa   93420 agatgagata caggaccgtt tgtttcccctt atattgagct gatttttca g cacatttaa   93480 aataagtaaa attgcctgcc atctttatag cagttgatac ttttttgaatt g cctaccaga   93540 actaactgcc caatcaacaa caggaacaca ggccatatgc gacagtatga g ctaaacctc   93600 atgtctctag ttaacttcaa gactatcaca aattttttta atgaattctg a ttctctttt   93660 gttaaaaatg aattgccatt gaacactttg gggcttgtg cagtaaaaaa a ggtttggtt    93720 cttgctgaat tgttgaatcc atatggcagg gaagcagcta ggtatctgct a aaatgggcc   93780 cctgcagcgt gtctcttcat atacactaaa aacacgtgga ccagtgcgac a tcacctgta   93840 aacatctgca ttttccattt gtagctgaag acagttcccc agggataagc c tgtccagca   93900 gcagaggccc cggaagaagt gccgctgagg agctcgacga ggaaatccc g tatcttccc    93960 actactttgc aagtaaaacc agaaatgaaa ggaagaggaa aaagatgcca g cctcccaaa   94020 ggtctaagag gagaaaaact gcttccagtg gttccaaggc aaagggtat g ttttgtgac    94080 atctttttca atatagggaa caggggaaga aaggacaaaa gtgcaacagc t ctgccttgc   94140 tttgaaggat ttattaaaat aagccattat taaatattgc taatggaatg a cagttgtta   94200 atggagtgac aattaaggtt tgatccaaaa caaaatatt tgcttcaaga a acaacaaaa    94260 aatatttgct tcagatgttt aaaacatcta ctgactaata gttatgacta a agttttctt   94320 tcttttttta atttgaggac aaagtctgac tctgttgccc aggctagagt g cagtggcac   94380 aatctcggct cactgcaacc tctgcctcct gtactcaagt gatcctccca c ctcagcctc   94440 ctgagtagct gggactccag gtgtatacca tcactcctgg ctaattttg t atttttgt     94500 acagatggag tttcccccatg ttgcccaggc tggtctcaaa ctcctgagct c aagtgatca   94560
```

-continued

```
gcccactttg gtctccccaa agtgctggat tacagacgtg agccaccgca c tcagcctga 94620
ctaatgtttc ttgtttgcaa agatgtcttc catgttgatc ttcccttaga t atttgtttg 94680
cctgtttggg atgattgttc ttcttaagag acttttccac ctacaatact a taaatcata 94740
cactagctga ataaataaca aagggttttg tgtcctcgtg gcttttacta t tctgtcagt 94800
acttgctccg ctgcttttat tgctgcagaa tcccatggat ctccaccttg a ggcacgtgc 94860
acactccctg cctttcatta acacctggga gaatcgacct cccagccttt g caggggtag 94920
caagaagaag ccacaacaga gaaaccaaaa gttcagtcaa gccaggcctc t ttaggggtt 94980
gcgtaaatgg cttctgtctt ccccttccca tgttttcctg ggccgctcgt c tgggacatg 95040
tctgttctgg gcgctttctg cacaccaggg gaacaacaaa gacagcatgg t ctgatatgt 95100
gtgatgatct tggcagtttc cttctttctt cataattgca ttgtttctga c agccgcttt 95160
tcgattttct gccagggcac cctctgcctt ctggctagta ggttaggcct g gcaggaggg 95220
agaccattcc atcagtcttg agaacttgac cccaaagtaa ctgtatattg t aacagagtt 95280
gcttgcagaa aaagaaacc aaaaaaagt ccacagtcaa cttttgcaag c tgttgtgtt 95340
ttcttttgca gttttctac ctcttgtcct tctgagtaat aaaaaacaag a actgagtgg 95400
ggaaagagaa aggaaggcag acattaccaa attgtcattt tcttgttaag t ccataaaca 95460
aaatcttgta tgtgctaatc ctcctgccag agtaccgaaa ttaaaggcat t agaaaacgt 95520
tagtttaatt ttgtggtttt gagtgcgcaa gtgatcagta agtgctcttc a gtgagaaca 95580
ttttcttatt tccatcattt attcctccac tttgggaaat actcatttcc t cagtaactc 95640
acacagagcc ggagacctta aaaggcatct ggctcaacac cccgggtttt t gaagaggaa 95700
gcttaggcct ggcctgggga gggcttatcg gaggacaacc ctgcctggtc t cgatttcaa 95760
aggtagaagc ggacactggc ctgcccacac ctgcccagag cacgttcact t ctgcatgtt 95820
gcctgtggag actcctaaaa aacacgcatg gtcttccatc tcatctttat g tattagaac 95880
aaagcaaacc atattgctat tggctccctt atttaatttt cacaactttt g ttcgtaaga 95940
gtgaagcact ttgcagcatc atctggaacc taatctgata agaagcagta a agctcacac 96000
ttgtacccat ttccatgctt gttttcagtg agcctgggtg tttaagatgg g atttgttgt 96060
tgttgttgtc gttatggagt tttgctcttg tcacccaggc tggagtgcag t ggcaccatc 96120
ttggctcact gcagcctctg cctcccgggt tcaagctatt ctcctgcctc a gcctcccaa 96180
gtagctggga ttatgggtgc acgccaccac gctgggctaa ttttttgtatt t ttagatggg 96240
gtttcaccat gttggccagg ctggtctcga actcctgacc ccaggtgatc t acccaccttt 96300
ggctcccaaa gtgccgggat gacaggcgtg agccactgtg cccagccaag a tgggattct 96360
ttttaagcc ctaccagcta aagccagtgc actgtgtgac tttgtgttac c cttggagca 96420
gcctctttt gctccactct cctttccacc gacccagtct gctccccgga t tgagagtcc 96480
ctgtgcagtg aaagaataaa tgtggctctc tgccagcaac ctcacctccc c accctaccc 96540
tcagagtttc acatcttcag aacaacacac aatgaaccag ttgtgttctg g gctctctga 96600
gtgggagtaa atggatggcc caggtgaaat ggaggctgct gttggccgat t cattctgta 96660
aatcaacata aacagcaggt tttctctctg ggcttaattt ctcagcagga a atcagcata 96720
gggaaacttc aggctgcatc tctgccagtc tagcagatct ctgccagttc t gcagtaaaa 96780
ctgccttgga gccagagttt aagtcatgga gctccatcag aatgtcatta c ccacaggct 96840
gtggccctat accctcaatt cagacgggag gctacttgta tgccctggtg c cgtggaatt 96900
agtgtggggc ctgacatcag ccggttacag agcagcagga aaggcttctg c gggtaatgc 96960
```

```
tgcccacagc catcactgta acatgccgg ccccatggtt ttgtttgttt t tatttcatt    97020 taagggtggg aagggagctg ttatcttaag gtctgcaagg aaagtgagat g ctggaagga   97080 cttggtaatc ggctctggcg gcttcttcct tggctttaga aggcagcgag t gggagggag   97140 agctggcaga tctctgggtg taggcaggtg agccagggag ctgctggaca c ggtcctaac   97200 agaaggccgc atctgcagcc ttcctgggc ttcctggggc tggccaggaa g acgcccagc    97260 tttgccactc ctggccaccc agctccaccc catgcatgct caccccacag c tgccttgct   97320 ctggactgtg caagtccagt cattccgggg tgcctatcag cagggagctg g ggccttaca   97380 gcaaggtgtt tcacttcttt tatttggtca gaatagatga ggacatgtgg a cctcagctc   97440 ctcttgcagg ctctggttgt aggctgccga aggtgtgggt ggagagaggg g cggtgggtt   97500 ggtcacaagt cagaaaatta agaaacagtc ctgcacattt cagaaagaca a atccagaac   97560 aaatttatat gaagggccgc ggtcctttat tccataagta gtaaaggaaa c ttaccttac   97620 ctaggggct cgtaggcaga aaatgcacaa ggacacatta ggcccaggga a gtggtattg    97680 tagctctgtg caggttgaga ggaagaaggt cattcatttt tggtttcatt t aacattttg   97740 atttttttct ttgtcacatt tcaggggtc tgccacatgt agaaagatat c ttccaaaac    97800 gaaatcctcc agcatcattg gatccagttc agcctcacat acttctcaag c gacatcagg   97860 agccaatagc aaattgggga ttatggctcc accgaagcct ataaatagac c gtttcttaa   97920 gccttcatat gcattctcat aacaaccgaa tctcaatgta catagaccct c tttcttgtt   97980 tgtcagcatc tgaccatctg tgactataaa gctgttattc ttgttatacc a tttgaagtt   98040 tttactcgtc tctattaata tttaaataaa tgctgggggg tgatagttct t cttttttaaa  98100 ataaacattt tcttttgaat aagcatgttt tgctgccgct gcaagtgttg t ggccgttgt   98160 ttctcagaac gtctgaggca gcagctgaat catctcagtg caagagcttc t gagcataac   98220 acgaaaccca gaagccaaag gaagagccac gcgtgggccc ttgtgaaact a aagcttttc   98280 gtgtaagaca acacaaacaa aatttaaaga caaatgacgg ggaaaagagg a gaaaatata   98340 ttacaaagga ttagtatcca tcataccaaa tacccgtgaa ccagtcagaa a catcccagg   98400 gggcaggtgg accaaggatg tgaacaggct agtctcagaa gaagaaatac a catgctcat   98460 ggcccggcac tgtggctcac gcctgggatc ccagcacgtt gggaggccga g gcaggtgga   98520 tcacgaggtc aggagtttga gaccagcctg cccaacatgg tgaaacccg t ctctactaa    98580 aaatacaaaa attagccagg cgtggtgtac aggcacgcct gtagtcccag c tactcagga   98640 ggctgaggca agagaatcgc ttgaacccag gaggcggagg ttgcagtgag c cgagatcgt   98700 gccactgcac tccagcctgg gtgacagagc aagactccgt ctcaaaaaaa a aaaaaaaa    98760 agaaatatac atgctctgca aatatgtgaa aaggtcaat ctccatgaat a aaaatatga    98820 taaaaccatg tgagaccatt cttttgccta caaattatca acactggata a tatcccagt   98880 atttggggtc agcgagaaag attggcagat tgtttgggtg gacgtgtgtg g cagttgctg   98940 tagtcctttg gtattgtggt ggcctcgttt ttcaggatgc tccataatgg g ccaattggc   99000 cccagcatct ttggtaggat tttggcctct cttgcctgaa ctccagtggc c ccattttcg   99060 gagacatgcg tttctcagct gtaggtcacc tttgtctggg tgccacacag c gaggaagtg   99120 gcataagaca aaacacacac ctcggcctgc cctttgtgtg gtgttacctg t gacgttact   99180 caggagggtg tagctgggga gaccctgcct gtgccaaagc caaaggtgtg a agaggggt    99240 tgatgggaag ccgtgtggcc tctgcctggg gactcagtcc tgagagggac c ctgcaccca   99300
```

-continued

```
ccctgaggac ccaccettgt ggtagcacac tgacttcctg cctcctcggc t gcctgtgag    99360 ccccaactgc cgcctgtggg cttttggctc cgtgtttaat ggggggggact g gccaggcga   99420 gtttgctgag ggctgagtgc cattagcacg gatgcgttcc ggatctgaca t tttcagagg   99480 tcatccttct ggccagaaga                                                 99500
```

```
<210> SEQ ID NO 11
<211> LENGTH: 630
<212> TYPE: DNA
<213> ORGANISM: Homo sapiens
<220> FEATURE:
<221> NAME/KEY: unsure
<222> LOCATION: 450
<223> OTHER INFORMATION: unknown
<221> NAME/KEY: unsure
<222> LOCATION: 517
<223> OTHER INFORMATION: unknown
<221> NAME/KEY: unsure
<222> LOCATION: 555
<223> OTHER INFORMATION: unknown
<221> NAME/KEY: unsure
<222> LOCATION: 626
<223> OTHER INFORMATION: unknown
<223> OTHER INFORMATION:

<400> SEQUENCE: 11
caaactggaa aaatatggtg cggaagtgat ttcagtatta cagaaatact c tgaatggac    60 atcgccagct gaagacagtt ccccagggat aagcctgtcc agcagcagag g ccccggaag   120 aagtgccgct gaggagctcg acgaggaaat acccgtatct tcccactact t tgcaagtaa   180 aaccagaaat gaaggaaga ggaaaaagat gccagcctcc caaaggtcta a gaggagaaa   240 aactgcttcc agtggttcca aggcaagggg ggggtctgcc acatgtagaa a gatatcttc   300 caaaacgaaa tcctccagca tcattggatc cagttcagcc tcacatactt c tcaagcgac   360 atcaggagcc aatagcaaat tggggattat ggctccaccg aagcctataa a tagaccgtt   420 tcttaagcct tcatatgcat tctcataacn accgaatctc aatgtacata g accctcttt   480 cttgtttgtc agcatctgac catctgtgac tataaanctg ttattcttgt t ataccattt   540 gaaagttttt actcntctct attaatattt aaataaatgc tgggggtga t agttcttct   600 tttttaaaat aaacattttc cttttngaat                                     630
```

```
<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 12
ctaagaaatc tgtatagcta                                                 20
```

```
<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13
ttttatgcat aactaaactt                                                 20
```

```
<210> SEQ ID NO 14
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 14
gccactaagt ttatggtaat                                               20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
tgcgtgccat caagcccagc                                               20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
taggattaca ggtgtgagcc                                               20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
aatcagctgg ccatggtggc                                               20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
tcttgaactc ttgacctcag                                               20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
gcgactaggt aaagagagaa                                               20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
```

-continued gtcctacagg ccaccctaca                                                    20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
ctcctagcgg acggaaccag                                                    20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
cctcgcacgc agactcctag                                                    20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
aacagcagcc ataatcctcg                                                    20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
agtgaaacct gaaaattttg                                                    20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
actaaattct aatttcttga                                                    20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
tatcaaagtc atccatatca                                                    20

<210> SEQ ID NO 27
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 27
tcttctggag aaggtggaac                                               20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
ctttaacgta ctaaggcatt                                               20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
catcacatga ataagctgct                                               20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
gtgctccatc acatgaataa                                               20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
acagatgtgc tccatcacat                                               20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
atcaagtgaa tcaggcctgt                                               20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
acttacaaag gacttctgta                                               20
```

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
agttgctact tacaaaggac                                                    20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
tcagcccagt tgctacttac                                                    20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
tggtgtttca gcccagttgc                                                    20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
tcatcatcat caaagtcatc                                                    20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
ttcccagtca tcatcatcat                                                    20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
ctgtggaaga tttgctggct                                                    20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
attctgaatt gactctgaga                                                                20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
gctgacttgt cagtataatt                                                                20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
gattagttct aaaattatgc                                                                20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
ctagctgatt agttctaaaa                                                                20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
gatcgcctct agctgattag                                                                20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
cagcattgat cgcctctagc                                                                20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
ccagtcggca tcaggataaa                                                                20

<210> SEQ ID NO 47

```
-continued

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
acacaggcag ggagctggta                                               20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48 tgacccagg agaaacacag                                                20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
tctcaaggga gaaatgacaa                                               20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
agcttttgga cttgatctac                                               20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
ggaagtcagc ttttggactt                                               20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
cctgtcagat atgtagctgg                                               20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
```

```
agcttctgag tcagtcttat                                              20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
aaaacgtgcc aagagcttcc                                              20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
gtaatcttga cgaaaatcat                                              20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
ggaaacttct ggcgaagcat                                              20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
aacagaagga aacttctggc                                              20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
ttcagctgag tcaggatgtc                                              20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
gctcatgcta aacacctgag                                              20

<210> SEQ ID NO 60
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 60
tgttaaagct catgctaaac                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
cctgaatcat atgggtggtg                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
ggagaggcag taaattatcc                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
cacagataac ctgacagcca                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
atgaatcaca aatcgcacgt                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
gagatgcatg aatcacaaat                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
tttccccatc tcttccagct                                              20
```

```
<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
gtgagatatt tccccatctc                                               20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
cagtctggtc acatcatgat                                               20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
acagtaatgt accatgctat                                               20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
atcctttgtt ttacagcaat                                               20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
caagaaaatg tcgaccagca                                               20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ctcttactcc ccaagaaaat                                               20

<210> SEQ ID NO 73
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 73 gcttttaaa aagtctttcg                                           20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
tgatatataa gtcttcatcc                                          20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
tggtcattgg cattgatata                                          20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
taaagtctac ctttaaattg                                          20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
tgtaagttct ccaagacatt                                          20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
attgaagtaa tggacaccaa                                          20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
agataaagat tctgcaagct                                          20

```
<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
gatcagaaga taaagattct                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
tgaagcaaaa cctcaggatc                                              20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
ctgtcttcag ctggcgatgt                                              20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
attcggttgt tatgagaatg                                              20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
gtcagatgct gacaaacaag                                              20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
cacagatggt cagatgctga                                              20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide
```

-continued

```
<400> SEQUENCE: 86
tttatagtca cagatggtca                                                    20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
ccagcattta tttaaatatt                                                    20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
acaaaggtga cctacagctg                                                    20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
gtgagcaatt ctgtgccact                                                    20
```

ANTISENSE MODULATION OF RECQL2 EXPRESSION

FIELD OF THE INVENTION

The present invention provides compositions and methods for modulating the expression of RECQL2. In particular, this invention relates to compounds, particularly oligonucleotides, specifically hybridizable with nucleic acids encoding RECQL2. Such compounds have been shown to modulate the expression of RECQL2.

BACKGROUND OF THE INVENTION

Genomic integrity is critical to the health and survival of any organisms and cells have evolved multiple pathways for the repair of DNA damage.

One class of enzymes involved in the maintenance of genomic integrity and stability are DNA helicases. These proteins play important roles in DNA replication, repair, recombination and transcription by unwinding duplex genomic strands allowing the repair machinery access to damaged or mispaired DNA. For example, the RecQ family of helicases has been shown to be important players in linking cell cycle checkpoint responses to recombination repair (Chakraverty and Hickson, BioEssays, 1999, 21, 286–294; Frei and Gasser, J. Cell Sci., 2000, 113, 2641–2646; Wu et al., Curr. Biol., 1999, 9, R518–520). More recently, these helicases have been implicated in the process of posttranscriptional gene silencing (PTGS) (Cogoni and Macino, Science, 1999, 286, 2342–2344). In this process, the helicase is required to separate the double-stranded DNA (dsDNA) before any hybridization and silencing mechanism could be initiated.

The RecQ family consists of five members and can be divided into two distinct groups according to whether they contain an additional carboxy- or amino-terminus group. One class containing the longest members of the family include genes known to be defective in several syndromes including the BLM gene in Bloom's syndrome, the WRN gene in Werner's syndrome and the RECQ4 gene in Rothmund-Thompson syndrome. Mutations in these genes lead to an increase in the incidence of cancer as well as other physiologic abnormalities (Karow et al., Curr. Opin. Genet. Dev., 2000, 10, 32–38; Kawabe et al., Oncogene, 2000, 19, 4764–4772).

The second class contains the RECQL gene and the RECQ5 gene which encode little more than the central helicase domain and have not been associated with any human disease.

RECQL2 (also known as RECQL3, BLM, BLS and BS for Bloom's syndrome) was originally identified by a novel mapping method linking the gene product to the genetic disorder, Bloom's syndrome (Ellis et al., Cell, 1995, 83, 655–666). The gene was identified by direct selection from a cDNA derived from a 250 kb segment of the genome to which RECQL2 had been assigned by somatic crossover point mapping. Since then, it has been confirmed that mutations in the RECQL2 gene are responsible for Bloom's syndrome. Bloom's syndrome is a rare recessive disorder associated with growth retardation, immunodeficiency and increased risk of malignancy at an early age (Ellis and German, Hum. Mol. Genet., 1996, 5, 1457–1463).

Disclosed in the U.S. Pat. No. 5,824,501 are the nucleic acid and protein sequences of the RECQL2 gene as are the sequences of mutated forms of the gene and vectors encoding said forms as well as cells that stably express said vectors (Ellis et al., 1998).

It has been demonstrated that the RECQL2 gene product colocalizes with some telomeric clusters suggesting a role in maintaining telomere length and/or structure (Yankiwski et al., Proc. Natl. Acad. Sci. U.S.A., 2000, 97, 5214–5219).

Mouse embryos with a targeted mutation in the RECQL2 gene are developmentally delayed and die at embryonic day 13.5 (Chester et al., Genes Dev., 1998, 12, 3382–3393.). Viable mice with targeted disruptions of the RECQL2 gene have been produced and, in those lacking exon 2, show a greater predispositon to cancers (Luo et al., Nat. Genet., 2000, 26, 424–429).

While mutations and targeted disruptions resulting in altered protein expression in the RECQL2 gene are responsible for Bloom's syndrome, the normal function of the RECQL2 gene product and its regulation are still unclear. It is, however, believed to be involved in a DNA surveillance mechanism and is therefore a potential therapeutic target in conditions involving the production of aberrant DNA products, including the recognition of foreign DNA products as is the case upon viral infection.

Currently, there are no known therapeutic agents which effectively inhibit the synthesis of RECQL2. Consequently, there remains a long felt need for agents capable of effectively inhibiting and/or modulating RECQL2 function.

Antisense technology is emerging as an effective means for reducing the expression of specific gene products and may therefore prove to be uniquely useful in a number of therapeutic, diagnostic, and research applications for the modulation of RECQL2 expression.

The present invention provides compositions and methods for modulating RECQL2 expression

SUMMARY OF THE INVENTION

The present invention is directed to compounds, particularly antisense oligonucleotides, which are targeted to a nucleic acid encoding RECQL2, and which modulate the expression of RECQL2. Pharmaceutical and other compositions comprising the compounds of the invention are also provided. Further provided are methods of modulating the expression of RECQL2 in cells or tissues comprising contacting said cells or tissues with one or more of the antisense compounds or compositions of the invention. Further provided are methods of treating an animal, particularly a human, suspected of having or being prone to a disease or condition associated with expression of RECQL2 by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding RECQL2, ultimately modulating the amount of RECQL2 produced. This is accomplished by providing antisense compounds which specifically hybridize with one or more nucleic acids encoding RECQL2. As used herein, the terms "target nucleic acid" and "nucleic acid encoding RECQL2" encompass DNA encoding RECQL2, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of RECQL2. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding RECQL2. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a ene encoding RECQL2, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent o the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U.S.A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochemn.*, 2000, 286, 91–98; Larson, et al., *Cytomnetry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppi.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term oligonucleotidell refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'–5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'—O—$CH_2CH_2OCH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'—O—$CH_2$—O—$CH_2$—N($CH_2$)$_2$, also described in examples hereinbelow.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'—O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687, 808, those disclosed in The *Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937). Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimericl" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of RECQL2 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding RECQL2, enabling sandwich and other assays to easily be constructed to exploit this fact. Hybridization of the antisense oligonucleotides of the invention with a nucleic acid encoding RECQL2 can be detected by means known in the art. Such means may include conjugation of an enzyme to the oligonucleotide, radiolabelling of the oligonucleotide or any other suitable detection means. Kits using such detection means for detecting the level of RECQL2 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate,. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly (methylcyanoacrylate), poly(ethylcyanoacrylate), poly (butylcyanoacrylate), poly(isobutylcyanoacrylate), poly (isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. applications Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 µm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., *J. Pharm. Pharmacol.*, 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$S found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506, 351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2,2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl₃ (700 mL) and extracted with saturated NaHCO₃ (2×300 mL) and saturated NaCl (2×300 mL), dried over MgSO₄ and evaporated to give a residue (96 g). The residue was chromatographed on a 1.5 kg silica column using EtOAc/hexane (1:1) containing 0.5% Et₃NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in CH₂Cl₂ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO₃ (1×300 mL) and saturated NaCl (3×300 mL). The aqueous washes were back-extracted with CH₂Cl₂ (300 mL), and the extracts were combined, dried over MgSO₄ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites 2'-(Dimethylaminooxyethoxy) Nucleoside Amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O²-2'-anhydro-5-methyluridine

O²-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O-²-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P₂O₅ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry CH₂Cl₂ (4.5 mL) and methylhydrazine (300 mL, 4.64 mmol) was added dropwise at −10° C. to 0° C. After 1 h the mixture was filtered, the filtrate was washed with ice cold CH₂Cl₂ and the combined organic phase was washed with water, brine and dried over anhydrous Na₂SO₄. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5N-O-DMT-2N-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2N-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—$CH_2$—O—$CH_2$—N($CH_3$)$_2$, or 2'-DMAEOE nucleoside amidites) are prepared as follows. Other nucleoside amidites are prepared similarly.

2'-O-[2(2-N,N-dimethylaminoethoxy)ethyl]-5-methyl Uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy) ethyl)]-5-methyl Uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using $MeOH:CH_2Cl_2$: $Et_3N$ (20:1, v/v, with 1% triethylamine) gives the title compound. 5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3,-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. , 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligo-nucleosides, also identified as amide-4 linked oligonucleo-sides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligo-nucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphormidite for the DNA portion and 5'-dimethoxytrityl-2'-O-ethyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-ethyl amidites, oxidization with iodine to generate the hosphodiester internucleotide linkages within the wing portions of the chimeric structures and sulfurization utilizing 3, H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3, H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 4 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

Treatment with Antisense Compounds:

When cells reached 80% confluency, they were treated with oligonucleotide. For cells grown in 96-well plates, wells were washed once with 200 µL OPTI-MEM™-1 reduced-serum medium (Gibco BRL) and then treated with 130 µL of OPTI-MEM™-1 containing 3.75 µg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of RECQL2 Expression

Antisense modulation of RECQL2 expression can be assayed in a variety of ways known in the art. For example, RECQL2 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of RECQL2 can be quantitated in a variety of ways well known in the art, such as immunoprecipitation, Western blot analysis (immunoblotting), ELISA or fluorescence-activated cell sorting (FACS). Antibodies directed to RECQL2 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+ mRNA Isolation

Poly(A)+ mRNA was isolated according to Miura et al., *Clin. Chem.*, 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of RECQL2 mRNA Levels

Quantitation of RECQL2 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Cailf.) is attached to the 5' end of the probe and a quencher dye (e.g., TAMRA, obtained from either Operon Technologies Inc., Alameda, Calif. or PE-Applied Biosystems, Foster City, Cailf.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 µL PCR cocktail (1× TAQMAN™ buffer A, 5.5 mM $MgCl_2$, 300 µM each of DATP, dCTP and dGTP, 600 µM of dUTP, 100 nM each of forward primer, reverse primer, and probe, 20 Units RNAse inhibitor, 1.25 Units AMPLITAQ GOLD™ and 12.5 Units MULV reverse transcriptase) to 96 well plates containing 25 µL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 µL of RiboGreen working reagent (RiboGreen™ reagent diluted 1:2865 in 10 mM Tris-HCl, 1 mM EDTA, pH 7.5) is pipetted into a 96-well plate containing 25 µL purified, cellular RNA. The plate is read in a CytoFluor 4000 (PE Applied Biosystems) with excitation at 480 nm and emission at 520 nm.

Probes and primers to human RECQL2 were designed to hybridize to a human RECQL2 sequence, using published sequence information (GenBank accession number U39817, incorporated herein as SEQ ID NO:3). For human RECQL2 the PCR primers were: forward primer: GCTGCACTGCT-TGGTGAAGA (SEQ ID NO: 4) reverse primer: ACACAG-GCAGGGAGCTGGTA (SEQ ID NO: 5) and the PCR probe was: FAM-CACCTCCAGTCGGCATCAGGATAAAACA-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were: forward primer: GAAGGTGAAGGTCG-GAGTC (SEQ ID NO: 7) reverse primer: GAAGATGGT- GATGGGATTTC (SEQ ID NO: 8) and the PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of RECQL2 mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human RECQL2, a human RECQL2 specific probe was prepared by PCR using the forward primer GCTGCACTGCTTGGTGAAGA (SEQ ID NO: 4) and the reverse primer ACACAGGCAGGGAGCTGGTA (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human RECQL2 Expression by Chimeric Phosphorothioate Oligonucleotides having 2'-MOE Wings and a Deoxy Gap In accordance with the present invention, a series of oligonucleotides were designed to target different regions of the human RECQL2 RNA, using published sequences (GenBank accession number U39817, incorporated herein as SEQ ID NO: 3, genomic sequence complemetary to nucleotides 16501–116000 of GenBank accession number AC002312, incorporated herein as SEQ ID NO: 10, and GenBank accession number AI114820, incorporated herein as SEQ ID NO: 11). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human RECQL2 mRNA levels by quantitative real-time PCR as described in other examples herein. Data are averages from two experiments. If present, "N.D." indicates "no data".

TABLE 1

Inhibition of human RECQL2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|--------|--------|------------------|-------------|----------|---------|-----------|
| 137522 | Intron 2 | 10 | 4278 | ctaagaaatctgtatagcta | 37 | 12 |
| 137523 | Intron 2 | 10 | 6408 | ttttatgcataactaaactt | 29 | 13 |
| 137524 | Intron 2 | 10 | 12616 | gccactaagttttatggtaat | 65 | 14 |
| 137525 | Intron 2 | 10 | 23023 | tgcgtgccatcaagcccagc | 24 | 15 |
| 137526 | Intron 2 | 10 | 29576 | taggattacaggtgtgagcc | 15 | 16 |
| 137527 | Intron 15 | 10 | 69458 | aatcagctggccatggtggc | 29 | 17 |
| 137528 | Intron 17 | 10 | 79025 | tcttgaactcttgacctcag | 0 | 18 |
| 137529 | Intron 21 | 10 | 92713 | gcgactaggtaaagagagaa | 39 | 19 |
| 137530 | Intron 21 | 10 | 93137 | gtcctacaggccaccctaca | 46 | 20 |
| 137531 | 5'UTR | 3 | 39 | ctcctagcggacggaaccag | 47 | 21 |
| 137532 | 5'UTR | 3 | 52 | cctcgcacgcagactcctag | 43 | 22 |
| 137533 | Start Codon | 3 | 67 | aacagcagccataatcctcg | 50 | 23 |
| 137534 | Coding | 3 | 163 | agtgaaacctgaaaattttg | 52 | 24 |
| 137535 | Coding | 3 | 481 | actaaattctaatttcttga | 33 | 25 |
| 137536 | Coding | 3 | 539 | tatcaaagtcatccatatca | 57 | 26 |
| 137537 | Coding | 3 | 975 | tcttctggagaaggtggaac | 76 | 27 |
| 137538 | Coding | 3 | 1024 | ctttaacgtactaaggcatt | 50 | 28 |
| 137539 | Coding | 3 | 1183 | catcacatgaataagctgct | 81 | 29 |
| 137540 | Coding | 3 | 1189 | gtgctccatcacatgaataa | 74 | 30 |
| 137541 | Coding | 3 | 1195 | acagatgtgctccatcacat | 80 | 31 |
| 137542 | Coding | 3 | 1363 | atcaagtgaatcaggcctgt | 70 | 32 |
| 137543 | Coding | 3 | 1561 | acttacaaaggacttctgta | 76 | 33 |
| 137544 | Coding | 3 | 1568 | agttgctacttacaaaggac | 74 | 34 |
| 137545 | Coding | 3 | 1575 | tcagcccagttgctacttac | 82 | 35 |
| 137546 | Coding | 3 | 1582 | tggtgtttcagcccagttgc | 72 | 36 |
| 137547 | Coding | 3 | 1749 | tcatcatcatcaaagtcatc | 34 | 37 |

TABLE 1-continued

Inhibition of human RECQL2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 137548 | Coding | 3 | 1759 | ttcccagtcatcatcatcat | 50 | 38 |
| 137549 | Coding | 3 | 1799 | ctgtggaagatttgctggct | 70 | 39 |
| 137550 | Coding | 3 | 1930 | attctgaattgactctgaga | 69 | 40 |
| 137551 | Coding | 3 | 1947 | gctgacttgtcagtataatt | 63 | 41 |
| 137552 | Coding | 3 | 2069 | gattagttctaaaattatgc | 37 | 42 |
| 137553 | Coding | 3 | 2075 | ctagctgattagttctaaaa | 66 | 43 |
| 137554 | Coding | 3 | 2083 | gatcgcctctagctgattag | 79 | 44 |
| 137555 | Coding | 3 | 2090 | cagcattgatcgcctctagc | 80 | 45 |
| 137556 | Coding | 3 | 2130 | ccagtcggcatcaggataaa | 85 | 46 |
| 137557 | Coding | 3 | 2169 | acacaggcagggagctggta | 92 | 47 |
| 137558 | Coding | 3 | 2183 | tgaccccaggagaaacacag | 45 | 48 |
| 137559 | Coding | 3 | 2206 | tctcaagggagaaatgacaa | 61 | 49 |
| 137560 | Coding | 3 | 2235 | agcttttggacttgatctac | 50 | 50 |
| 137561 | Coding | 3 | 2242 | ggaagtcagcttttggactt | 56 | 51 |
| 137562 | Coding | 3 | 2271 | cctgtcagatatgtagctgg | 79 | 52 |
| 137563 | Coding | 3 | 2293 | agcttctgagtcagtcttat | 69 | 53 |
| 137564 | Coding | 3 | 2431 | aaaacgtgccaagagcttcc | 65 | 54 |
| 137565 | Coding | 3 | 2488 | gtaatcttgacgaaaatcat | 54 | 55 |
| 137566 | Coding | 3 | 2520 | ggaaacttctggcgaagcat | 78 | 56 |
| 137567 | Coding | 3 | 2527 | aacagaaggaaacttctggc | 67 | 57 |
| 137568 | Coding | 3 | 2592 | ttcagctgagtcaggatgtc | 57 | 58 |
| 137569 | Coding | 3 | 2623 | gctcatgctaaacacctgag | 72 | 59 |
| 137570 | Coding | 3 | 2630 | tgttaaagctcatgctaaac | 61 | 60 |
| 137571 | Coding | 3 | 2727 | cctgaatcatatgggtggtg | 42 | 61 |
| 137572 | Coding | 3 | 2746 | ggagaggcagtaaattatcc | 54 | 62 |
| 137573 | Coding | 3 | 2888 | cacagataacctgacagcca | 54 | 63 |
| 137574 | Coding | 3 | 2944 | atgaatcacaaatcgcacgt | 74 | 64 |
| 137575 | Coding | 3 | 2951 | gagatgcatgaatcacaaat | 68 | 65 |
| 137576 | Coding | 3 | 3011 | tttccccatctcttccagct | 52 | 66 |
| 137577 | Coding | 3 | 3019 | gtgagatatttccccatctc | 79 | 67 |
| 137578 | Coding | 3 | 3058 | cagtctggtcacatcatgat | 62 | 68 |
| 137579 | Coding | 3 | 3145 | acagtaatgtaccatgctat | 68 | 69 |
| 137580 | Coding | 3 | 3268 | atcctttgttttacagcaat | 65 | 70 |
| 137581 | Coding | 3 | 3412 | caagaaaatgtcgaccagca | 64 | 71 |
| 137582 | Coding | 3 | 3423 | ctcttactccccaagaaaat | 38 | 72 |
| 137583 | Coding | 3 | 3500 | gcttttaaaaagtctttcg | 51 | 73 |
| 137584 | Coding | 3 | 3539 | tgatatataagtcttcatcc | 64 | 74 |
| 137585 | Coding | 3 | 3552 | tggtcattggcattgatata | 59 | 75 |
| 137586 | Coding | 3 | 3623 | taaagtctacctttaaattg | 42 | 76 |
| 137587 | Coding | 3 | 3724 | tgtaagttctccaagacatt | 67 | 77 |
| 137588 | Coding | 3 | 3772 | attgaagtaatggacaccaa | 68 | 78 |
| 137589 | Coding | 3 | 3817 | agataaagattctgcaagct | 49 | 79 |
| 137590 | Coding | 3 | 3824 | gatcagaagataaagattct | 24 | 80 |
| 137591 | Coding | 3 | 3840 | tgaagcaaaacctcaggatc | 51 | 81 |
| 137592 | Coding | 3 | 3939 | ctgtcttcagctggcgatgt | 39 | 82 |
| 137593 | Stop Codon | 3 | 4318 | attcggttgttatgagaatg | 71 | 83 |
| 137594 | 3'UTR | 3 | 4361 | gtcagatgctgacaaacaag | 71 | 84 |
| 137595 | 3'UTR | 3 | 4369 | cacagatggtcagatgctga | 61 | 85 |
| 137596 | 3'UTR | 3 | 4377 | tttatagtcacagatggtca | 67 | 86 |
| 137597 | 3'UTR | 11 | 564 | ccagcatttatttaaatatt | 10 | 87 |
| 137598 | Intron 23 | 10 | 99076 | acaaaggtgacctacagctg | 19 | 88 |
| 137599 | Intron 2 | 10 | 26820 | gtgagcaattctgtgccact | 61 | 89 |

As shown in Table 1, SEQ ID NOs 14, 23, 24, 26, 27, 28, 29, 30, 31, 32, 33, 34, 35, 36, 38, 39, 40, 41, 43, 44, 45, 46, 47, 49, 50, 51, 52, 53, 54, 55, 56, 57, 58, 59, 61, 62, 63, 64, 65, 66, 67, 68, 69, 70, 71, 73, 74, 75, 77, 78, 81, 83, 84, 85, 86 and 89 demonstrated at least 50% inhibition of human RECQL2 expression in this assay and are therefore preferred. The target sites to which these preferred sequences are complementary are herein referred to as "active sites" and are therefore preferred sites for targeting by compounds of the present invention.

Example 16

Western Blot Analysis of RECQL2 Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to RECQL2 is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. An antisense compound 8 to 50 nucleobases in length targeted to a region of a nucleic acid molecule encoding RECQL2 of SEQ ID NO: 3, wherein said region is selected from nucleotides 67–183, 539–559, 975–1044, 1183–1215, 1363–1383, 1561–1602, 1759–1819, 1930–1967, 2075–2313, 2431–2650, 2727–2766, 2888–2971, 3011–3078, 3145–3165, 3268–3288, 3412–3432, 3500–3572, 3724–3860, 3939–3957, or 4318–4397, wherein said antisense compound specifically hybridizes with one of said regions and inhibits the expression of RECQL2.

2. The antisense compound of claim 1 which is an antisense oligonucleotide.

3. An antisense compound up to 50 nucleobases in length comprising at least an 8-nucleobase portion of SEQ ID NO: 14, 23, 24, 26, 27, 28, 29, 30, 31, 32, 33, 34, 35, 36, 38, 39, 40, 41, 43, 44, 45, 46, 47, 49, 50, 51, 52, 53, 54 55, 56, 57, 58, 59, 61, 62, 63, 64, 65, 66, 67, 68, 69, 70, 71, 73, 74, 75, 77, 78, 81, 83, 84, 85, 86 or 89 which specifically hybridizes to a nucleic acid molecule encoding RECQL2 and which inhibits the expression of RECQL2.

4. The antisense compound of claim 2 wherein the antisense oligonucleotide comprises at least one modified internucleoside linkage.

5. The antisense compound of claim 4 wherein the modified internucleoside linkage is a phosphorothioate linkage.

6. The antisense compound of claim 2 wherein the antisense oligonucleotide comprises at least one modified sugar moiety.

7. The antisense compound of claim 6 wherein the modified sugar moiety is a 2'-O-methoxyethyl sugar moiety.

8. The antisense compound of claim 2 wherein the antisense oligonucleotide comprises at least one modified nucleobase.

9. The antisense compound of claim 8 wherein the modified nucleobase is a 5-methylcytosine.

10. The antisense compound of claim 2 wherein the antisense oligonucleotide is a chimeric oligonucleotide.

11. A composition comprising the antisense compound of claim 1 and a pharmaceutically acceptable carrier or diluent.

12. The composition of claim 11 further comprising a colloidal dispersion system.

13. The composition of claim 11 wherein the antisense compound is an antisense oligonucleotide.

14. A method of inhibiting the expression of RECQL2 in cells or tissues comprising contacting said cells or tissues in vitro with the antisense compound of claim 1 to so that expression of REQL2 is inhibited.

15. The antisense compound of claim 3 which is an antisense oligonucleotide.

16. The antisense compound of claim 15 wherein the antisense oligonucleotide comprises at least one modified internucleoside linkage.

17. The antisense compound of claim 16 wherein the modified internucleoside linkage is a phosphorothioate linkage.

18. The antisense compound of claim 15 wherein the antisense oligonucleotide comprises at least one modified sugar moiety.

19. The antisense compound of claim 18 wherein the modified sugar moiety is a 2'-O-methoxyethyl sugar moiety.

20. The antisense compound of claim 15 wherein the antisense oligonucleotide comprises at least one modified nucleobase.

21. The antisense compound of claim 20 wherein the modified nucleobase is a 5-methylcytosine.

22. The antisense compound of claim 15 wherein the antisense oligonucleotide is a chimeric oligonucleotide.

23. A method of inhibiting the expression of RECQL2 in human cells or tissues comprising contacting said cells or tissues in vitro with the antisense compound of claim 3 so that expression of RECQL2 is inhibited.

24. A composition comprising the antisense compound of claim 3 and a pharmaceutically acceptable carrier or diluent.

25. The composition of claim 24 further comprising a colloidal dispersion system.

26. The composition of claim 24 wherein the antisense compound is an antisense oligonucleotide.

* * * * *